United States Patent [19]
Bender et al.

[11] Patent Number: 5,614,097
[45] Date of Patent: *Mar. 25, 1997

[54] COMPOSITIONS AND METHOD OF USE OF CONSTRUCTED MICROBIAL MATS

[75] Inventors: Judith A. Bender, Atlanta; Peter C. Phillips, Decatur, both of Ga.

[73] Assignee: Microbial and Aquatic Treatment Systems, Inc., Atlanta, Ga.

[*] Notice: The term of this patent shall not extend beyond the expiration date of Pat. No. 5,522,985.

[21] Appl. No.: 438,626

[22] Filed: May 10, 1995

Related U.S. Application Data

[63] Continuation-in-part of Ser. No. 339,548, Nov. 15, 1994, Pat. No. 5,522,985, which is a continuation of Ser. No. 40,628, Mar. 31, 1993, abandoned.

[51] Int. Cl.$^6$ .................................................. C02F 3/32
[52] U.S. Cl. ...................... 210/602; 210/150; 210/242.1; 47/1.4
[58] Field of Search ..................................... 210/602, 610, 210/611, 615, 747, 150, 151, 170, 242.1; 435/174, 177, 288, 310, 946; 47/1.4

[56] References Cited

U.S. PATENT DOCUMENTS

| | | | |
|---|---|---|---|
| 4,165,281 | 8/1979 | Kuriyama et al. | 210/150 |
| 4,333,263 | 6/1982 | Adey | 47/1.4 |
| 4,670,144 | 6/1987 | Francis | 210/150 |
| 5,011,602 | 4/1991 | Totani et al. | 210/242.1 |
| 5,039,414 | 8/1991 | Mueller et al. | 210/610 |
| 5,096,577 | 3/1992 | Ngo et al. | 210/151 |

FOREIGN PATENT DOCUMENTS

WO94/22773  10/1994  WIPO.

OTHER PUBLICATIONS

Bender, J.A., et al., "Fish Feeds from Grass Clippings," *Aquacultural Engineering*, vol. 8, pp. 1–13 (1989).

Cerniglia, C.E. et al., "Oxidation of Naphthalene by Cyanobacteria and Microalgae," *J. of Gen. Microb.*, vol. 116, pp. 495–500 (1980).

Bauer, J.E., et al., "Degradation and Mineralization of the Polycyclic Aromatic Hydrocarbons Anthracene and Naphthalene in Intertidal Marine Sediments," *Applied and Environ. Microb.*, pp. 81–90 (1985).

Bender, J.A., et al., "Lead Removal from Contaminated Water by a Mixed Microbial Ecosystem," *Wat. Sci. Tech.*, vol. 21, pp. 1661–1664 (1989).

Bender, J.A., et al., "Uptake, Transformation and Fixation of Se(VI) by a Mixed Selenium–Tolerant Ecosystem," *Water, Air and Soil Pollution*, vol. 59, pp. 359–367 (1991).

Ekpo, I., et al., "Digestibility of a Commercial Fish Feed, Wet Algae and Dried Algae by Tilapia nilotica and Silver Carp," *The Progressive Fish–Culterist*, vol. 51, pp. 83–86 (1989).

Brawley, J.P., Ph.D., *Reclamation of Metals from Water with a Silage–Microbe Ecosystem*, Mar. 1991.

*Primary Examiner*—Thomas G. Wyse
*Attorney, Agent, or Firm*—Jones & Askew

[57] ABSTRACT

Compositions and methods of use of constructed microbial mats, comprising cyanobacteria and purple autotrophic bacteria and an organic nutrient source, in a laminated structure, are described. The constructed microbial mat is used for bioremediation of different individual contaminants and for mixed or multiple contaminants, and for production of beneficial compositions and molecules.

19 Claims, 36 Drawing Sheets

COMPOSITIONS AND METHOD OF USE OF CONSTRUCTED MICROBIAL MATS

CROSS-REFERENCE TO RELATED APPLICATIONS

This is a continuation-in-part of U.S. patent application Ser. No. 08/339,548, filed Nov. 15, 1994, now U.S. Pat. No. 5,522,985, which is a continuation of U.S. patent application Ser. No. 08/040,628, filed on Mar. 31, 1993, abandoned.

TECHNICAL FIELD

The present invention relates to compositions and methods for environmental remediation and energy conversion. More particularly, the present invention comprises compositions and methods for effectively treating polluted or contaminated sites to remove from or contain the contaminating materials in the environment and to synthesize beneficial compounds. Additionally, the compositions and methods of this invention can be used to convert hazardous materials into small molecules, such as carbon dioxide and water, or to sequester the hazardous material into a more easily and safely manipulated form.

BACKGROUND OF THE INVENTION

Contaminants, such as hazardous, polluting or toxic materials or wastes, are a problem for the U.S. and for countries world-wide. Governmental agencies, commercial companies, the military, and consumers are searching for more cost-effective technologies that can be used to remove these hazardous and polluting materials.

Contaminants are continuously produced by activities of humans on the planet. In addition, natural causes can release or create contaminants in the environment. Oil and radioactive elements are naturally released into the environment and natural disasters, such as floods, create polluted areas in their wake. In addition to the on-going production of waste materials, there is a large amount of contaminants from activities in the past. Many of these past activities were not regulated by concerns for effects on the environment, and thus there are environmental problems dating back years or decades which require remediation.

The costs of cleaning up the environment are staggering. These costs are a drain on the economies of thriving countries and are an almost insurmountable problem for poorer countries. Many of the current technologies for removing hazardous or contaminating wastes from the environment involve sophisticated machinery or personnel, all of which add to the costs.

There are governmental attempts in the U.S. for correcting some of these environmental problems, such as the Superfund and Resource Conservation and Recovery Act, RCRA. In addition to legislative pressure for remediation, many commercial companies are interested in remediation. Not only are the companies compelled by the governmental regulations to stop adding hazardous materials to the environment and to clean up the existing hazards, but many states have prohibited the sale of real property unless the liability for any contamination discovered and any cleanup necessary is delineated. Additionally, consumers and members of the population who may be exposed to and harmed by the contaminants are creating pressure to remove pollutants from their environment. Therefore, there is a need by the government, by business entities, and by consumers for compositions and methods which can remove contaminants from the environment.

In the past, contaminants were contained by placing them in landfills or land treatment options. New technologies are now necessary because the costs of utilizing land as a holding site is too expensive or is prohibited by current regulations. Many of the contaminants thought to be isolated in landfills were found to be leaching into the surrounding environment, and thus were not "isolated" in the landfill. Companies now have to decontaminate millions of cubic yards of contaminated soil and millions of gallons of contaminated groundwater that cannot be placed in a landfill or incinerated because the costs are too high. Therefore, inexpensive methods and compositions are needed to decontaminate these materials.

Current methods of waste treatment are not adequate for remediating the contaminated air, soil or water by removing the contaminants. Physical methods such as adsorption, filtration or extractions are effective for some wastes. Unfortunately, additional treatments are often required to complete the decontamination because these treatments merely separate out the wastes but do not destroy the waste by converting it into a nonhazardous form. Chemical treatment can be used on some wastes, but there may be hazardous by-products or sludges produced by treatment. Wastes may be isolated or altered through methods such as stabilization, solidification or encapsulation, but the waste is merely contained, not destroyed. Additionally, the problem of storage of the contained waste is created.

Incineration is one effective method for reducing the volume of wastes and completely destroying the waste. Incineration is an expensive method and requires a large consumption of energy resources to remove the wastes. The gaseous emissions and toxic ash that result from the incinerator are new sources for contaminants in the environment. Additionally, consumers fear that operating incinerators will contaminate the environment with the by-products of the incinerator.

Biological treatment is another method of remediation that has been used for decades in wastewater treatment and composting processes. Such processes also produce sludges and wastewater that may require further treatment and disposal. There are many applications for biological treatments of hazardous wastes, but there are many engineering problems which must be overcome for biological systems to work efficiently to degrade and convert the hazardous materials.

Bioremediation occurs naturally at a low level and a very slow rate, even under ideal situations, in the biodegradation of material and wastes. Technologies using bioremediation methods take advantage of the naturally present degradative organisms to decontaminate air, soil or water. Currently, bioremediation methods fall into three broad categories-land treatment, bioreactors, and in situ treatment. In land treatment, the contaminated materials are mixed into surface soils or composted. These systems require the addition of bulking agents, aeration systems, water and nutrients to enhance the actions of the biological organisms.

Bioreactors are another means for bioremediation of contaminated materials. Lagoons, ponds, tanks or reactors with bacterial growth, are designed to decontaminate groundwater or such mixtures as slurries of soil and water. These methods may require that the contaminated water or slurry to be excavated, pumped or trucked to a distant site where the bioreactor is located. Additionally, the soils may have to be handled and sorted. After treatment at the bioreactor, any incompletely cleaned water or slurry would have to be transported elsewhere.

Transportation of hazardous wastes involves another set of regulations and requirements that can be expensive. Once in an ex situ reactor, the water or slurry has to be effectively mixed and aerated. Additionally, the growth of the bacteria in reactor must be controlled by controlling the residence time or the bacteria with the contaminated material, nutrient levels, temperature, pH, and concentration. If a batch process is used, only a limited amount of water or slurry can be decontaminated. These types of bioreactor systems are costly because of the capital, maintenance and operating expenses involved in running it.

On-site usage of bioreactors can eliminate the cost of trucking the material to the bioreactor, but the cost of excavation or handling of the soils is still present. These are generally not insignificant costs. In addition, the site may not lend itself to the presence of a bioreactor or support for the personnel necessary to oversee the reactor.

Another type of bioremediation, in situ remediation, utilizes the growth of indigenous, contaminant-degrading microorganisms which are present at the contaminated site. These organisms are present at the site and are capable of some kind of degradation of a contaminant. Unfortunately, their decontaminating action proceeds at too low a level and too slow a rate to effectively decontaminate the area. Additionally, the organisms may be only able to chemically change one contaminant in a mixed collection of pollutants, or only make a few chemical changes in a chemically-complex contaminating molecule. The growth of the naturally occurring microorganisms must be enhanced by the addition of oxygen and nutrients.

A major problem with in situ treatment using indigenous microorganisms is that the conditions of the site cannot be controlled like those of the bioreactor. This lack of control of such conditions as temperature, pH, and nutrient levels leads to a much longer time for decontamination of the site. It is also much harder to predict what the outcome of the treatment will be, how long the decontamination will take, and how the contaminants will be changed and how much will be changed.

Usually contaminated sites are contaminated by more than one kind of hazardous or polluting material. There is usually a mixture of several types of contaminants or several breakdown products of one contaminant. Currently, the number of contaminants which can be degraded by biological treatments is limited to a few organics and the processes are extremely sensitive to environmental conditions.

Therefore, what is needed are compositions and methods that can perform bioremediation within a contaminated or polluted site that is inexpensive, can be installed in the area without extensive structures or personnel to support it, and can be applied to a wide variety of environments. Even more ideally, would be a bioremediation system that would not only remove or stabilize the contaminated wastes, but could also convert the wastes into usable products such as energy sources or growth promoters. Such a biosystem could also be used to generate the beneficial products such as energy or growth promoters under conditions which promote the production and not only in waste treatment. Bioremediation systems which could clean up sites contaminated by a mixture of contaminants are also needed because very few sites are contaminated by only one contaminant. A bioremediation system that can clean up sites contaminated by both metals and organic materials is needed.

SUMMARY OF THE INVENTION

In accordance with the present invention, compositions and methods are provided that are effective in bioremediation and in production of useful by-products by a constructed microbial mat system. The present invention includes a constructed microbial mat of biological organisms that self-associate to form a complex ecosystem capable of removing contaminants from the environment. The constructed microbial mat comprises cyanobacteria and purple autotrophic bacteria and other microorganisms organized into a layered structure which is held together with slime, and has an organic nutrient source provided. The constructed microbial mat may optionally include support structures such as a mesh made from shredded coconut hulls or ground corn cobs, plastic mesh, limestone, glass wool, clay, concrete, wood fiber, activated charcoal, green filamentous algae, baffles, slowly turning paddles in a waterway, or any kind of bioreactor structures known in the art and combinations thereof.

The present invention comprises methods and compositions for treating contaminated sites by providing to the site a composition comprising a constructed microbial mat of cyanobacteria, purple autotrophic bacteria and an organic nutrient substrate such as ensiled material, and sometimes other microorganisms, to form a layered mat which can be supported by structures. The biological components such as the cyanobacteria and purple autotrophic bacteria self-assemble into a layered structure which can remove, degrade, or stabilize the contaminant or contaminants of the site. As used herein, removal of contaminants includes physical movement of the contaminant from the contaminated material such as water or soil to the constructed microbial mat or mat elements, or it can mean sequestering the contaminant within or adjacent to the constructed microbial mat, or entrapping the contaminant in some way by the constructed microbial mat or mat elements, or within the bodies of the mat biological components.

The contaminated material from the site may also be transported to the constructed microbial mat. The present invention is particularly useful for treating landfill leachate, metal contamination, radionuclide contamination, pollution by organic material, or sites with mixed contaminants.

The present invention also produces useful by-products from the bioremediation of contaminated sites or under normal growth conditions. The useful by-products can be used as food for animals, as growth stimulators, such as macrophyte growth stimulators, and high energy molecules. The present invention also includes production of bioflocculants which are capable of binding to metals and particulate matter and thus removing these contaminants from the environment or concentrating these materials for the recapture of valuable elements.

The present invention also includes kits for production of a mat. The kit can be in any configuration well known to those of ordinary skill in the art. The kits can be used to remove contaminants from environments as diverse as landfill leachate to small gallon aquaria.

Accordingly, it is an object of the present invention to provide a composition comprising a constructed microbial mat.

It is another object of the present invention to provide a method of treating contaminated sites with a constructed microbial mat to remove the contaminants.

Another object of the present invention is to provide a bioremediation or production site by the use of two constructed microbial mats.

Another object of the present invention is to provide a constructed microbial mat composition comprising indigenous microorganisms.

Another object of the present invention is to provide a constructed microbial mat composition comprising genetically engineered microorganisms.

It is yet another object of the present invention to provide a constructed microbial mat composition comprising microorganisms from sources such as isolates from contaminated areas, or adapted or engineered organisms.

Another object of the present invention is to provide a constructed microbial mat composition comprising microorganisms which have been made tolerant to high levels of the contaminants.

It is yet another object of the present invention to provide a constructed microbial mat composition comprising ensiled materials from various sources.

It is yet another object of the present invention to provide a kit for treating contaminated sites.

It is yet another object of the present invention to provide a method and composition for treating sites contaminated by metals.

It is yet another object of the present invention to provide methods and compositions for treating sites contaminated by organic materials.

It is an object of the present invention to provide methods of removing metals from the environment using a constructed microbial mat composition and to recover the metals from the constructed microbial mat composition.

It is an object of the present invention to provide methods and compositions for removing radioactive contaminants from a site.

Another object of the present invention is to provide methods and compositions for treating sites contaminated by a mixture of contaminants.

It is an object of the present invention to provide methods and compositions for removing contaminants from soil.

It is an object of the present invention to provide methods and compositions for removing contaminants from water.

It is an object of the present invention to provide methods and compositions for removing contaminants from the air.

It is yet another object of the present invention to provide compositions and methods for bioremediation comprising constructed microbial mats and inert structures.

It is another object of this invention to provide organic materials produced by the constructed microbial mat.

These and other objects, features and advantages of the present invention will become apparent after a review of the following detailed description of the disclosed embodiments and the appended claims.

BRIEF DESCRIPTION OF THE FIGURES

FIG. 4 shows that bioflocculant production is correlated with metal removal from the water column. 1/OD measures flocculating activity. The metal solution contained an initial phase manganese concentration of 20 mg/L. Percent manganese remaining in solution is plotted. Results show that as time increases bioflocculant activity increases and the metal concentration decreases.

FIG. 9a shows mineralization of hexadecane, in ng/hour under light conditions. FIG. 9b shows mineralization of hexadecane, in ng/hour under dark conditions. FIG. 9c shows mineralization of chrysene, in ng/hour under light conditions. FIG. 9d shows mineralization of chrysene, in ng/hour under dark conditions. CM+SS, constructed microbial mat (CM) and sterile silage (SS); CM+RS; constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage. The data represent a triplicate mean and is not cumulative.

FIG. 10a shows mineralization of hexadecane, in ng/day under light conditions. FIG. 10b shows mineralization of hexadecane, in ng/day under dark conditions. FIG. 10c shows mineralization of chrysene, in ng/day under light conditions. FIG. 10d shows mineralization of chrysene, in ng/hour under dark conditions. CM+SS, constructed microbial mat (CM) and sterile silage (SS); CM+RS; constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage. The data represent a triplicate mean and is not cumulative.

FIG. 11a shows the mineralization rate of hexadecane under light conditions. FIG. 11b shows the mineralization rate of hexadecane under dark conditions. FIG. 11c shows the mineralization rate of chrysene under light conditions. FIG. 11d shows the mineralization rate of chrysene under dark conditions. CM+SS, constructed microbial mat (CM) and sterile silage (SS); CM+RS; constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage.

FIG. 13a shows the chlordane chromatogram of Day 1. FIG. 13b shows the chlordane chromatogram of Day 3. FIG. 13c shows the chlordane chromatogram of Day 5.

DETAILED DESCRIPTION

Figure 1:
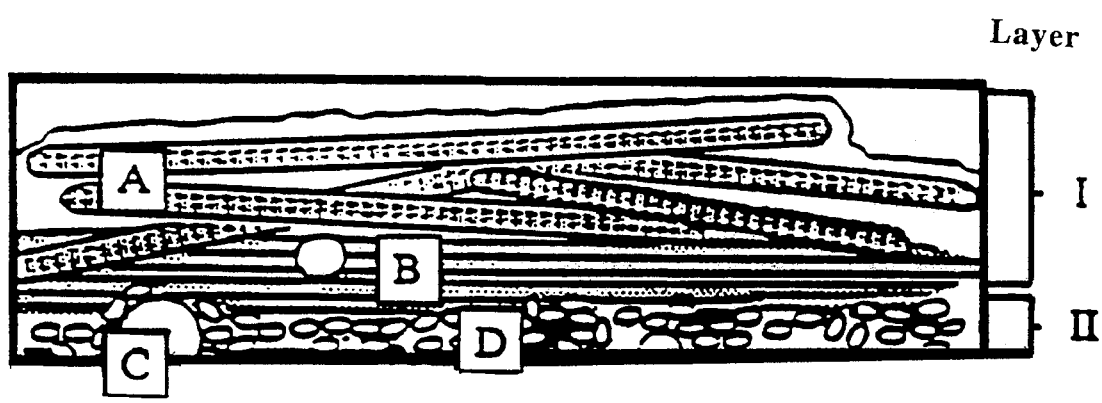
FIG. 1 is a schematic cross-section of a floating constructed microbial mat. Layer 1 is dominated by cyanobacterium *Oscillatoria* and Layer 2 is dominated by purple autotrophic bacteria. A=*Oscillatoria*, B=ensiled grass clippings, C=air bubble contributing to mat buoyancy, D=purple autotrophic bacteria.

This invention relates generally to compositions and methods for bioremediation and production of compounds. The compositions comprise a complex mixture of cyanobacteria, purple autotrophic bacteria, silage and other indigenous or exogenous microorganisms which are coalesced into a constructed microbial mat. The constructed microbial mat may be in a single layer or in a double layer. Additionally, the constructed microbial mat may be supported by inert materials such as organic materials such as a mesh made from shredded coconut hulls and ground corn cobs, plastic mesh, limestone, glass wool, clay, concrete, wood fiber and activated charcoal. Additionally, the constructed microbial mats may be incorporated into structures in which the constructed microbial mat can grow and thus be supported by baffles, slowly turning paddles in a waterway, or any kind of bioreactor known to those skilled in the art. Troughs and tanks can be used to support the constructed microbial mats, as can enclosed reactors similar to those used in traditional pump-and-treat systems. Bioreactors or other structures made of tubes or columns would also support the microbial mats.

The term, "remediation" as used herein, is the act or process of correcting a fault or deficiency. In the case of environmental remediation, it is the removal of contaminants, such as hazardous or polluting materials, from the surrounding environment. Bioremediation, as used herein, means using biological organisms, alone or in conjunction with inert structures, as a system for removing the contaminants, such as hazardous or polluting materials. Contaminant, as used herein, means any molecules, chemicals or organisms in the environment which are harmful to other living organisms in the environment or to the abiotic elements of the environment. The term, "toxic materials" as used herein, is included in the term contaminant. The contaminants may also be a natural element of the environment that is present in such a concentration that it is now harmful to the environment and its constituents. The contaminant may be an element which has been introduced into the environment by human activities, such as synthesis of the material, or by natural causes. The term contaminants, as used herein, encompasses the presence of one or more toxic, hazardous, or polluting materials in an area.

Contaminant, as used herein, also means any molecules, chemicals or organisms in the environment that are present in an undesired concentration or amount. The contaminant may not necessarily be harming any component of the environment but may be present in an undesired quantity.

The term, "environment" as used herein, is an area as defined by the situation and includes the biotic and abiotic elements, and the patterns of the interrelationships between the biotic elements, and between the biotic and abiotic elements which are found in the defined area. All three physical states, solids, liquids and gases, are included in the elements which make up the environment.

The constructed microbial mats of the present invention are comprised of heterotrophic and autotrophic communities dominated by cyanobacteria (blue-green algae). The constructed microbial mats are self-organized laminated structures annealed tightly together by slimy secretions from various microbial components, but primarily produced by the cyanobacteria. The surface slime of the constructed microbial mats effectively immobilizes the ecosystem to a variety of substrates, thereby stabilizing the most efficient internal microbial structure. Because constructed microbial mats are both nitrogen-fixing and photosynthetic, they are self-sufficient, solar-driven ecosystems with few growth requirements.

As used herein, the term "autotroph" is defined as an organism that is able to synthesize all needed organic molecules from simple inorganic substances (e.g., $H_2O$, $CO_2$, $NH_3$) and some energy source, such as sunlight. These are "self-feeders" as contrasted with heterotrophs that require external complex organic compounds. Heterotrophs are also known as the consumers in ecological terminology. Plants, algae and some bacteria are autotrophs. An exception to the autotrophic category is the group chemoautotroph. The members of this group do not used light and therefore are not photosynthetic. Chemoautotrophs are not photosynthetic, and many are anaerobes. Chemoautotrophs oxidize simple non-carbon compounds as a source of energy. Examples of chemoautotrophs are methanogens, nitrifiers and oxidizers (to $H_2SO_4$).

As used herein, purple autotrophic bacteria is a generic term for a large group of bacteria with certain characteristics. All members of this broad group are photosynthesizers, but can use other compounds instead of water as an electron source. They all contain pigments, but they are not always purple, and include bacterial species with a range of colors.

Some taxonomic delineations divide the purple autotrophic bacteria group into two sub-groups; purple sulfur and purple non-sulfur bacteria. The division is based on the type of electron source that the species uses for photosynthesis. Purple sulfur bacteria photosynthesize using $H_2S$, instead of $H_2O$ and producing either granules of sulfur or sulfate. Those that produce sulfate granules would not have sulfur granules appear in the cytoplasm and, therefore, would be more difficult to identify as a purple sulfur bacteria by microscopic analysis. Purple non-sulfur bacteria photosynthesize using organic material, such as alcohols and fatty acids as electron donors for photosynthesis instead of water. It is to be understood that the types of cyanobacteria and other microorganisms may vary and all such microorganisms which can function in the mat structure are contemplated as being included in the present invention.

Microbial mats are generated by enriching a water surface or a moist soil surface with ensiled grass clippings, called silage. The added cyanobacteria and purple autotrophic bacteria and any other indigenous and exogenous bacteria grow to form a complex constructed microbial mat with aerobic and anaerobic zones. These constructed microbial mats are durable, tolerant to a variety of toxins and resilient under changing environmental conditions. Additionally the constructed microbial mats can be designed for specific remediation tasks by culturing the desired microbes with the cyanobacteria and ensiled mixture. For example, constructed microbial mats with white rot fungus can be produced by this co-culture,. Both components, the algae and the fungus, become tightly integrated and grow rapidly, as a leathery unit, over the surface.

The constructed microbial mats of the present invention are comprised of nutrient organic substrates, such as ensiled materials, and microorganisms and can be immobilized on a variety of structures. The ensiled materials or waste biomass can be provided by, but are not limited to, such materials as grass clippings or other flora, including plant sources found at the contamination site. The plant sources are ensiled by enclosing the material in an anaerobic environment for 10 to 30 days, preferably 20 days, at room temperature. Once the ensiled material is mature, it can be mixed with the specific microbial components to form the constructed microbial mat. The community becomes organized into a highly durable sheet in approximately four to twelve days, depending on the environmental conditions.

The constructed microbial mats may be immobilized either by secretions from the bacterial components themselves or by inert structures added to the organic mat. Constructed microbial mats produce slimy secretions which stabilize the members of the microbial community in their stratified structure and also adhere the entire community to a variety of substrates. Several of combinations of constructed microbial mats and inert structures are used effectively for bioremediation applications. Constructed microbial mats in combination with glass wool removed zinc and manganese from water. Constructed microbial mats immobilized on clay mineralized carbofuran, chrysene, and TCE.

Constructed microbial mats, composed of stratified layers of microbes, are resilient communities dominated by cyanobacteria. Historically, cyanobacteria have occupied the most inhospitable environments on earth. For example, on a pond surface, cyanobacteria, which fix both carbon and nitrogen, provide the base of support, in the upper layer, for autotrophic bacteria that colonize lower layers. Purple autotrophic bacteria typically occupy the layer below the cyanobacteria where the light intensities and oxygen concentrations are low. This self-organizing consortium of microbes forms a laminated, multi-layered biofilm in water, sediments and soils. Once established, the constructed microbial mat becomes annealed together by a gel matrix and persists for long periods without added nutrient supplements. Examples of cyanobacteria are shown in Table I.

TABLE I

Examples of Blue Green Algae or Cyanobacteria

| Order | General Characteristics | Families | Representative Genera |
|---|---|---|---|
| CHROOCOCCALES | Plants unicellular or colonial; colonies not showing polarity; multiplication by binary fission or by endospores; no heterocysts. | Chroococcaceae Cyanochloridaceae Entophysalidaceae | Chroococcus, Microcystis Placoma, Entophysalis |
| CHAMAESIPHONALES | Plants unicellular or colonial; colonies showing distinct polarity; multiplication by endospores or exospores; no heterocysts. | Dermocarpaceae Chamaesiphonaceae Endonemataceae Siphononemataceae | Dermocarpa Stichosphon Chamaesiphon Endonema Siphononema |
| PLEUROCAPSALES | Plants filamentous; multiplication by endospores; no heterocysts. | Pleurocapsaceae Hyellaceae | Pleurocapsa Oncobyrsa Hyella, Solentia |
| NOSTOCALES | Plants filamentous but with no division into prostrate and upright filaments; multiplication by short motile filaments called hormogonia, with or without heterocysts | Oscillatoriaceae Nostocaceae | Microcoleus, Oscillatoria Phormidium, Spirulin Anabaena, Anabaenopsis, Nostoc, Wollea |
| STIGONEMATALES | Plants filamentous; showing distinct prostrate and upright systems; multiplication by hormogonia, or rarely by akinetes; heterocysts present. | Pluvinulariaceae Capsosiraceae Nostochopsidaceae Loefgreniaceae Stigonemataceae | Pulvinularia Capsosira Mastigocoleus, Nostochopsis Loeggrenia, Hapalosiphon Westtella |

TABLE II

Examples of Autotrophic (Chemotrophic and Phototrophic) Bacteria

Purple nonsulfur bacteria
Rhodopseudomonas
Rhodospirillum
Chromatiaceae
Thiocapsa BCh1a
Thiocapsa BCh1b
Chromatium
Thiocystis
Amoebobacter
Thiopedia
Ectothiorhodospiraceae
Ectothiorhodospira
Chlorobiaceae
Chlorobium (green)
Chlorobium (brown)
Pelodictyon
Chloroflexaceae
Chloroflexus
Chloroherpeton Constructed microbial mats are a consortium of microorganisms comprising purple autotrophic bacteria and *Oscillatoria* sp., a photosynthetic and nitrogen-fixing cyanobacterium. The floating mat on the surface of water is stabilized and nitrified by ensiled grass clippings schematically shown in FIG. 1. Layer 1 is dominated by cyanobacterium *Oscillatoria* and Layer 2 is dominated by purple autotrophic bacteria. A=*Oscillatoria*, B=ensiled grass clippings, C=air bubble contributing to mat buoyancy, D=purple autotrophic bacteria.

The water is inoculated with laboratory stocks or commercial sources of isolated purple autotrophic bacteria and *Oscillatoria*. The laboratory stocks include resilient, durable strains, which are resistant to toxic concentrations of a number of contaminants, toxic chemicals and metals. These bacterial sources are resistant to toxic concentrations of contaminants.

Figure 2:
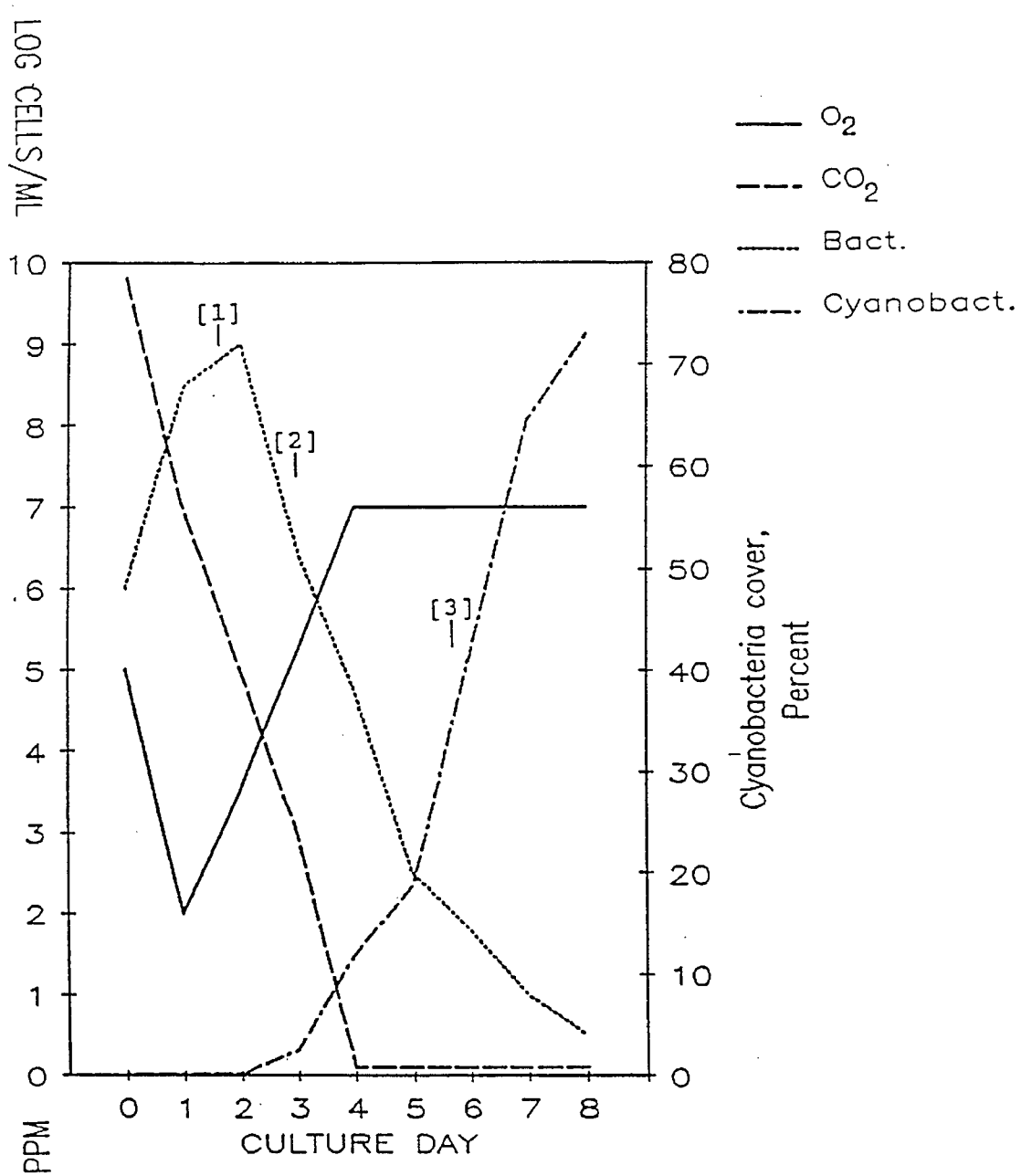
FIG. 2 is a graph showing the correlation of cyanobacteria growth with decreasing populations of bacteria in the water column. Bacteria (1) decrease in the water column as cyanobacteria (3) grows.

FIG. 2 illustrates a predictable succession of microbes that occurs in the water column when this mat consortium is developed in water lying over an optional soil bed. The graph of FIG. 2 shows that bacteria (1) decrease in the water column as *Oscillatoria* (3) grows. This effect of mat culture can be applied to bacterial removal, particularly in cases of pathogenic or coliform bacterial contamination. The oxygen level (2) initially drops but then stabilizes as the *Oscillatoria* increase. The $CO_2$ level drops steadily. Initially there is a bloom of a wide variety of heterotrophic bacteria (1–3 days) emerging from the soil bed, followed by a rapid colonization of the water column surface by *Oscillatoria*. As the *Oscillatoria* grows, the bacteria in the water column disappear.

The purple autotrophic bacteria migrate to the region under the *Oscillatoria*, where the purple autotrophic bacteria are supported by carbohydrates and proteins supplied by the cyanobacteria. However, the purple autotrophic bacteria retain mobility and part of the population often migrates away from *Oscillatoria* through the water or soil below the constructed microbial mat. The purple autotrophic bacteria are unable to sustain their viability for extended periods away from the constructed microbial mat without the addition of nutritional supplements.

It is important to note that purple autotrophic bacteria are capable of metabolizing a variety of chemicals for energy. Although purple autotrophic bacteria are autotrophic or photosynthetic, photosynthesis does not limit the chemotrophic responses. They are unique, primitive organisms which use $H_2S$ instead of water for photosynthesis. This sequestering of sulfide from water with subsequent oxidation to elemental sulfur removes some of the reducing potential of the environment and probably contributes to the elevated redox conditions that exist around the constructed microbial mats.

Mature constructed microbial mats become tightly annealed in a slimy matrix, primarily secreted by the cyanobacteria. The resulting laminated sheets of microbes have discrete oxidizing and reducing zones lying in close proximity within the matrix. These characteristics of availability of oxidizing/reducing zones, and elevated redox conditions in the water column likely contribute to the removal of various metals from water.

The *Oscillatoria* in the constructed microbial mat produces a slime or annealing gel which serves several functions in the bioremediation applications. The slime binds or anneals the various microbial components together, thereby, providing stability to the laminated structure and maintaining the positions of the microbial members. The slime anneals the constructed microbial mat to various non-living substrates such as glass wool, meshes (plastic, coconut), limestone, soil, corn cob particles, sediment and any other structures. This has the desired effect of keeping the constructed microbial mat consortium at the desired site for remediation.

Additionally, the slime provides some mechanical stability in terms of weather related impacts. Importantly, the slime also entraps gases. This may be important to the organic degradation rates because highly oxic zones develop in the region of entrapped photosynthetic oxygen. Since this gas does not migrate, adjacent respiratory processes can generate anoxic zones close the oxic region.

The entrapping of gases likely accounts for the buoyancy of the surface mats on the water column. Though *Oscillatoria* is the primary producer of the slime of the constructed microbial mat, other members of the consortia may produce slime.

The constructed microbial mat structure is ideal for degradation processes which require both oxic and anoxic zones for complete breakdown of the compounds, such as the complete degradation of recalcitrant organic contaminants. For example, chlordane may be degraded by reductive dechlorination in the anoxic zone, followed by ring cleavage in the oxic zone. The constructed mature constructed microbial mat was grown in a solution containing $^{14}C$-labeled chlordane. The $^{14}C$-labeled chlordane was 91% mineralized in 3 weeks. The radio-labeled carbon was distributed in the following products:

13% in carbon dioxide

78% in cellular macromolecules (proteins and carbohydrates)

2% in polar metabolites

7% unaccounted for

No parent compound was found at the end of the 3-week experiment.

The constructed microbial mats can exist under very diverse environmental conditions. The constructed microbial mats are effective within a large range of temperatures, from high temperatures of 95–110 F.° to freezing and slightly sub-freezing temperatures. Of course, prolonged exposure to extremes and lack of moisture may cause the constructed microbial mat organisms to become inert or with even more prolonged adverse conditions, may kill the organisms. Because the constructed microbial mat is a complex ecological unit, the constructed microbial mat can be self-sustaining for a long period of time. Thus, once in place, the constructed microbial mat can continue to decontaminate an area or continue to produce by-products of interest. The constructed microbial mats can exist under a wide variety of light conditions because there are not only photosynthetic organisms to provide energy to the system, but also chemosynthetic organisms to provide energy to the system.

The constructed microbial mats of the present invention can be developed at the site of the contamination on contaminated soil or water. The constructed microbial mats can also be used as an underground curtain to decontaminate a plume of underground water leaching from a contaminated site.

The constructed microbial mats of the present invention can also be used in constructed bioremediation systems such as leachate ponds or drainage ponds. The constructed microbial mats can be used in land treatments, in bioreactors or for in situ treatments.

The constructed microbial mats of the present invention can be used in many types of water, such as fresh, brackish or salty, and in lentic and lotic water. The constructed microbial mats can tolerate hypersaline conditions, approximately 100 parts per thousand, with no adaptation requirements. If necessary, mature constructed microbial mats are adapted to the target contaminants by step-wise exposure to increasing concentrations of the contaminant. Constructed microbial mats can survive, fore example, in variable concentrations of naphthalene and phenanthrene to 100 mg/L, chrysene to 50 mg/L, and pure hexadecane.

Constructed microbial mats can be immobilized on a variety of substrates including, but not limited to, coconut mesh, corn cob materials, glass wool, ceramic tiles, limestone pebbles, concrete and filamentous green algae. Commercial products, such as exploded corn cob particles, can also be used as a support structure. Constructed microbial mats can also be incorporated in bioreactor structures known to those skilled in the art. When immobilized on green algae, the mats are effectively protected from grazing predators in the field environment. Ponds containing constructed microbial mats immobilized on green algae have persisted in field ponds for at least two years.

Figure 3A:
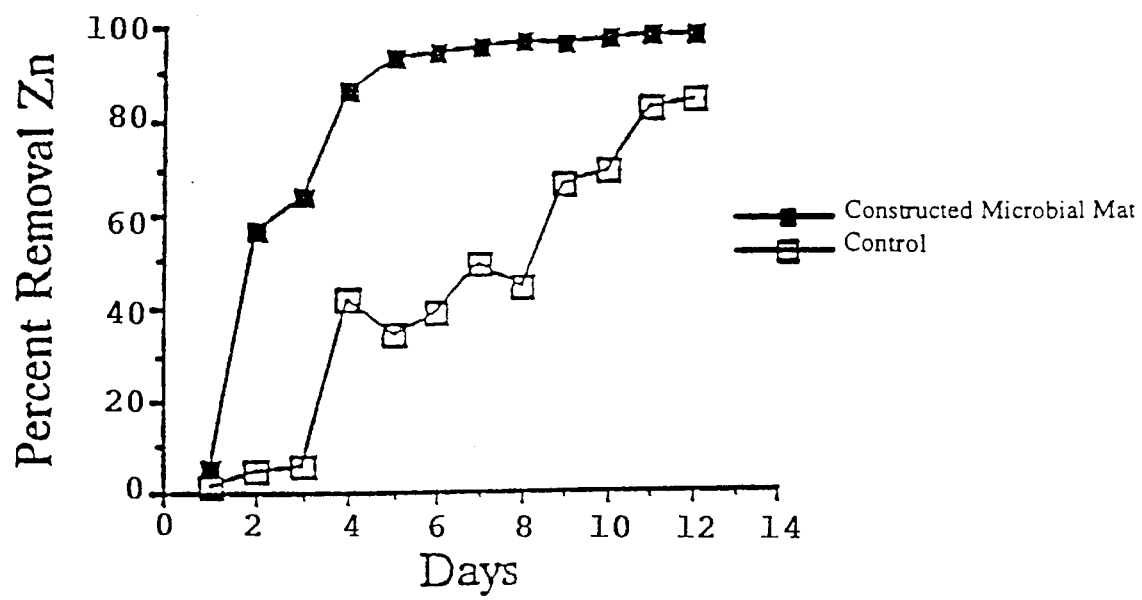
FIG. 3 shows removal of zinc and manganese by a constructed microbial mat. 3a is a graph showing the removal of manganese by a constructed microbial mat. 3b is a graph showing the removal of zinc by a constructed microbial mat.
Figure 3B:
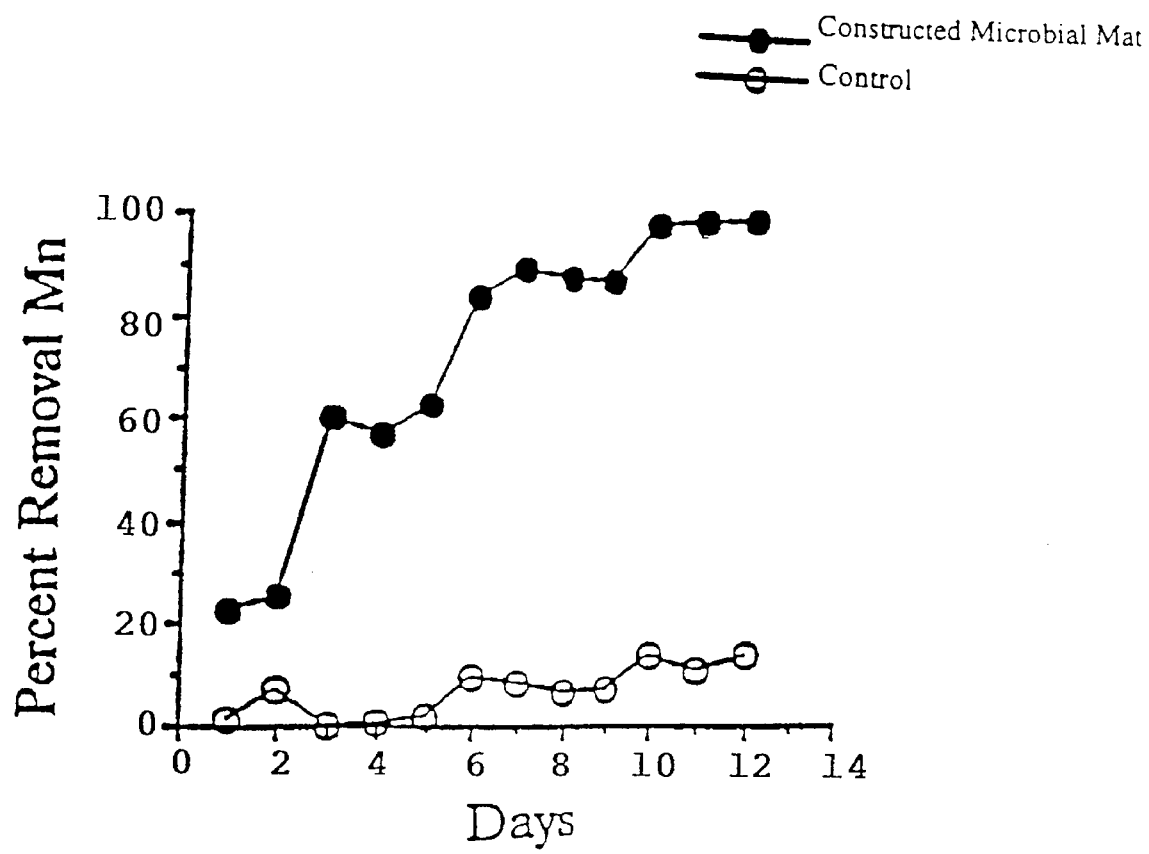

Applications of the Constructed Microbial Mats in Bioremediation:

Constructed microbial mats, constructed with specific microbial components, have been developed for various bioremediation applications. Constructed microbial mats reduce and recover selenate to elemental selenium, and recover silver, nickel, lead, cadmium, copper, zinc, cobalt, chromium, iron, uranium and manganese from water and remove lead from sediments. Uranium is also removed from contaminated sites such as groundwater. FIG. 3 shows graphs of percent removal of manganese (3*a*) and percent removal of zinc (3*b*) by constructed microbial mats.

The constructed microbial mats of the present invention can be used to degrade organic material contaminants, many of which persist for a long time in the environment. The degradation can occur under both dark and light conditions. The constructed microbial mats can degrade a wide variety of organic materials from such diverse sources as explosives, petroleum distillates, BTEX (benzene, toluene, xylene and ethylbenzene), and industrial effluents from pulp and paper industry. Compounds, including but not limited to the following, can be degraded by the constructed microbial mats of the present invention: chlordane, TNT, chrysene, naphthalene, hexadecane, phenanthrene, PCB, TCE, carbofuran, and paraquat. Other compounds such as the propellants DNT, RDX, HMX, nitrocellulose and nitroglycerine can also be degraded by the constructed microbial mats.

The elements of many these molecules can be "mineralized," degraded or converted into carbon dioxide and water. Degradation is defined as the breaking down of the original compound. Normally in biodegradation, the compound is metabolized by the biological organism. Degradation to the final step of mineralization is not always assumed to occur. The constructed microbial mats of the present invention are quite adept at complete degradation to the stage of mineralization of many of the complex organic compounds which are known contaminants.

The constructed microbial mats or by-products from the constructed microbial mats such as biofilms and bioflocculants can degrade a variety of chlorinated organics when present as single contaminants or in contaminant mixtures with heavy metals. The constructed microbial mats' degradation of chlorinated compounds provide solutions for common environmental problems such as treating dry cleaning solvents or unusual problems such as clean up of chemical weapons and their depots.

Chlorinated hydrocarbons are a significant contaminant throughout the world. Examples of such compounds are chlordane and heptachlor. Despite a two-decade ban on chlordane, chlordane persists in soils and in lake and river sediments. Chlordane and heptachlor are thought to be human carcinogens and tumor promoters. Chlordane is easily absorbed through the skin, is known to pass through the placenta and can be found in breast milk. Further, extensive exposure to chlordane may result in chlordane poisoning leading to various nervous system disorders. From the ecological perspective, the persistence of chlordane in the environment is well known, but its long-range impact on soil bacteria, flora and fauna has not been defined. Removal of chlorinated hydrocarbons from the environment by the constructed microbial mats would be an important step in restoring the environment.

Another organic contaminant that the constructed microbial mats of the present invention can degrade is 2,4,6-trinitrotoluene (TNT). About 40% of the thousands of toxic military sites are contaminated with TNT. TNT has been shown to be toxic to a number of organisms and has been classified as a possible human carcinogen. Therefore, biotransformation and biodegradation by the constructed microbial mats is an important method of cleaning up the TNT contamination.

Pesticide degradation in farm soils is a matter of grave concern for developing countries. Specifically, the persistence of organochlorines, such as chlordane, is a long-term threat to human health and ecological stability. For example, toxaphene, an organochlorine used on cotton fields and banned in Egypt since 1962, still enters that country due to its use in upstream Nile-basin countries. Levels to 10 mg/l were found in River Nile water, soil and biological samples.

Many countries have no governmental standards for use of pesticides or permissible levels of residues and also have no means of determining levels (presence or absence) of pesticide in food or water. The consumers in these countries are unwittingly exposed to these pesticides. For example, on the Caribbean island of St. Vincent, sixty percent of the native diet is derived from root crops and vegetables grown in and on pesticide-treated soil. When these crops are harvested 30 days after the application of a pesticide there is substantial reason to be concerned for the consumers' health.

The development of techniques to rapidly decontaminate farm soils, such as the constructed microbial mats of the present invention, is of paramount importance for human health and ecological stability.

Constructed microbial mats have a unique ability to actively sequester chlordane globules from the bottom of the water column via biofilms. For example, a biofilm, growing from the surface constructed microbial mat, has been seen to progressively extend toward the bottom of test tubes containing various concentrations of hexadecane. This film has demonstrated that it can sequester chlordane globules many times its own weight. This characteristic may be important to the removal of dense contaminants, which fall to the bottom and pollute the sediment regions of shallow ponds and estuaries.

Figure 4:
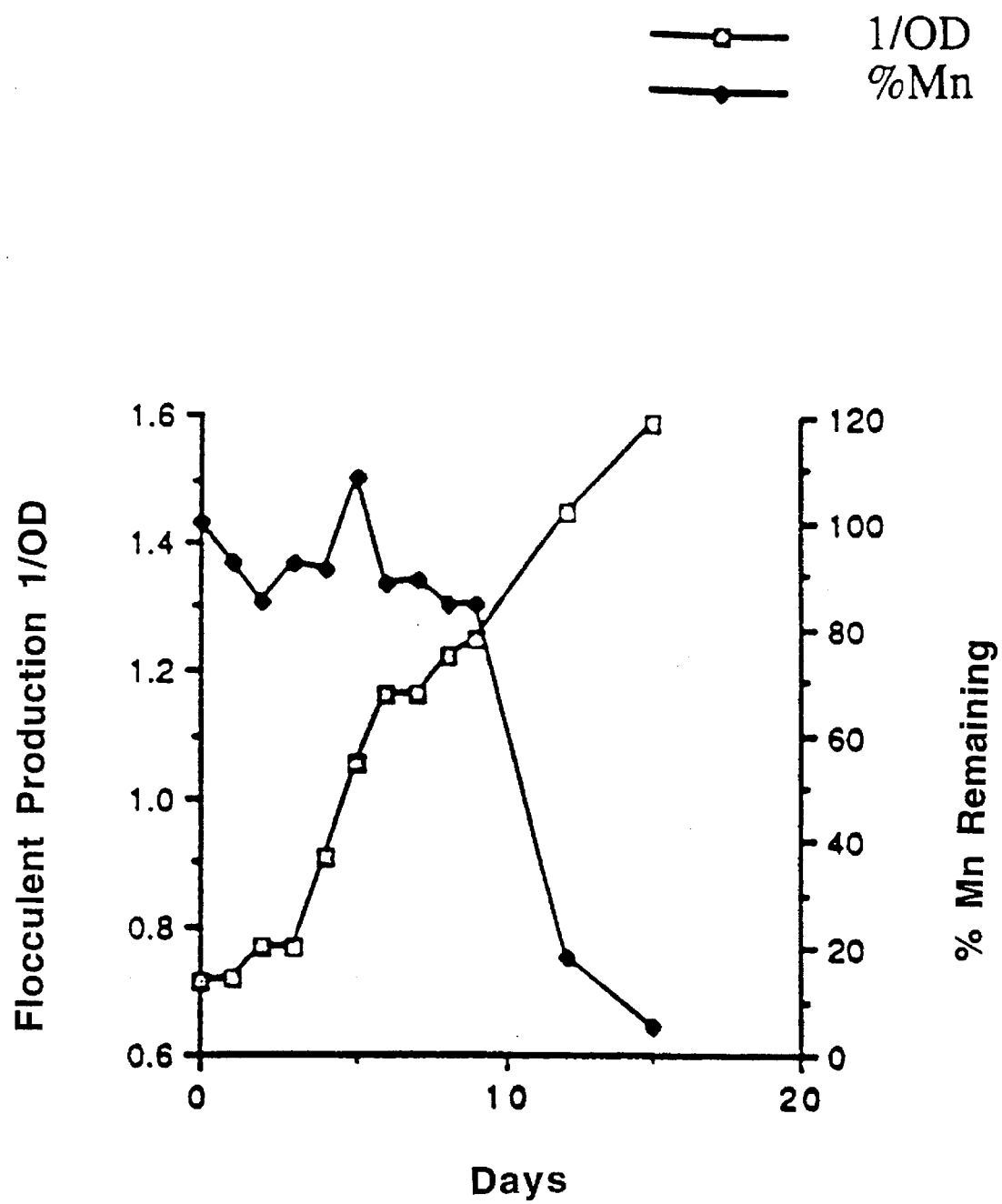
FIG. 4 is a graph showing the bioflocculant production and manganese removal from contaminated water.

Constructed microbial mats exhibit a number of characteristics that can be applied to simple waste water treatments. These properties include production of flocculants that clarify the water column of turbidity as seen in FIG. 4. FIG. 4 shows that bioflocculant production is correlated with metal removal from the water column. 1/OD measures flocculating activity. The metal solution contained an initial phase manganese concentration of 20 mg/L. Percent manganese remaining in solution is plotted. Results show that, as time increases, bioflocculant activity increases and the metal concentration decreases.

These properties also include sequester of eutrophying minerals; elevation of acidic pH levels (Table 3); degradation of organic materials and removal of heterotrophic bacteria, including coliforms from the water column. FIG. 2 illustrates that the decrease in the water column bacteria correlates with the growth of *Oscillatoria* on the pond surface.

TABLE 3

Aqueous pH changes mediated by constructed microbial mats over time.

| Day | Triplicate Mean pH |
|-----|--------------------|
| 1   | 5.20               |
| 2   | 6.52               |
| 3   | 6.94               |
| 4   | 7.20               |
| 5   | 7.79               |
| 6   | 8.29               |
| 7   | 8.80               |
| 8   | 9.25               |
| 9   | 9.83               |
| 10  | 10.14              |
| 11  | 10.34              |

Figure 5:
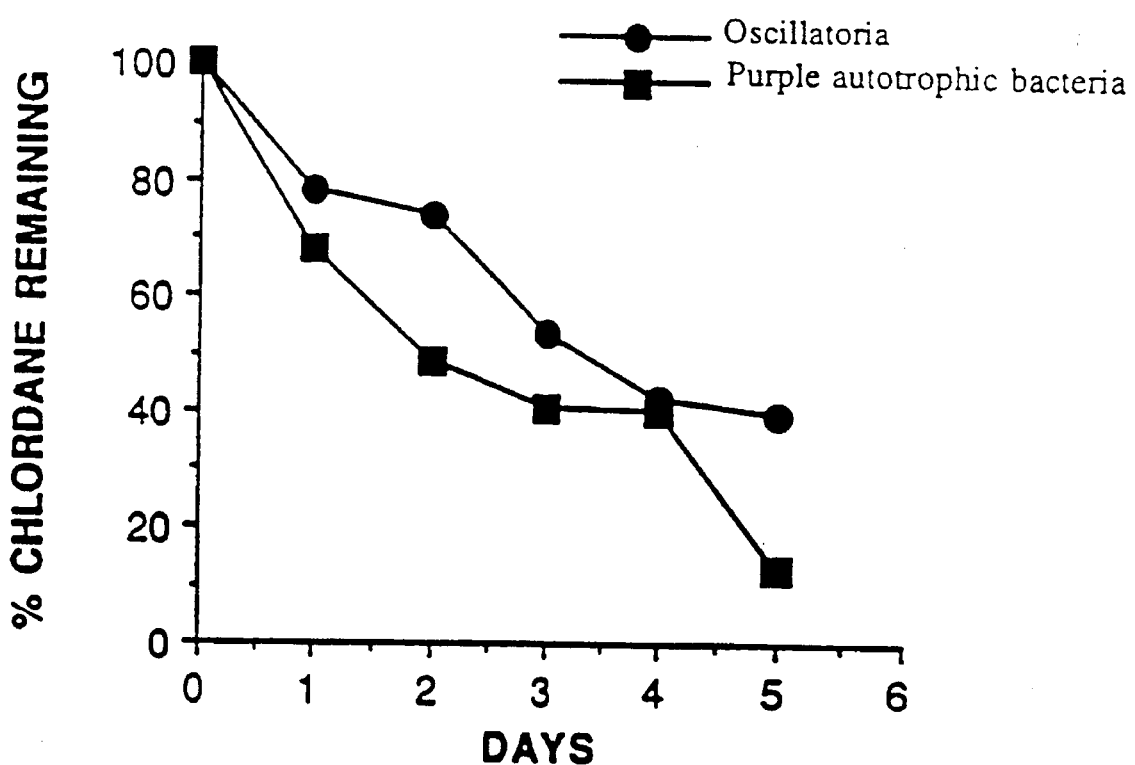
FIG. 5 is a graph showing chlordane removal by *Oscillatoria* and purple autotrophic bacteria.

Constructed microbial mats have successfully been used to degrade chlordane, hexadecane, chrysene, naphthalene, phenanthrene, 2, 4, 6-trinitrotoluene (TNT) and poly-chlorinated biphenyl (PCB). Representative data is presented in FIGS. 5–7 and Table 4. Chlordane in water degradation data demonstrates that purple autotrophic bacteria alone degrade chlordane at a faster rate than does *Oscillatoria* alone. FIG. 5 shows chlordane removal by *Oscillatoria* and purple autotrophic bacteria. By day the degradation by purple autotrophic bacteria is significantly greater than by *Oscillatoria* (<0.01). Without the presence of the *Oscillatoria*, the purple autotrophic bacteria needs nutrient supplements for continued degradation activity.

Figure 6A:
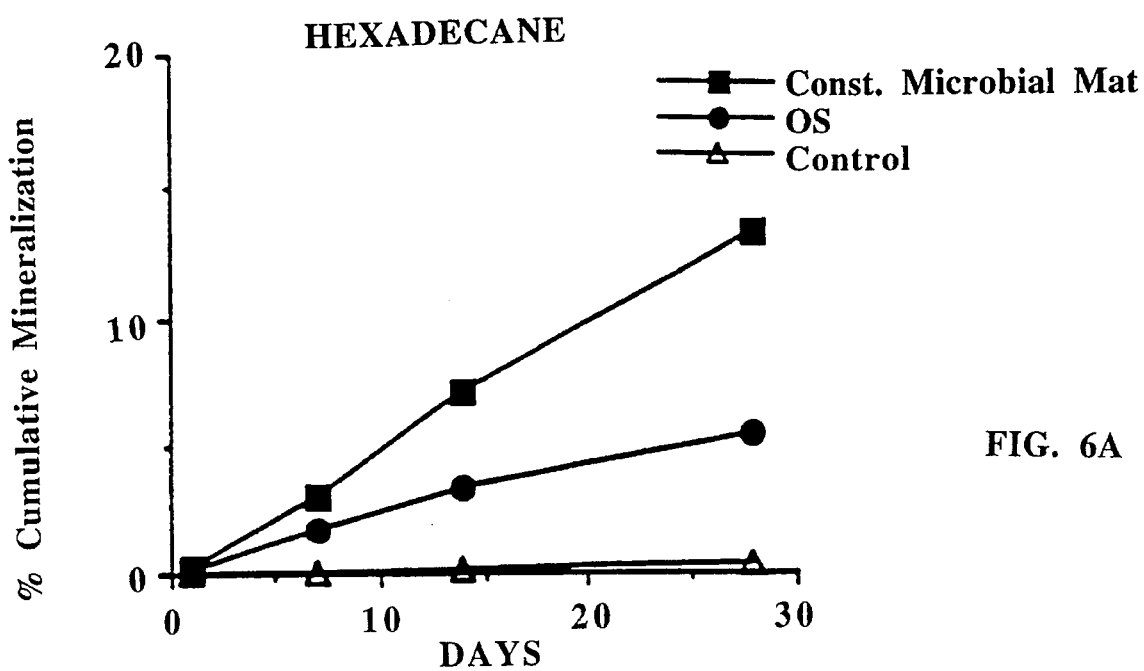
FIG. 6 shows mineralization of hexadecane and chrysene. 6a is a graph showing the mineralization of hexadecane. 6b is a graph showing the mineralization of chrysene. OS=*Oscillatoria* alone. Cumulative percent mineralization of hexadecane or chrysene (measured by trapping radiolabeled carbon dioxide in potassium hydroxide) by *Oscillatoria* or a constructed microbial mat. Purple autotrophic bacteria significantly enhance the degradation of these two petroleum distillates.
Figure 6B:
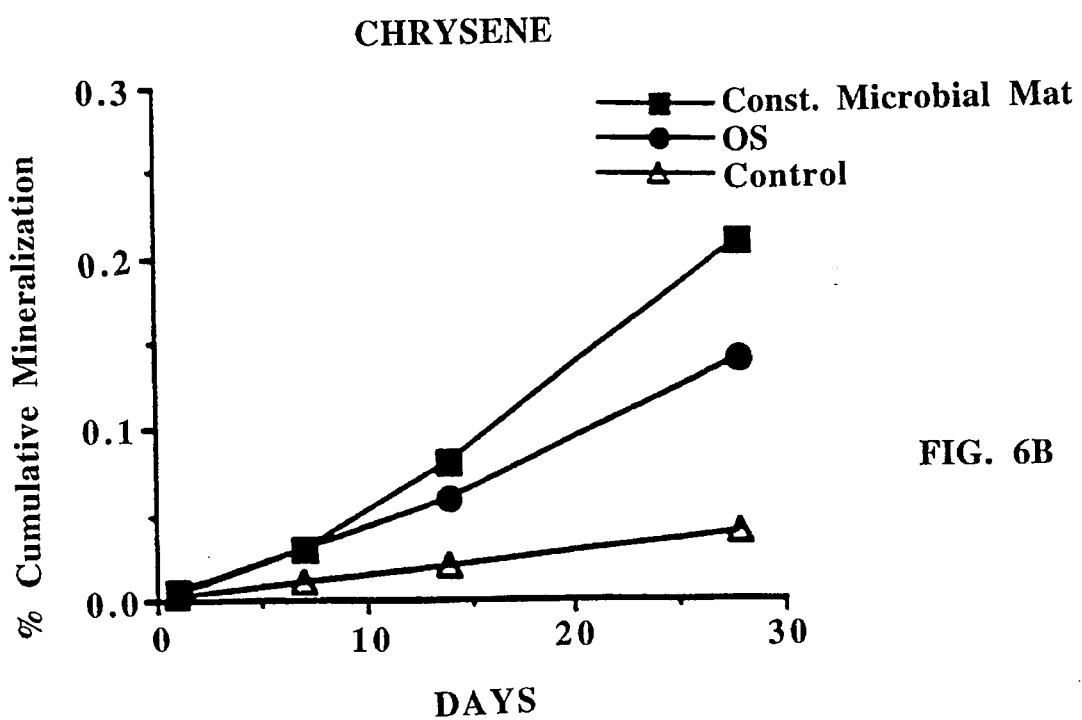

FIG. 6 shows the cumulative percent mineralization of hexadecane (FIG. 6a) or chrysene (FIG. 6b) which is measured by trapping radiolabeled carbon dioxide in potassium hydroxide by *Oscillatoria* or a constructed microbial mat. Purple autotrophic bacteria significantly enhance the degradation of these two petroleum distillates. OS=*Oscillatoria* alone.

Figure 7:
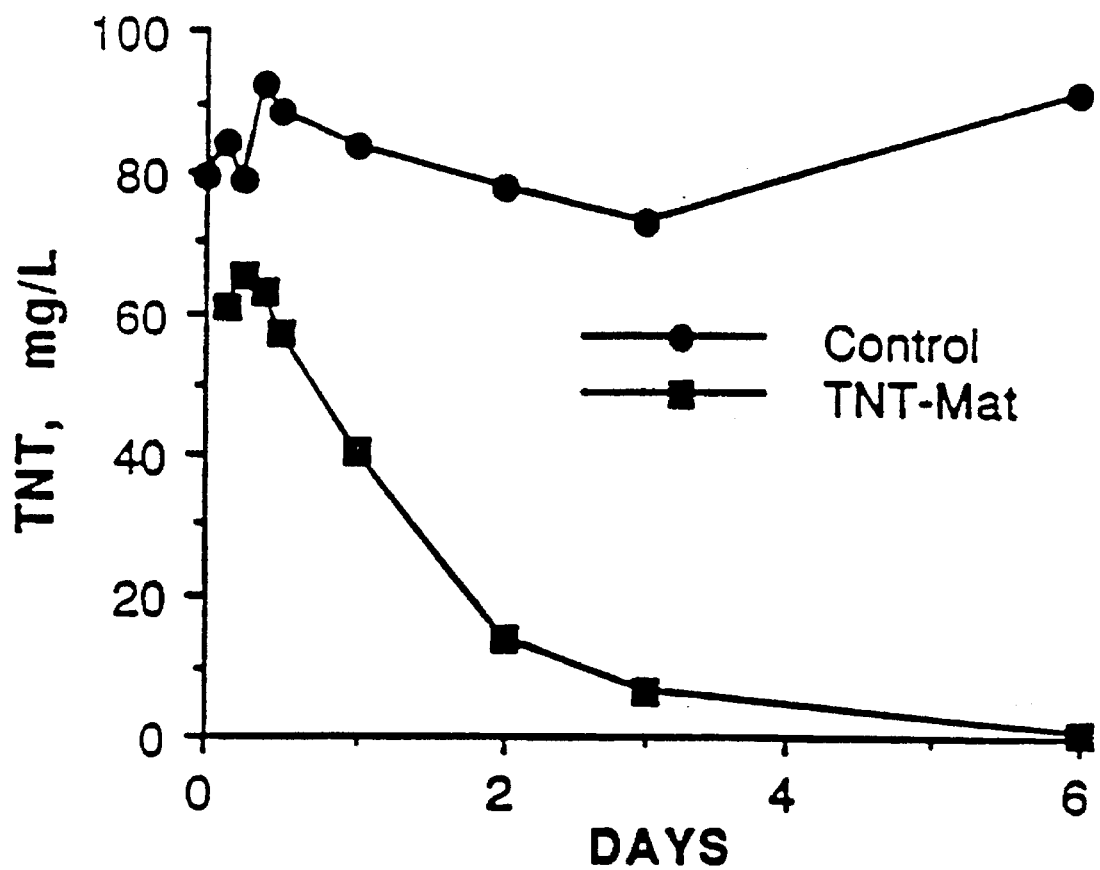
FIG. 7 is a graph showing 2,4,6-trinitrotoluene (TNT) degradation by a constructed microbial mat resistant to toxic concentrations of TNT.

FIG. 7 is a graph showing the degradation of 2,4,6-trinitrotoluene (TNT) by a constructed microbial mat resistant to toxic concentrations of TNT.

TABLE 4

Biodegradation of organic compounds by constructed microbial mats.

| Contaminant | Concentrations, mg/L | | Time and percent removal |
|---|---|---|---|
| | Initial | Final | |
| Chlordane | | | |
| in water | 2,100 | 61 | 97% in 10 days |
| in soil | 200 | 146 | 27% in 25 days |
| Petroleum distillates[1] | | | |
| hexadecane | 768 | 697 | 9% in 90 days |
| phenanthrene | 374 | 284 | 24% in 90 days |
| chrysene | 157 | 125 | 20% in 90 days |
| 2,4,6-trinitrotoluene (TNT) | 100 | <1 | >99% in 6 days |
| PCB | 100 | EIP[2] | 50% in 5 days |

[1]Percent degradation for petroleum distillates designate mineralization in dark cycle experiments (determined by $^{14}$C-labeled carbon dioxide collected in potassium hydroxide traps). Quantity of constructed microbial mat (mat surface area, cm$^2$) applied to the various substrates were: TNT = 2.0 per petri plate, chlordane in water = 16.0 per 50-ml media, chlordane in soil = 2.5 per test tube, petroleum distillates = 2.0 per 100-mL media.
[2]Experiment in progress Chlordane in soil is rapidly degraded by the constructed microbial mat. There is an intense purple autotrophic bacterial bloom in water with chlordane. A similar phenomenon of purple autotrophic bacteria penetration in soil was observed. In the example of hexadecane and chrysene, complete mineralization to carbon dioxide occurs with *Oscillatoria* but is significantly enhanced when purple autotrophic bacteria are present with in a constructed microbial mat with *Oscillatoria*. TNT is also degraded with the complete constructed microbial mat.

Many of the contaminants that the constructed microbial mat can degrade are normally toxic to biological organisms found in the mat. Therefore, the constructed microbial mats are often constructed with biological organisms that are resistant to a toxic concentration of the contaminant or contaminants. The organisms are specifically selected for their resistance to the toxic concentration and are then exposed to gradually increasing amounts of the contaminant. These organisms are then considered "resistant" to the toxic concentrations of the contaminants and can be used at contaminated sites with high concentrations of the contaminants. The selected organisms are either purple autotrophic bacteria alone, the cyanobacteria alone, other specific organisms, or the entire mat consortium.

The constructed microbial mats of the present invention offer a broad range of mechanisms related to the sequestering of heavy metals, the biodegradation of recalcitrant organics and remediation of mixed organic and inorganic contaminants such as TCE and carbofuran with heavy metals. Though not wishing to be bound by any particular theory, it is believed that the diverse microbial components within the constructed microbial mat define the range of molecular, cellular and communal mechanisms available in this ecosystem and likely account for the broad range of successful bioremediation applications of which the constructed microbial mats are capable. Diverse microbes organize into discrete microzone of highly contrasting oxic and anoxic character. These zones exist in close proximity and support aerobic and anaerobic communities simultaneously, thereby offering a unique array of biochemical mechanisms for degradation of recalcitrant organics, such as chlorinated aromatics.

Although not wanting to be bound by any particular theory, it is believed that motile bacteria of the constructed microbial mat may aid in transport of material to the constructed microbial mat. A theory for the ability of the constructed microbial mat to degrade chlorinated compounds in soil is that motile bacteria, associated with a constructed microbial mat growing on the soil surface, can penetrate clay soils and degrade the chlorinated compound mixed within the soil. Because heavy metal and metalloid contaminants are taken up and concentrated by constructed microbial mats in quiescent ponds, the theorized mechanism is that the metal is transported through the water. It is believed that motile bacteria bind to the metals and migrate to the constructed microbial mat by responding chemotactically to the cyanobacteria and ensiled components of the constructed microbial mat.

It is believed that bioflocculants produced by the constructed microbial mat play a key role in both metal sequestering and organic degradation. It has been found that metals bind to the bioflocculants. Additionally, cell-free biofilms produced by the constructed microbial mat physically sequester materials from the sediment region. An insoluble chlordane globule was picked up by a biofilm, transported to the constructed microbial mat and degraded in 61 days. Excised portions of a cell-free biofilm has been shown to mineralize TCE and carbofuran.

It is also believed that the constructed microbial mats produce specific regions for oxidation and reduction reactions to occur. Additionally, the constructed microbial mats can create conditions of high oxygen in certain areas and an anaerobic environment in other regions. This variety of microenvironments within the complex ecology of the constructed microbial mat allow for the degradation and sequestration of a wide variety of contaminants.

The constructed microbial mats are also capable of removing ammonium ions from water. Ammonium ions are a major contaminant found in the leachate of lined landfills. The constructed microbial mats can be used to stabilize a landfill with leachate treatment and simultaneously, produce high energy molecules.

The constructed microbial mats can be used in a landfill site in the following way. Cycling landfill leachate through a constructed microbial mat pond and allowing the treated water to seep back into the landfill have several important effects that can be integrated into a comprehensive treatment system with energy production. Leachates that collect in lined landfills generally contain mixed organic and inorganic contaminants. The leachate is also frequently saline. Because constructed microbial mats can grow in a broad range of salt concentrations and treat mixed contaminants, the constructed microbial mats will decontaminate the leachate. If constructed microbial mats are grown in shallow ponds on the landfill surface the leachate can be passed through the ponds and decontaminated for other uses, or be cycled back into the landfill.

The circulation of the water decontaminated by constructed microbial mats back into the landfill has several advantages. The toxic materials of the untreated leachate inhibit the growth of indigenous microorganisms of the landfill and thus slow down the overall recycling of the landfill material. After treatment by the constructed microbial mat, the treated leachate no longer contains these inhibitory compounds and instead, contains nutrients such as polysaccharides and proteins released by the constructed microbial mat. The treated leachate also contains a variety of microbes contributed by the constructed microbial mat consortium. The combination of the lack of inhibitory materials with the beneficial nutrients and additional microbes increases the microbial processes within the landfill and speeds up the processes of landfill stabilization.

It is known that landfills go through discrete phases, some of which release methane and hydrogen gases. One major problem relating to the utilization of landfill gases is the duration and concentration of gas generation. If microbial processes are slow, the landfill stabilization is prolonged and gas production is extended over long periods of time at low rates. This makes collection and use of the gases an inefficient process. The constructed microbial mat treatment of leachate ponds, with subsequent recycling of treated water through the landfill, produces a rapid stabilization resulting in higher concentrations of methane and hydrogen released over shorter periods of time.

Another consequence of treatment of leachates by constructed microbial mats is the generation of a high volume of constructed microbial mats in a relatively short time span. Constructed microbial mats produce high molecular weight hydrocarbons, similar to petroleum molecules. The hydrocarbon production is dependent on the rate of constructed microbial mat production. Mat production is frequently limited by photosynthetic and nitrogen fixation rates. Because leachates often contain carbon compounds and ammonia, there is a steady supply of materials for the constructed microbial mat organisms. Therefore, the rate of growth of the constructed microbial mat is not limited by the production of these essential starting compounds and rapid constructed microbial mat production is expected. Therefore, more hydrocarbons will be produced in the rapidly growing constructed microbial mats.

Not only is the present invention directed to methods and compositions which are capable of bioremediation of a wide variety of contaminants and contaminated sites, it is also directed to methods and compositions for producing a variety of molecules or structures as metabolic by-products of the constructed microbial mat. Such by-products include organic materials produced by the constructed microbial mat.

Bioflocculants are one of the kinds of organic materials produced by a constructed microbial mat. Bioflocculants bind metals and particulate matter. The binding by bioflocculants of heavy metals or other contaminants in water may contribute to the clean-up of contaminated water sites. Bioflocculants are produced by soil bacteria and may be useful in cleansing contaminated soil sites.

Macrophyte growth stimulators are another kind of organic material produced by a constructed microbial mat. Incorporation of constructed microbial mats with soil has increased the growth rate of plants compared to plants in soil without incorporated constructed microbial mats. The incorporation of the constructed microbial mat into the soil may also aid the soil in retention of water, thus preventing the dehydration of the plants.

The constructed microbial mat may also be used in conjunction with the root systems of higher plants to bioremediate contaminated soils. The constructed microbial mat consortium would comprise the cyanobacteria, purple autotrophic bacteria, other bacteria and the roots of the plant. This procedure is used to get effective microbes into deeper soils or into deep sediments. A constructed microbial mat slurry is made by using blended whole constructed microbial mats or members of the constructed microbial mat consortium. The roots of the plants would be bathed in a constructed microbial mat slurry and then the plants are inserted into the contaminated site. Research has demonstrated that constructed microbial mat microbes colonize around the roots after planting and remain associated with them over time.

Constructed microbial mats can also been used as a food source for aquatic life. The development of low-cost fish feed is important for aquaculture systems. A constructed microbial mat is constructed on the surface of a pond and fish living in the pond can feed on the constructed microbial mat. Selected microorganisms can be incorporated in the constructed microbial mat for additional nutrients or for other beneficial effects to the fish diet.

Constructed microbial mats are not limited to only providing fish food, but could also be a high protein food source for other animals, including but not limited to cattle, sheep, and chickens. Selected microorganisms can be incorporated into the constructed microbial mat to provide additional nutrients or colorants which are beneficial for the animal consumer. Additionally, the constructed microbial mats could be used as a food source or vitamin source for human consumption.

Constructed microbial mats are also capable of producing anti-bacterial materials. Constructed microbial mats remove bacteria from the water as the cyanobacteria population increases in the constructed microbial mat.

Constructed microbial mats produce high-energy molecules which may be used for energy production. High molecular weight hydrocarbons are produced by the constructed microbial mats and are stored within the cells of the organisms which make up the constructed microbial mat. Additionally, the constructed microbial mats reduce selenate without stirring or bubbling for exposure, indicating the release of hydrogen gas. Another energy molecule, methane is released by the methanogen organisms in the constructed microbial mats during the night cycle of the constructed microbial mat. Therefore, some of the high-energy molecules produced by a constructed microbial mat include large hydrocarbons, methane and hydrogen. This alternative energy production is essentially a solar-conversion process, with photosynthetic fixation of carbon being the initial and central cellular mechanism for this production.

In summary, this invention is directed to a constructed microbial mat for bioremedial applications such as oil or petroleum degradation, metal sequestration or other toxic material or contaminant degradation. The constructed microbial mats are also capable of producing organic materials which may be useful in bioremediation or in energy production. Such constructed microbial mats not only have the capability of remedial action but also have high tolerance to toxic materials and remain active over extended periods of time. Constructed microbial mats can be constructed which are tolerant to wide variety of conditions and contain specific microorganisms for degradation of specific materials in the environment.

The invention comprises a constructed microbial mat containing resistant microorganisms, along with other microorganisms, which have the ability to withstand the presence of and or to metabolically process various contaminants, such as metals, bacteria, or organic molecules. When the constructed microbial mat contains organic nutrient substrate, such as ensiled vegetation with fermentative and nitrogen-fixing bacteria, the remediation of the organic compounds is sustained over extended periods of time and at elevated remediation rates.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLE 1

Production of a Constructed Mat

The following steps summarize the procedures for producing constructed microbial mats:

Add organic nutrient substrate, such as ensiled grass clippings (approximately 7 g/L) made from fresh-cut grass clippings (mixed wild grasses) that are packed into 1-liter jars, excluding air pockets, and allowed to process anaerobically for 20 days at room temperature, to the surface of a water column. A shorter ensiling period of 5–10 days may be used if acetic acid silage feed stock is desired, rather than the mature silage which contains lactic acid.

Add the microbial mixture (0.1–0.5 g/L each), such as *Oscillatoria* and purple autotrophic bacteria. The finished silage is used to enrich the water column in order to stimulate the microbial bloom and provide a substrate for cyanobacteria attachment at the surface of the water column.

Depending on the situation the constructed microbial mat is being used in, there may or may not be an attempt to maintain a sterile system or to control the types of heterotrophic bacteria that may integrate with the constructed microbial mat.

Two microbial strains are considered as essential to the treatment system. These are *Oscillatoria* and purple autotrophic bacteria. Each of these easily colonizes on the organic nutrient substrate and is not eliminated by competitive interferences of other heterotrophs. Additionally, a mixed population of fermentative bacteria may be added with the organic nutrient substrate, such as ensiled grass clippings. It is assumed that the mixed heterotrophic populations from the soil and grass clippings may actually enhance degradation of certain compounds as long as the two inoculated strains retain their integrity. In summary, after the inoculation of the two strains, there is a natural, balanced self-organization of the microbes into a constructed microbial mat dominated by a slime-producing cyanobacteria layer, such as *Oscillatoria*, with a purple autotrophic bacteria layer on the underside of the constructed microbial mat. This self-organization and long-term structural durability of the system is highly reproducible.

Illuminate with incandescent lights (60 watt at 25 cm from surface). Partially cover with clear plastic to minimize evaporation.

Bacterial phase develops spontaneously (1–3 days).

Cyanobacteria spontaneously establishes dominance in 4–7 days. Allow the constructed microbial mat 10–15 days to mature. Replace evaporated water with tap water. Constructed microbial mats tolerate tap water, and fresh and brackish water from the field environment. Saline water may also be used. Slime will anneal the cyanobacteria layer and the purple autotrophic layers, along with the organic nutrient substrate dispersed throughout the layers. Slime may also anneal the constructed microbial mat to any support structures which are present, such as coconut mesh or bioreactor materials.

Thereafter use excised sections of mature constructed microbial mat for microbial inoculum (1–2 $cm^2$/L water).

EXAMPLE 2

Construction of Microbial Mats Resistant to Toxic Levels of Contaminants

A constructed microbial mat is developed as described in Example 1. Sections of the mature constructed microbial mat are excised and each is placed in a different concentration of a contaminant, such as a metal nitrate, to determine the level of tolerance of the constructed microbial mat. For example, the various solutions of metal nitrates are arranged in a series of step-wise increasing concentrations that increase in 50 mg/L increments. The lack of tolerance for a particular concentration is determined by the blanching of the cyanobacteria.

The constructed microbial mat which is in the highest concentration of the toxic material which shows no blanching is chosen. This constructed microbial mat is then transferred every 2–5 days to a solution which has increasing concentrations of the toxic material. The concentrations of these solutions increase in a step wise manner in 5 mg/L increments. Continue increasing the concentration of the toxic material until the desired level is reached.

The bacterial components of these resistant constructed microbial mats may also be selected and used to create other resistant constructed microbial mats.

EXAMPLE 3

Bioremediation of Organic Molecules

Three categories of microbes were used in the constructed microbial mat construction and six types of constructed mats were tested for their comparative capabilities of mineralizing hexadecane, a paraffin, and chrysene, a four ring polycyclic aromatic hydrocarbon (PAH).

Six treatments, or constructed microbial mat types, were used. These included laboratory-developed metal tolerant constructed microbial mats, as well as specifically constructed microbial mats. The microbial groups used for constructed mats and their major characteristics were:

1. *Oscillatoria* spp.
   Oxygenic phototrophic with heterotrophic ability.
   Nitrogen-fixing.
   Slime-generating.
2. Purple Autotrophic bacteria
   Anoxygenic phototrophic.
   Motile, seeking low oxygen zones, penetrating soils.
   Raise redox by removing $H_2S$.

3. Fermentative anaerobic group, including *Lactobacillus* spp. and *Clostridium* spp. (from ensiled grass clippings or silage):

Heterofermentative, using a variety of substrates including recalcitrant carbohydrates such as hemicellulose.

The mat construction process involved inoculating single isolates (or mixtures if fermentative bacteria) of the three microbial groups into sterile flasks with organic nutrient substrate such as ensiled grass clippings. As constructed microbial mats matured the purple autotrophic bacteria migrated under the *Oscillatoria* spp. and could be seen as red colonized areas. Grass clippings continued to degrade, indicating the presence of hemicellulose-degrading bacteria.

After all constructed microbial mats had matured into stable communities, which were tightly annealed in a gelatinous matrix, they were applied in non-sterile conditions to the petroleum distillate solutions. No attempt was made thereafter to protect the constructed microbial mat from invasion of wild microbes. However, they appeared to remain intact, maintaining the integrity of their microbial populations throughout the experiment.

Constructed microbial mats resistant to toxic concentrations of metals

1. CM+SS; Complete constructed microbial mat (CM) and sterile silage (SS):

These constructed microbial mats contained cyanobacteria (predominantly *Oscillatoria* spp.) and various species of bacteria, including purple autotrophic bacteria. All of these species of cyanobacteria and bacteria were isolated and were resistant to toxic concentrations of metal contaminants (Bi, Cd, Co, Cr, Cu, Mn, Pb, Se, Zn) using techniques as described in Example 2.

Organic nutrient substrates, such as ensiled materials, provided organic acids (carbohydrates), bacteria and some structural support for constructed microbial mat attachment and development. In this constructed microbial mat type, the silage was autoclaved (SS) to remove the effect of the ensiled bacteria.

2. CM+RS: Complete constructed microbial mat and raw silage (RS):

These constructed microbial mats contain the same soil microorganisms adapted for metal tolerance as No. 1 in addition to non-sterile, or raw, silage. Therefore, ensiled bacteria were present.

3. OSPB+SS: *Oscillatoria* spp. (OS), purple autotrophic bacteria (PB) and sterile silage:

These constructed microbial mats contain commercially obtained *Oscillatoria* spp. and purple autotrophic bacteria. Autoclaved silage was added.

4. OSPB+RS: *Oscillatoria* spp., purple autotrophic bacteria and raw silage:

These constructed microbial mats contain the same microorganisms as No. 3 in addition to non-sterile silage. Therefore, ensiled bacteria were present.

5. OS+SS; *Oscillatoria* spp. and sterile silage:

These constructed microbial mats contained only the *Oscillatoria* spp. as used in Nos. 4 and 5, in addition to sterile silage.

6. OS+RS: *Oscillatoria* spp. and raw silage:

These constructed microbial mats contain only the *Oscillatoria* spp. as used in Nos. 4 and 5, in addition to raw silage.

These codes are used to identify the various constructed microbial mats in the figures.

A similar series of test tubes were set up to test the mineralization capabilities of only purple autotrophic photosynthetic bacteria, a major component of microbial mats.

The following petroleum hydrocarbons were tested with each of the above constructed microbial mats:

1) Hexadecane, a straight-chain alkane, and
2) Chrysene, a high molecular weight polycyclic aromatic hydrocarbon (PAH), were selected as representative constituents of petroleum.

Both hydrocarbons were either $^{14}$C-labeled (chrysene: specific activity=6.3 mCi/mmol, Amersham Corp., Arlington Heights, Ill. and hexadecane: specific activity=1.2 mCi/mmol. Sigma Chemical Co., St. Louis, Mo.) or unlabeled.

Constructed microbial mats contain both photosynthesizing and heterotrophic microorganisms both of which could be capable of degrading the petroleum hydrocarbons. Some of the photosynthesizers also are effective heterotrophs. Therefore, the experimental design included a lighted and a dark series for each treatment (constructed microbial mat type) in an attempt to isolate differences in mineralization due to the provision of lack of light.

A total of 104 test tubes were used for all of the six constructed microbial mat types under lighted and dark regimens. These included: triplicate experimental tubes (with a live constructed microbial mat plug) for each constructed microbial mat type; one additional tube containing the $^{14}$C-labeled compound plus 25 mg/L of unlabeled chrysene or hexadecane for each constructed microbial mat type; one control tube without constructed microbial mat and spiked with the $^{14}$C-labeled compound for each hydrocarbon types; and one controlled tube with a microbial mat killed with 1 mL of 0.1M $HgCl_2$ and spiked with the $^{14}$C-labeled compound for each hydrocarbon type.

An additional 12 test tubes were used to test the mineralizing capabilities of purple autotrophic bacteria. One milliliter of the culture was used to set up a series in the same fashion as the microbial mat series.

Tests for significant differences in degradation among constructed microbial mat treatments were performed using one-way analysis of variance and protected t-tests (GB-Strat Professional Statistics and Graphics, Dynamic Microsystems, Inc., Silver Springs, Md.).

Only one hydrocarbon was added to each tube. Additions of the $^{14}$C-labeled compounds to the test tubes were intended to spike the media at a level greater than 4800 dpm/mL. Therefore, each tube was spiked with 144,000 dpm/mL of $^{14}$C-labeled hexadecane (=12.259 μg) or chrysene (=2.348 μg). In tubes containing an additional 25 mg/L of hydrocarbon, this amounted to an additional 375 μL of hexadecane or 375 μg of chrysene dissolved in methylene chloride.

Procedure

Pieces of constructed microbial mat were separated, weighed (wet weight) and added to sterile borosilicate test tubes. One milliliter of purple autotrophic bacteria culture was added to its respective tubes. The appropriate $^{14}$C-labeled or unlabeled hydrocarbon was added and final tube volumes were adjusted to 15 mL through the addition of Allen/Arnon Modified Media (Allen & Arnon, 1955).

A 7-mL scintillation vial KOH trap containing 1 mL of 0.3M KOH was suspended inside each tube over the surface of the media using a piece of Teflon tape. This latter was held firmly in place by a Teflon tape-coated cork stopper. Teflon does not react with hydrocarbons (Bauer & Capone, 1985).

Lighted tubes were held under 24 hour mixed fluorescent and incandescent lighting. "Dark" tubes were kept in the same location and covered with two layers of aluminum foil. Ambient temperature ranged from 28°–32° C.

Samples of the radioactive tube culture media (1 mL) were drawn and placed into a 7-mL scintillation vial at 0 and 28 days. At 1, 7, 14 and 28 days, the KOH trap from each flask was removed (and replaced at 1, 7, 14 days). Five mL of scintillation fluid (Ultima Gold, Packard Chemical Co., Meriden, Conn.) were added to each scintillation vial and counted for 10 minutes on a liquid scintillation counter (Packard Bell). At Day 28, the pH of each test tube media was lowered to <4.5 with $H_2SO_4$ in order to drive $CO_2$ from the media and into the KOH trap.

Hexane was used to wash $^{14}CO_2$ from selected constructed microbial mat samples. These were counted by the scintillation counter to obtain gross information on $^{14}C$ incorporation.

Results

Figure 8A:
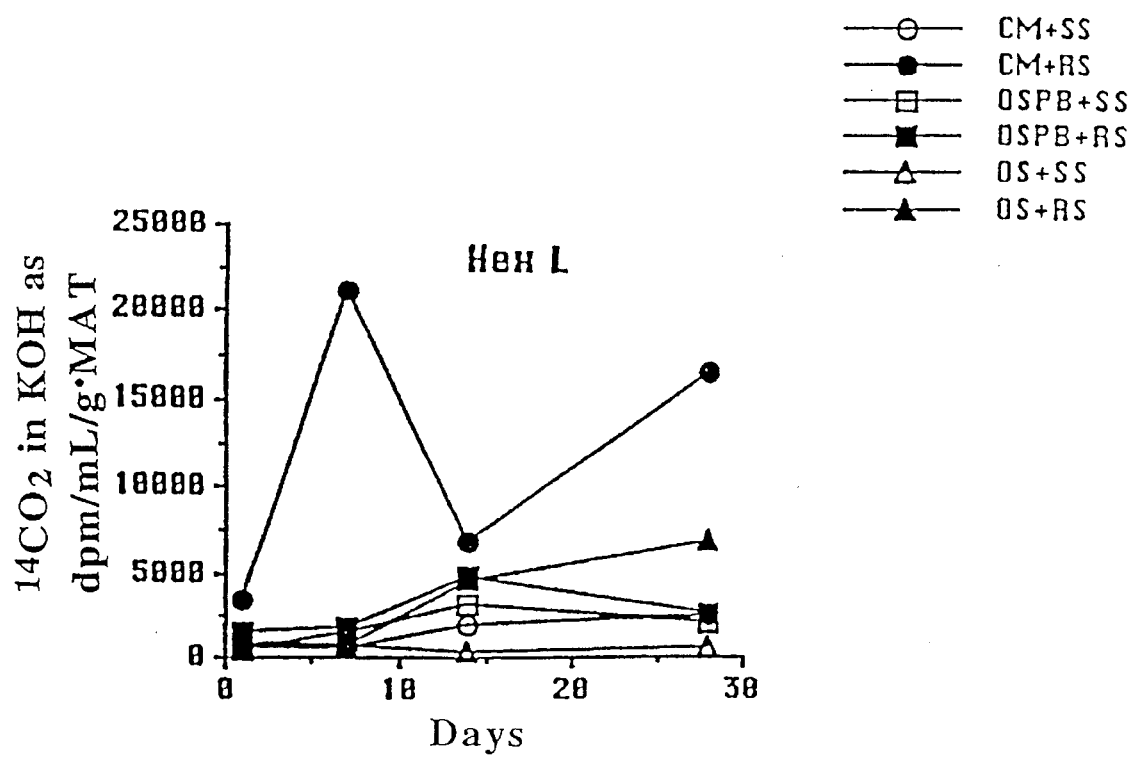
FIG. 8 shows degradation of organic contaminants, hexadecane and chrysene, by constructed microbial mats with differing experimental components, and under light or dark conditions. The normalized (dpm/mL/g of mat) KOH trap readings (dpm/mL) are plotted relative to days. 8a shows degradation of hexadecane under light conditions. 8b shows degradation of hexadecane under dark conditions. 8c shows degradation of chrysene under light conditions. 8d shows degradation of chrysene under dark conditions. CM+SS, constructed microbial mat (CM) and sterile silage (SS); CM+RS; constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage. The data represent a triplicate mean and is not cumulative.
Figure 8B:
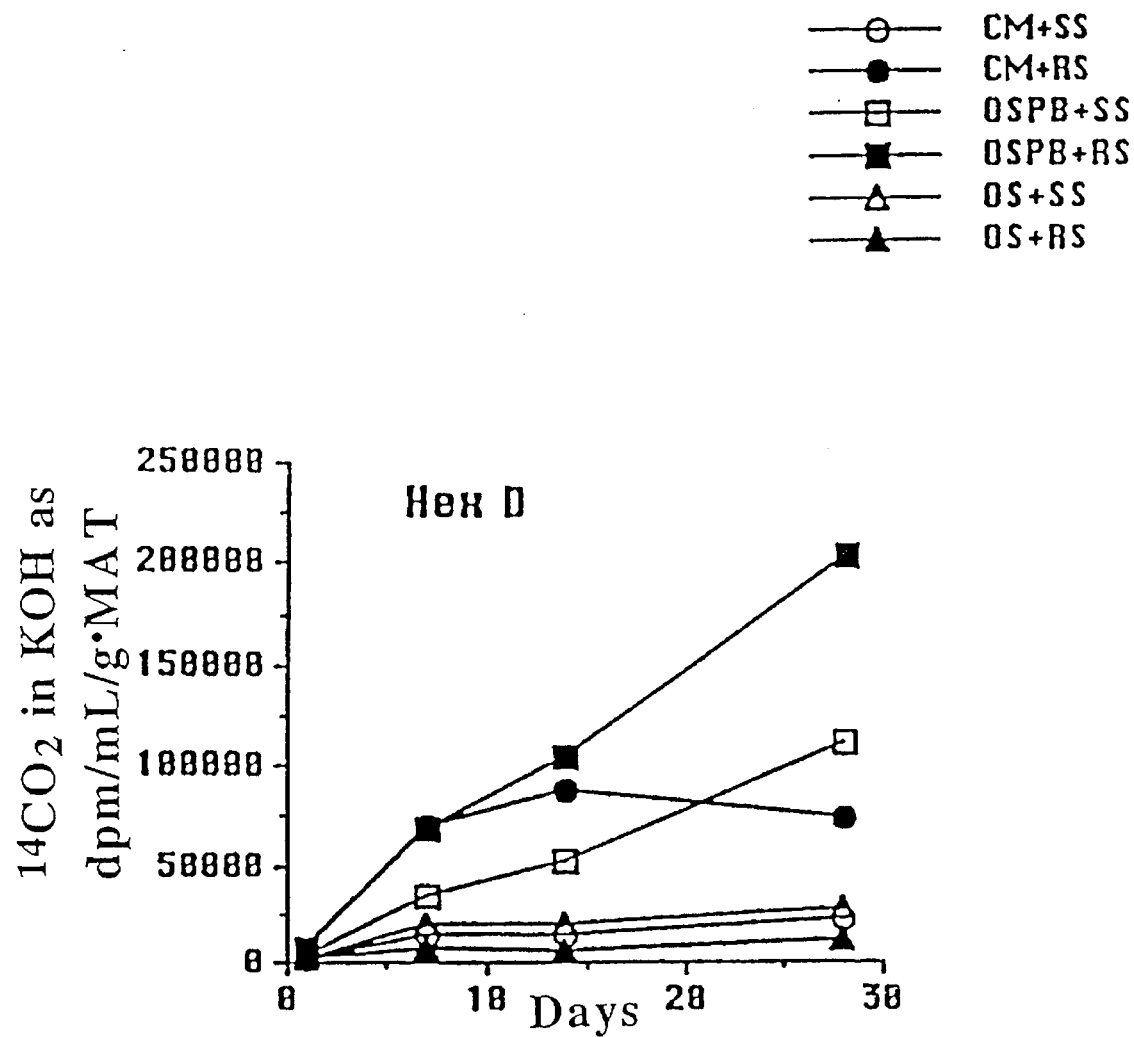
Figure 8C:
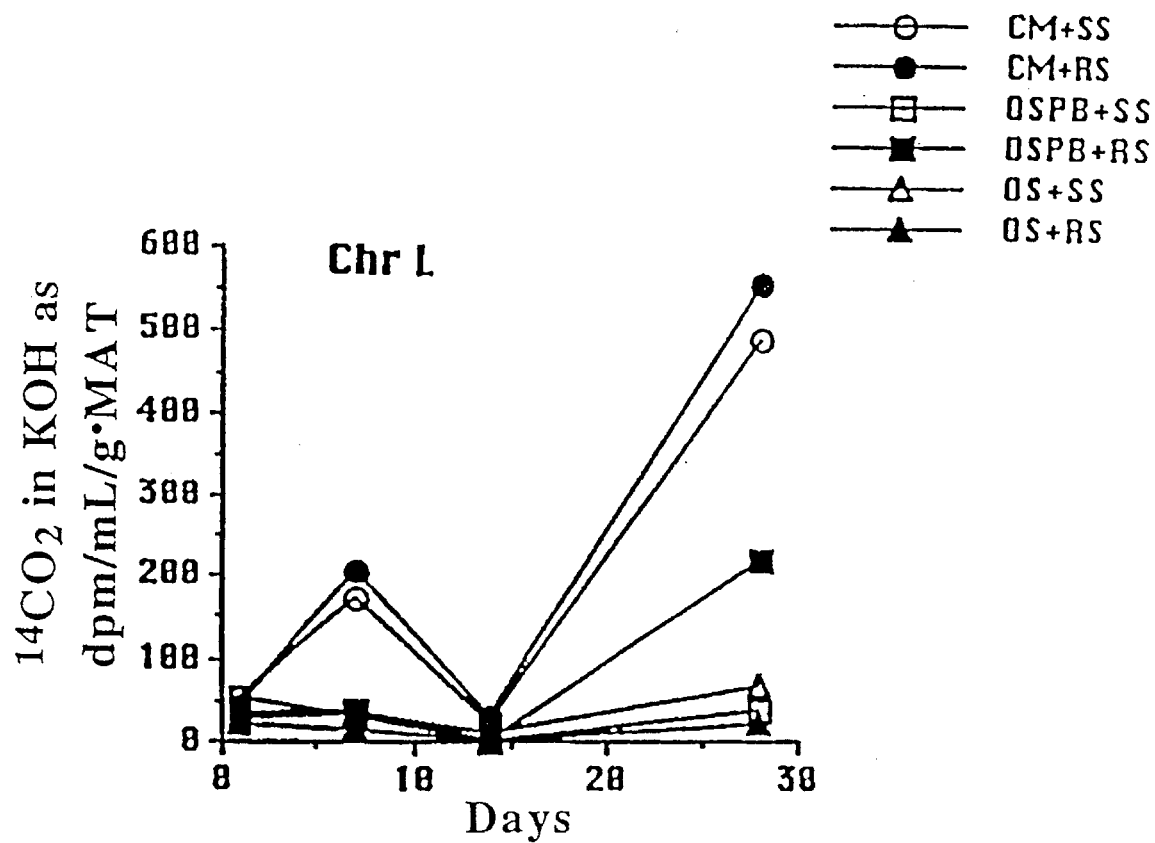
Figure 8D:
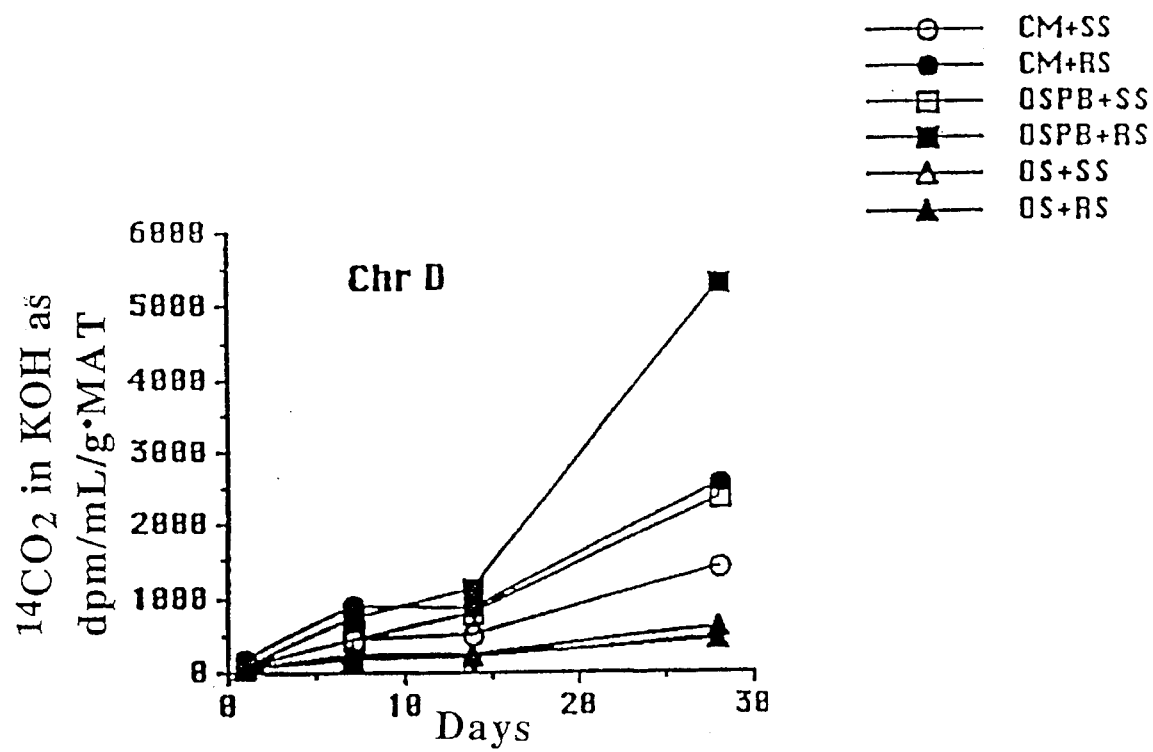

Results are reported separately for each constructed microbial mat of the six constructed microbial mat types over the 28-day period. FIG. 8 shows degradation of organic contaminants, hexadecane and chrysene, by constructed microbial mats with differing experimental components, and under light or dark conditions. FIGS. 8a–d shows KOH trap $^{14}C$-levels in dpm/mL and normalized for the initial microbial mat weight. FIG. 8a shows degradation of hexadecane under light conditions. FIG. 8b shows degradation of hexadecane under dark conditions. FIG. 8c shows degradation of chrysene under light conditions. FIG. 8d shows degradation of chrysene under dark conditions. CM+SS, Complete constructed microbial mat (CM) and sterile silage (SS); CM+RS; Complete constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage. The data represent a triplicate mean and is not cumulative.

FIG. 9 shows KOH trap dpm/mL values converted to ng of hydrocarbon mineralized in ng/h for the first 24 hours (FIG. 9) or ng/day (FIG. 10).

Figure 9A:
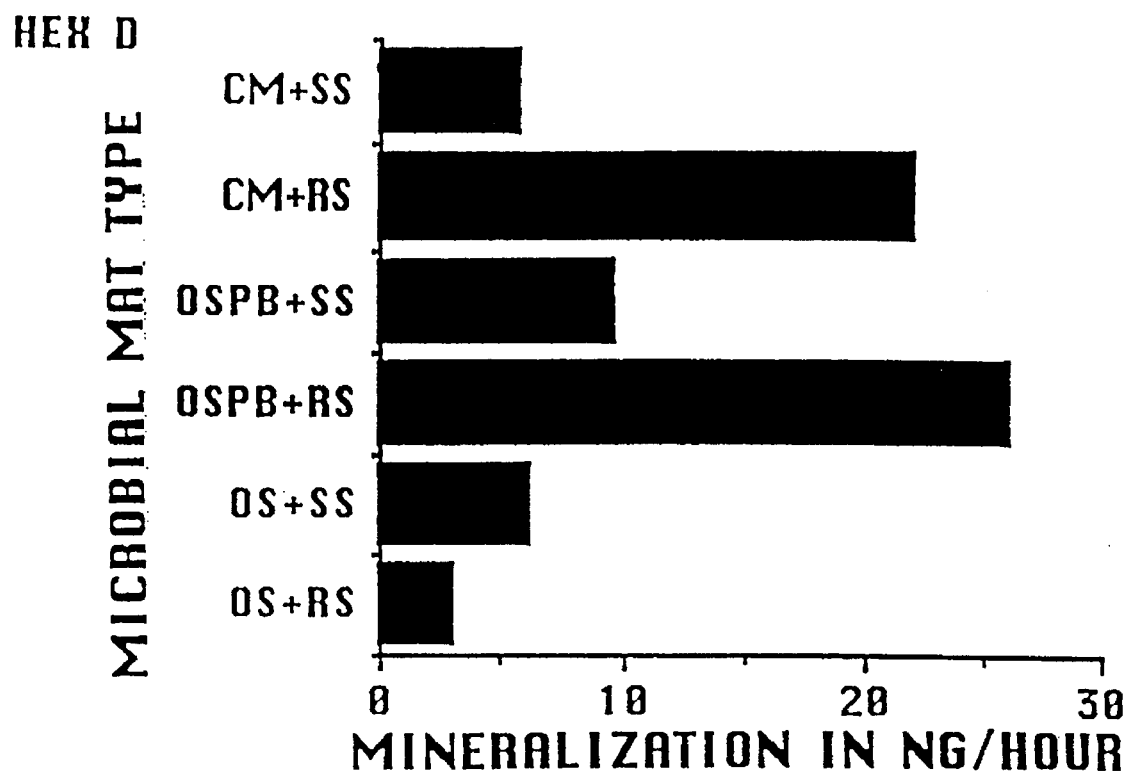
FIGS. 9a–d shows KOH trap dpm/mL values converted to ng of hydrocarbon mineralized in ng/h for the first 24 hours.
Figure 9B:
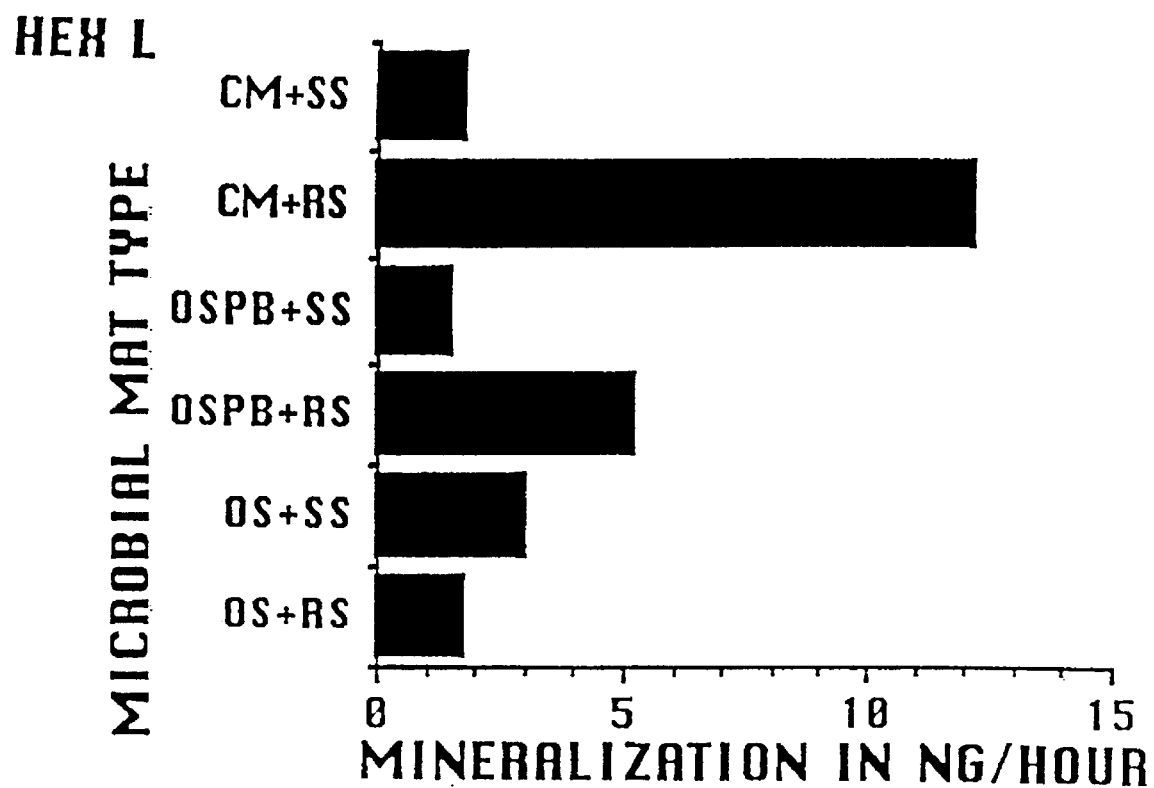
Figure 9C:
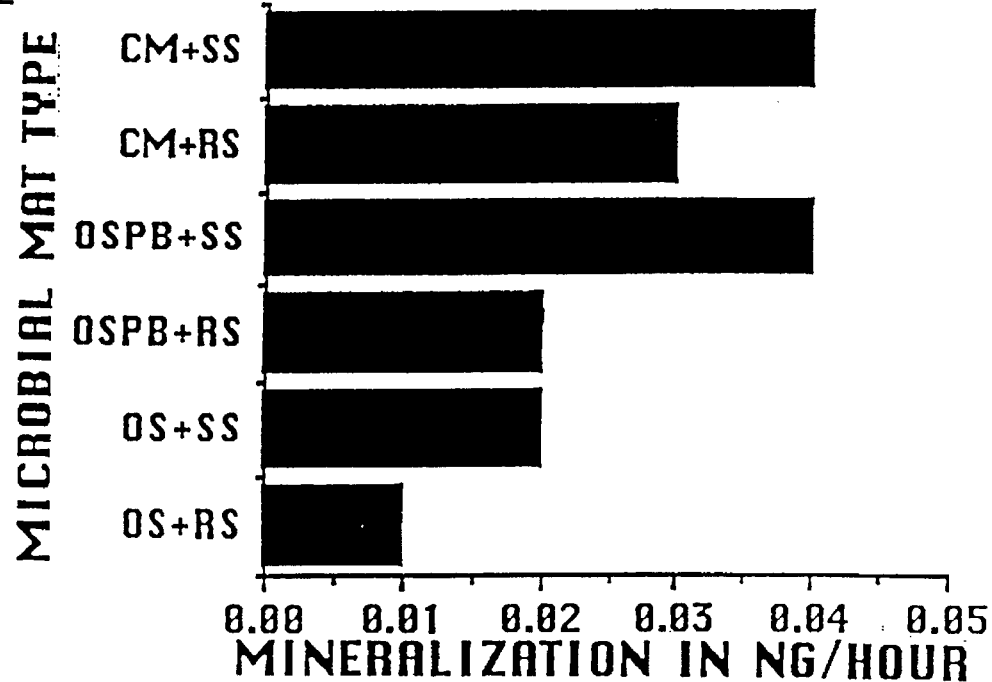
Figure 9D:
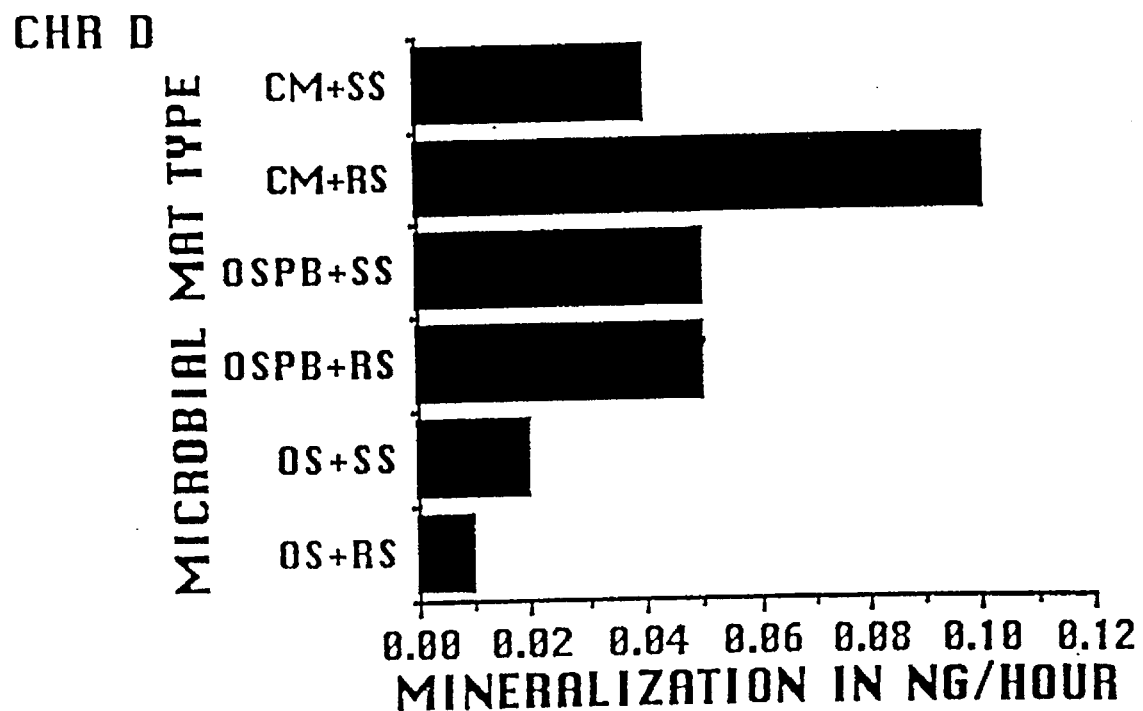

FIGS. 9a–d shows KOH trap dpm/mL values converted to ng of hydrocarbon mineralized in ng/h for the first 24 hours. FIG. 9a shows mineralization of hexadecane, in ng/hour under light conditions. FIG. 9b shows mineralization of hexadecane, in ng/hour under dark conditions. FIG. 9c shows mineralization of chrysene, in ng/hour under light conditions. FIG. 9d shows mineralization of chrysene, in ng/hour under dark conditions. CM+SS, Complete constructed microbial mat (CM) and sterile silage (SS); CM+RS; Complete constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage. The data represent a triplicate mean and is not cumulative.

Figure 10A:
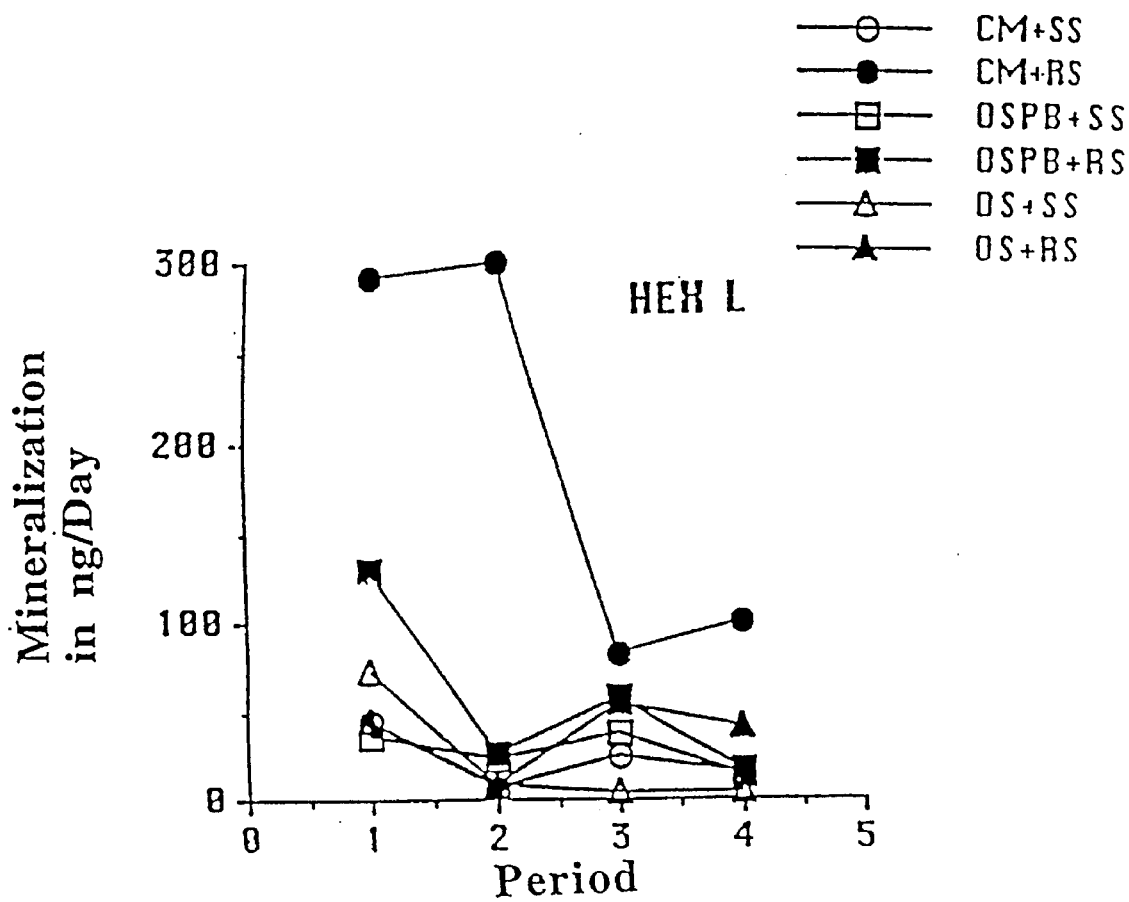
FIGS. 10a–d shows KOH trap dpm/mL values converted to ng of hydrocarbon mineralized in ng/day. The daily rates were calculated for: Period 1=first 24 hours; Period 2=data from the subsequent 6 days; Period 3=data from the second week; Period 4=data from the third and fourth weeks combined.
Figure 10B:
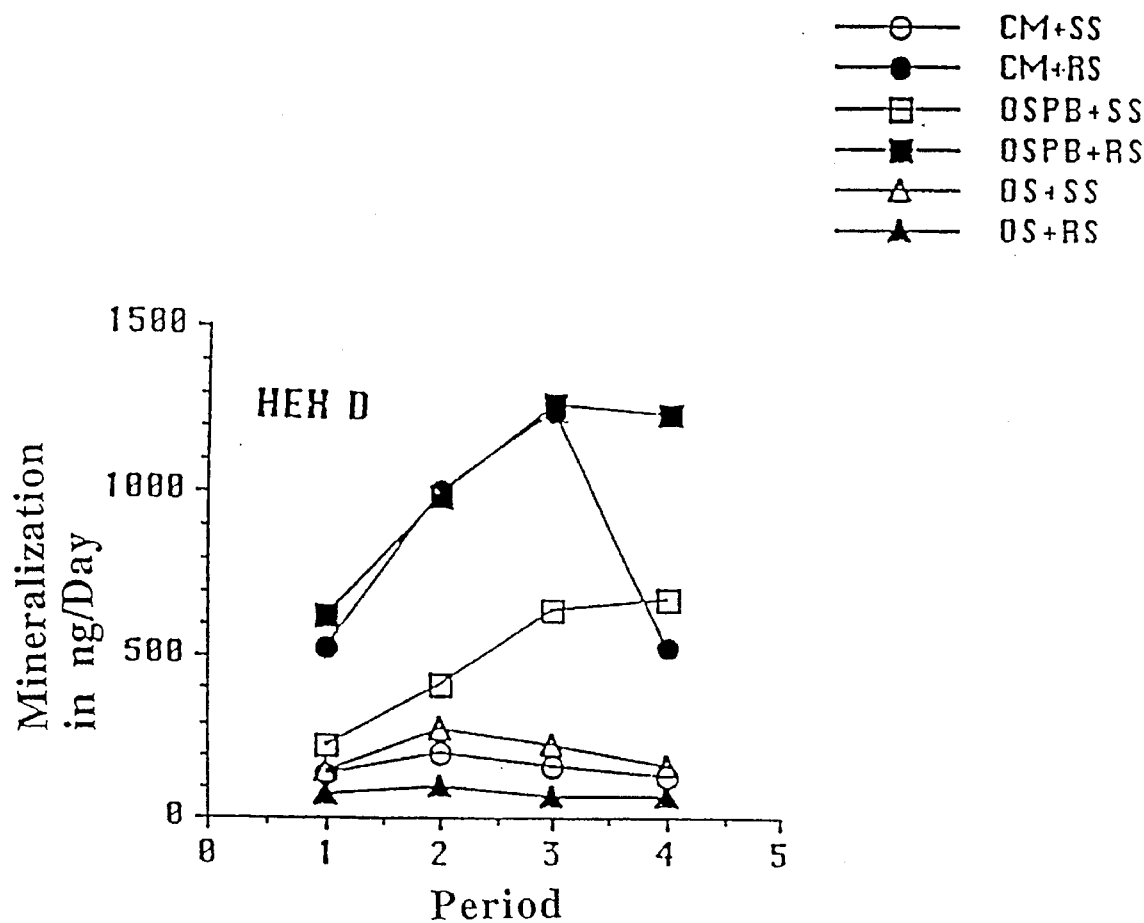
Figure 10C:
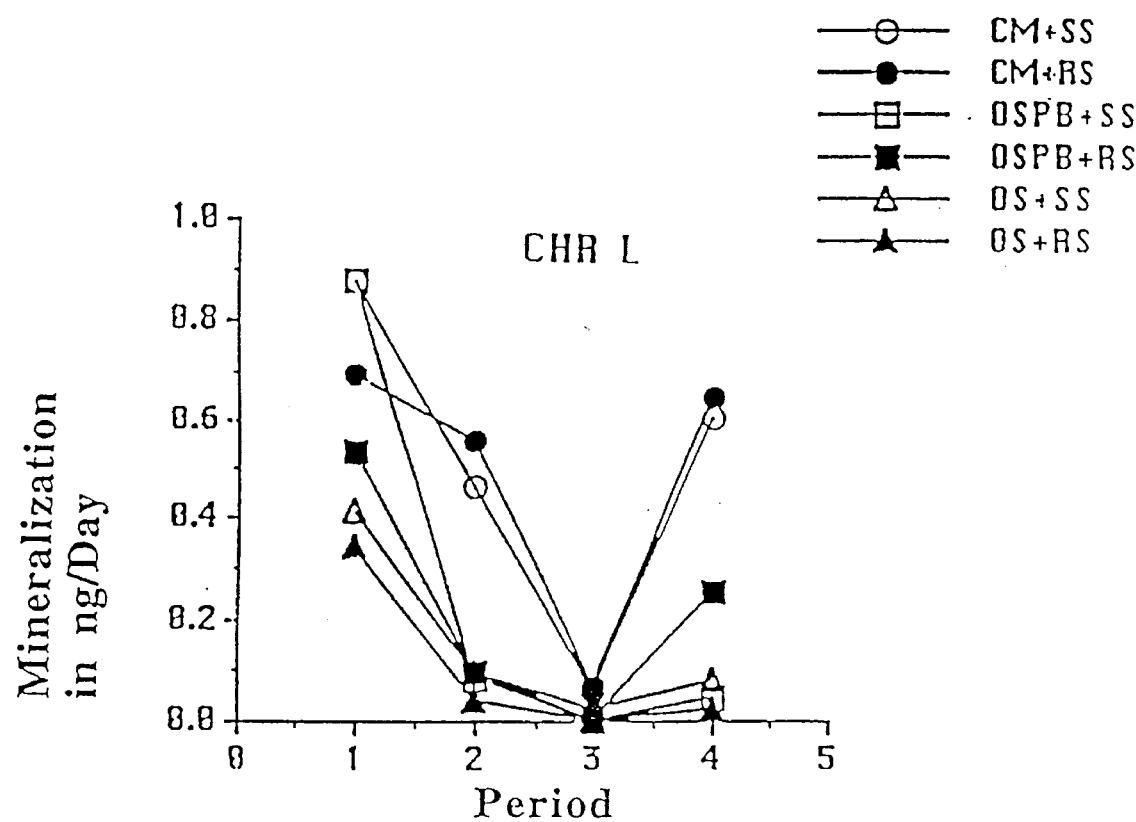
Figure 10D:
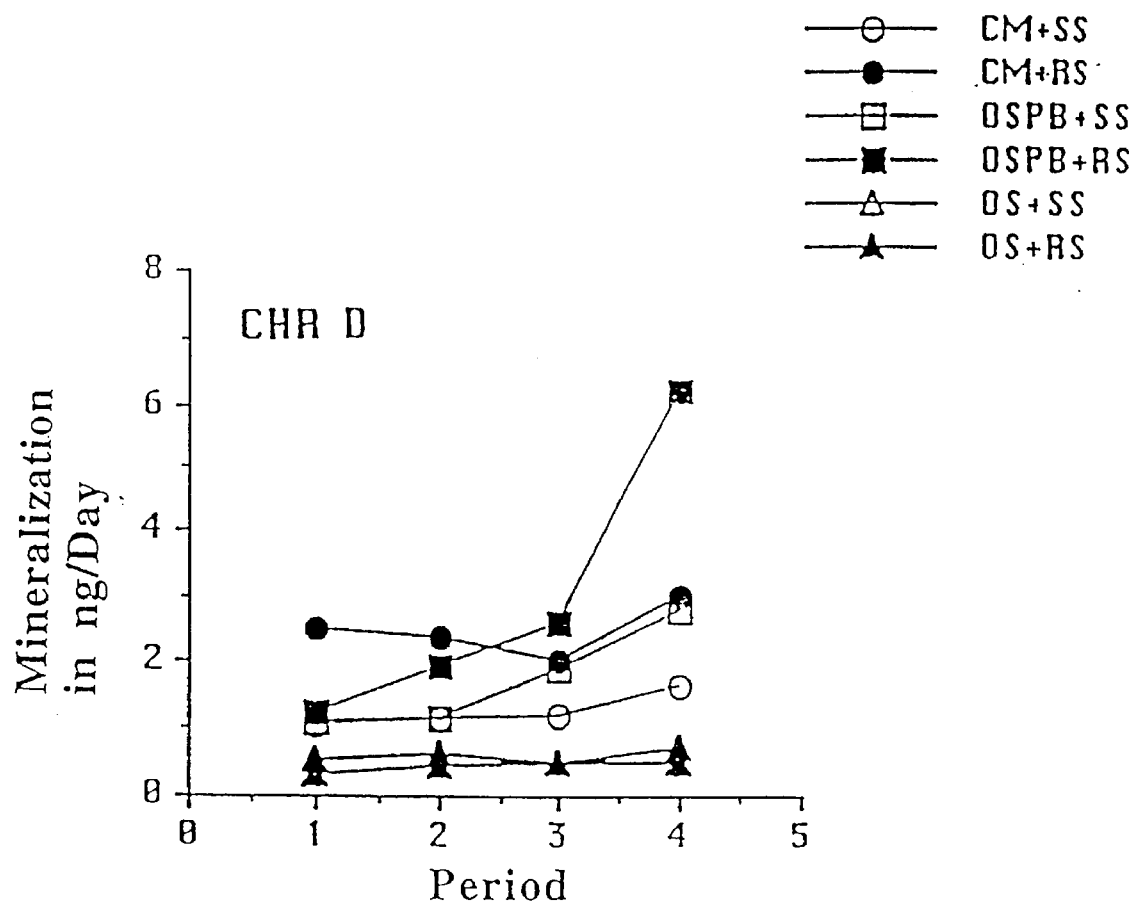

FIGS. 10a–d shows KOH trap dpm/mL values converted to ng of hydrocarbon mineralized in ng/day. The daily rates were calculated for: Period 1=first 24 hours; Period 2=data from the subsequent 6 days; Period 3=data from the second week; Period 4=data from the third and fourth weeks combined. FIG. 10a shows mineralization of hexadecane, in ng/day under light conditions. FIG. 10b shows mineralization of hexadecane, in ng/day under dark conditions. FIG. 10c shows mineralization of chrysene, in rig/day under light conditions. FIG. 10d shows mineralization of chrysene, in ng/hour under dark conditions. CM+SS, constructed microbial mat (CM) and sterile silage (SS); CM+RS; constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage. The data represent a triplicate mean and is not cumulative.

Figure 11A:
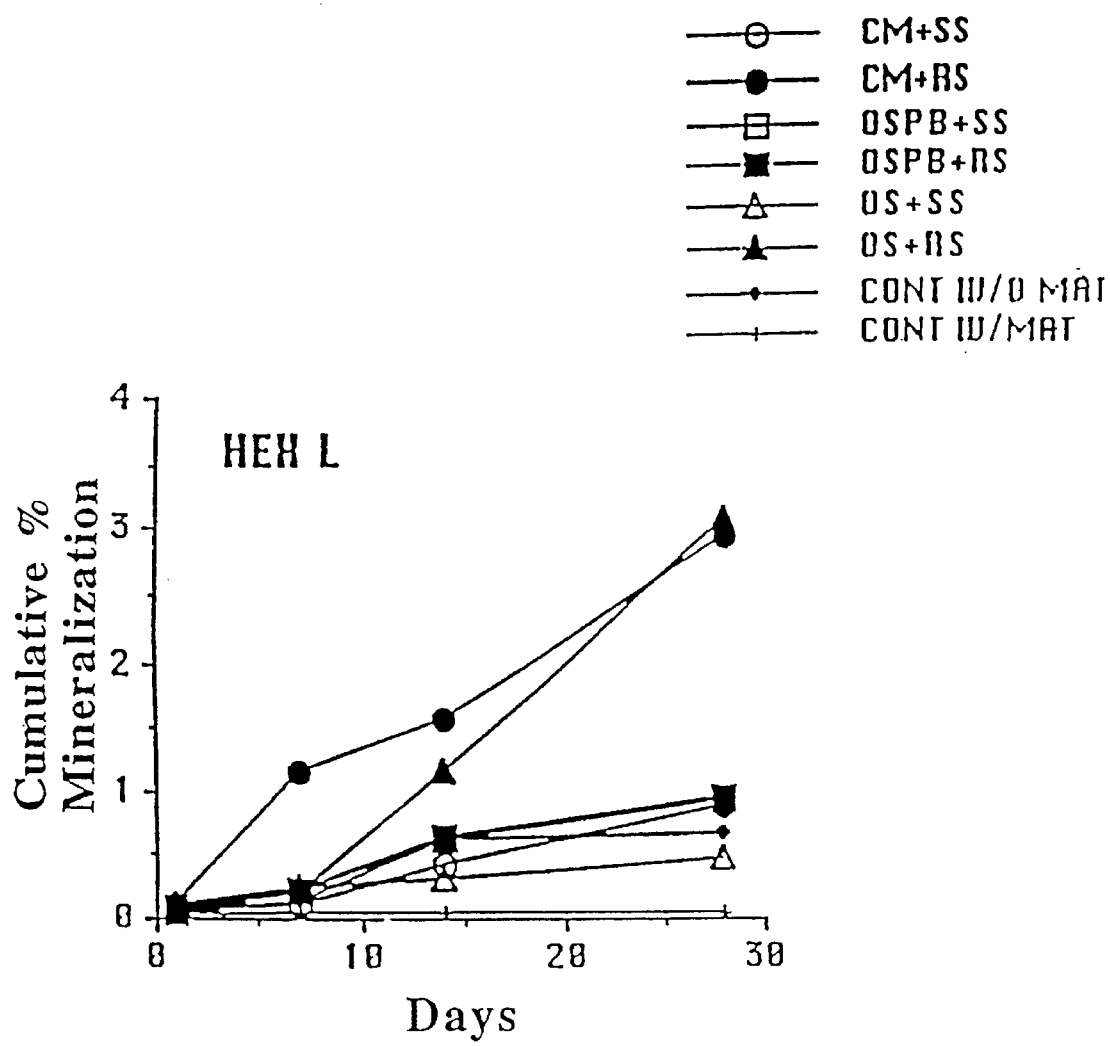
FIGS. 11a–d shows the mineralization rate of hexadecane or chrysene calculated as a percentage of the initial amount of the hydrocarbon (hexadecane or chrysene) spiked into each tube. Cumulative percent mineralization is based on unnormalized KOH trap reading (dpm/mL). The data represent a triplicate mean.
Figure 11B:
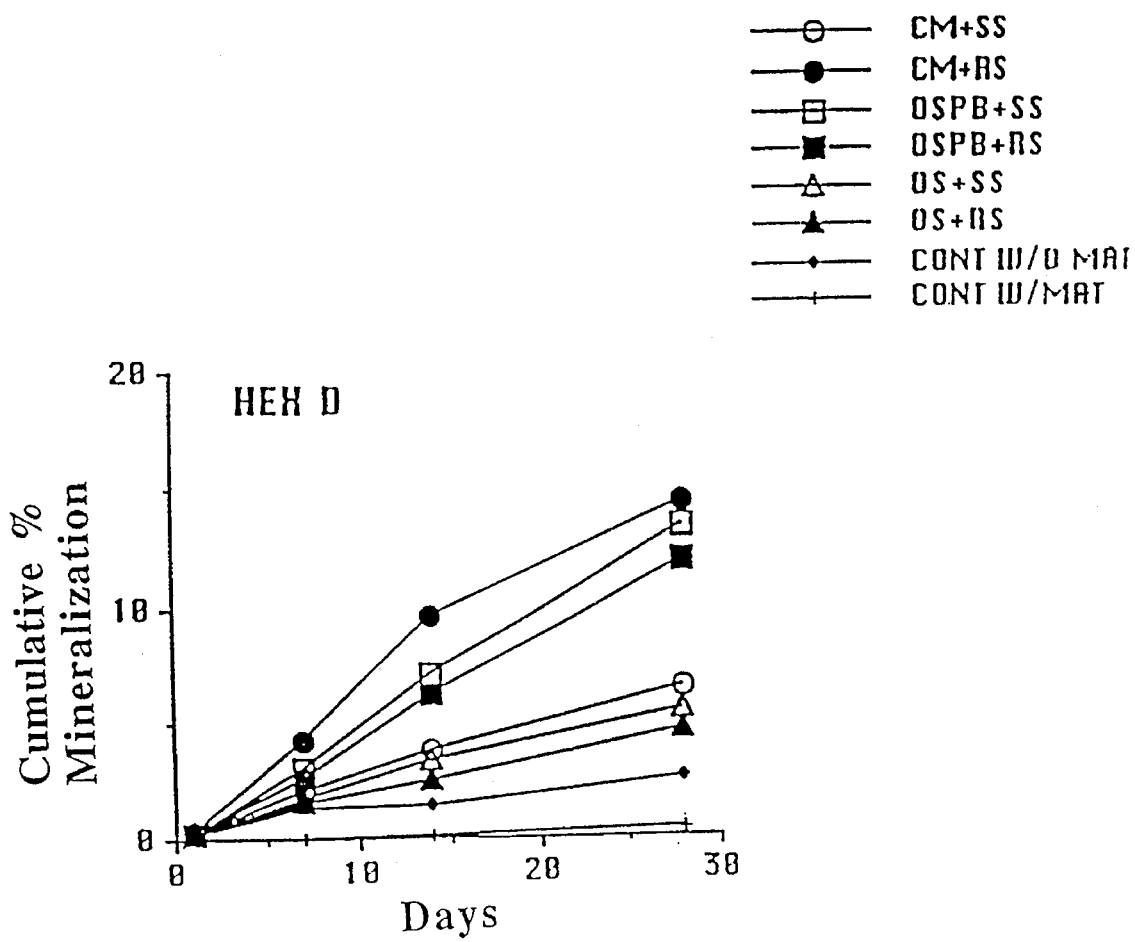
Figure 11C:
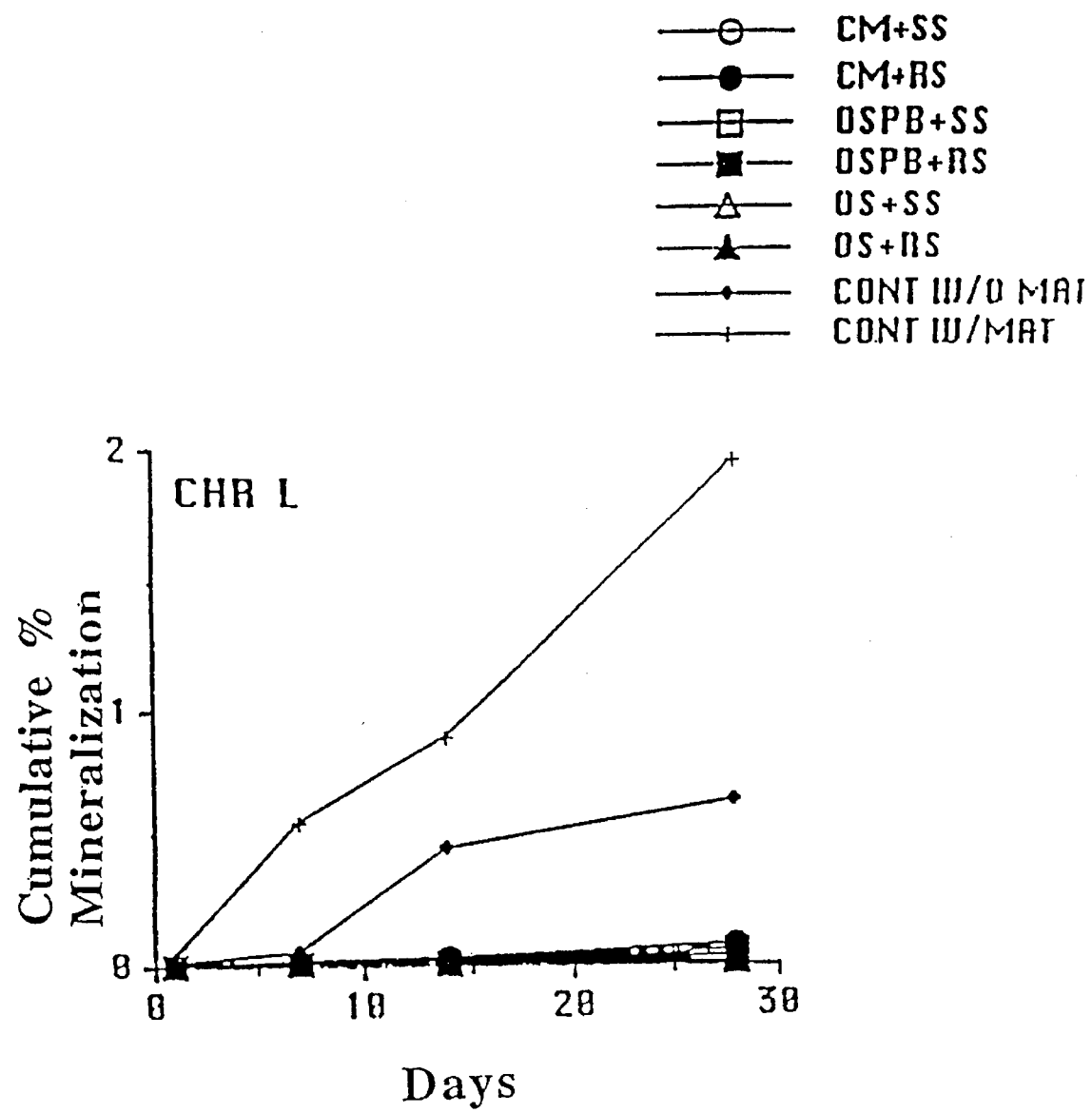
Figure 11D:
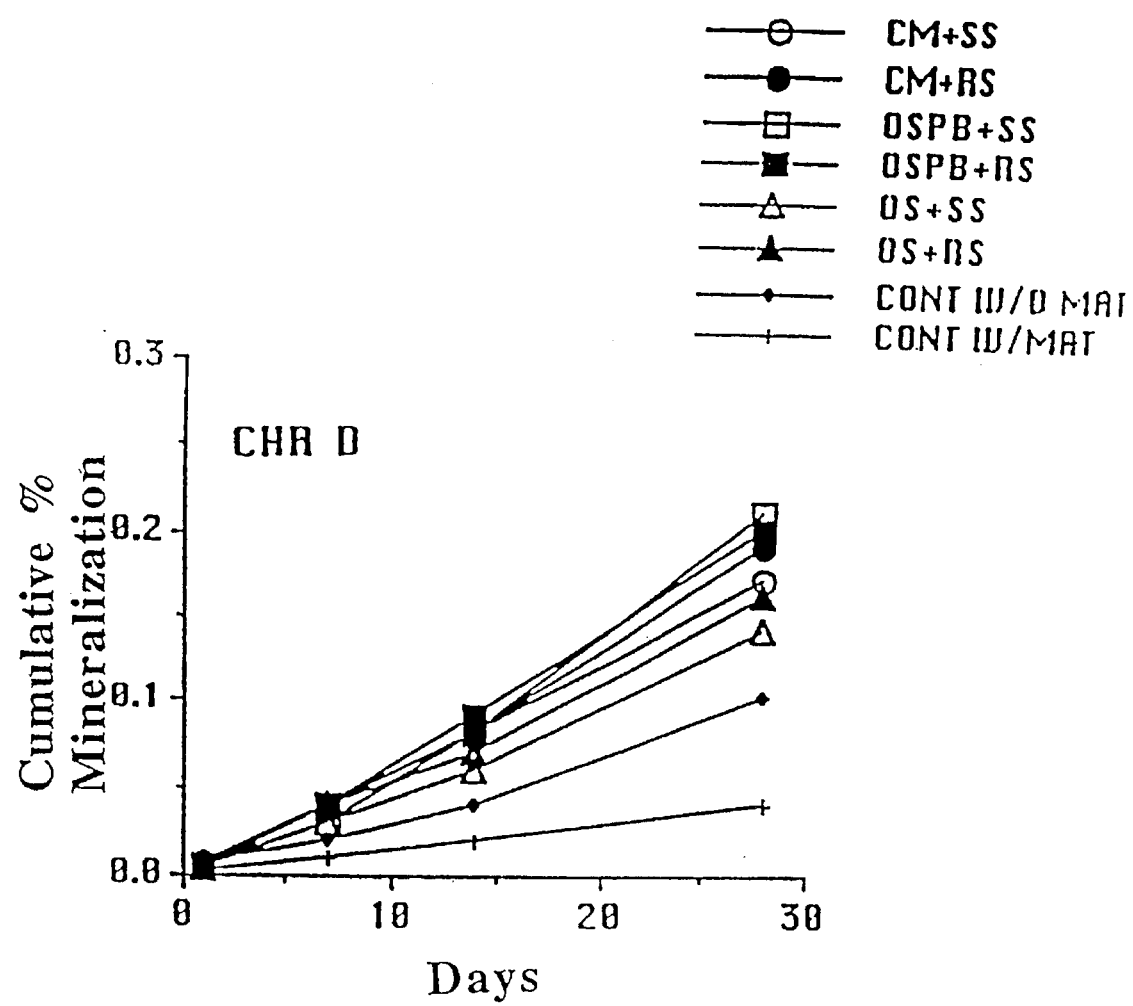

FIGS. 11a–d shows the mineralization rate of hexadecane or chrysene calculated as a percentage of the initial amount of the hydrocarbon (hexadecane or chrysene) spiked into each tube. Cumulative percent mineralization is based on unnormaiized KOH trap reading (dpm/mL). The data represent a triplicate mean. FIG. 11a shows the mineralization rate of hexadecane under light conditions. FIG. 11b shows the mineralization rate of hexadecane under dark conditions. FIG. 11c shows the mineralization rate of chrysene under light conditions. FIG. 11d shows the mineralization rate of chrysene under dark conditions. CM+SS, constructed microbial mat (CM) and sterile silage (SS); CM+RS; constructed microbial mat and raw silage (RS); OSPB+SS; *Oscillatoria* spp. (OS), purple autotrophic bacteria (PB) and sterile silage; OSPB+RS; *Oscillatoria* spp., purple autotrophic bacteria and raw silage; OS+SS; *Oscillatoria* spp. and sterile silage; OS+RS; *Oscillatoria* spp. and raw silage.

Neither the $^{14}C$-labeled hexadecane or chrysene, nor tubes containing an additional 25 mg/L of hexadecane or chrysene was toxic to the microbial mat. Under lighted conditions, constructed microbial mat wet weight increased an average of 103.3% (s.d.=68.4 over the treatment means) in hexadecane and 140.6% (s.d.=107.0 over the treatment means) in chrysene. Mat wet weights generally increased little, or even decreased, under dark conditions in hexadecane (mean=7.25%, s.d.=47.3 over the treatment means) and chrysene (mean=26.0%, s.d.=25.7 over the treatment means).

Despite the intended spiking rate of >4800 dpm/mL hexadecane showed lower counts in the 1-mL media samples drawn at the moment of initial spiking (lighted series mean=755.01 dpm/mL, s.d.=354.90; and dark series mean=2803.38 dpm/mL, s.d.=658.60).

The initial counts of the CM+RS treatment were comparable to all other treatments, while under dark conditions OSPB+RS treatment showed the greatest degradation (significant at p<0.01 or 0.05 compared to CM+SS, OS+SS and OS+RS) With chrysene, degradation in lighted and dark condition,, followed the same trend (CM+RS constructed microbial mat under light; OSPB+RS constructed microbial mat in dark) though these results were not statistically significant. All *Oscillatoria* spp. treatments (OS+RS and OS+SS) had the lowest counts of all (except OS+RS Hex L). When an additional 25 mg/L of unlabeled hydrocarbon was added as excess nutrients to the test tube media, $^{14}CO_2$ counts were usually lower, but the same general trends persisted (data not shown).

Mineralization rate calculations parallel $^{14}CO_2$ values. The mineralization rates were more than 150-fold greater for hexadecane compared to chrysene during the first 24 hours Examining the dark series data, for both hexadecane and chrysene, the rate of mineralization steadily increased through the four-week experiment. During this time, hexadecane was degrading at a rate >400-fold over chrysene. During the first 24 hours, experimental values ranged from 0.01–0.04 ng/h for chrysene lighted series to 1.5–12.2 ng/h for hexadecane lighted series. Dark series values for the same time period ranged from 0.01–0.10 ng/h for chrysene and 3.0–27.6 ng/h for hexadecane. Daily mineralization rates, by Day 28 ranged from 0.022–0.644 ng/day in the chrysene lighted series to 3.6–100.4 ng/day in the hexadecane lighted series. Dark series values for the same time period ranged from 0.494–2.998 ng/day for chrysene and 63.2–1232.8 ng/day for hexadecane.

During 28 days, the percent mineralization of the entire originally spiked amount was significantly greater for hexadecane compared to chrysene (FIG. 4). Final lighted series experimental values ranged from 0.01–0.08% for chrysene and 0.47–3.07% for hexadecane. Final dark series experimental values ranged from 0.14–0.21% for chrysene and 4.65–14.29% for hexadecane.

At Day 28, hexane-washed samples of constructed microbial mat were examined for evidence of incorporation into microbial mat biomass of $^{14}CO_2$ generated by the mineralization of hexadecane or chrysene. High levels of $^{14}CO_2$ were detected in all samples. Purple autotrophic bacteria also degraded hexadecane and chrysene similarly under lighted and dark conditions. Hexadecane was again degraded at a much greater rate than chrysene.

While there is some information to suggest the potential for cyanobacterial degradation of hydrocarbons, these experiments show that a constructed microbial mat having purple autotrophic bacteria in combination with a cyanobacteria ensiled vegetation produce superior results in mineralization. By the end of the experiment, it was notable that the addition of organic nutrient substrate such as silage and its accompanying microbial flora (raw silage contains *Lactobacillus* spp. and *Clostridium* spp.) usually significantly enhanced hydrocarbon mineralization. The most effective mineralizers of both hexadecane and chrysene under lighted conditions were the complete constructed microbial mats containing predominately *Oscillatoria* spp. and purple autotrophic bacteria.

Without the interference of $^{14}CO_2$ uptake via photosynthesis, the dark experimental series are the most reliable data. Under this latter scenario, the constructed mat of *Oscillatoria* spp. and purple autotrophic bacteria was the most effective mineralizer of both hexadecane and chrysene.

EXAMPLE 4

Bioremediation of Metal Contaminated Water

Figure 12:
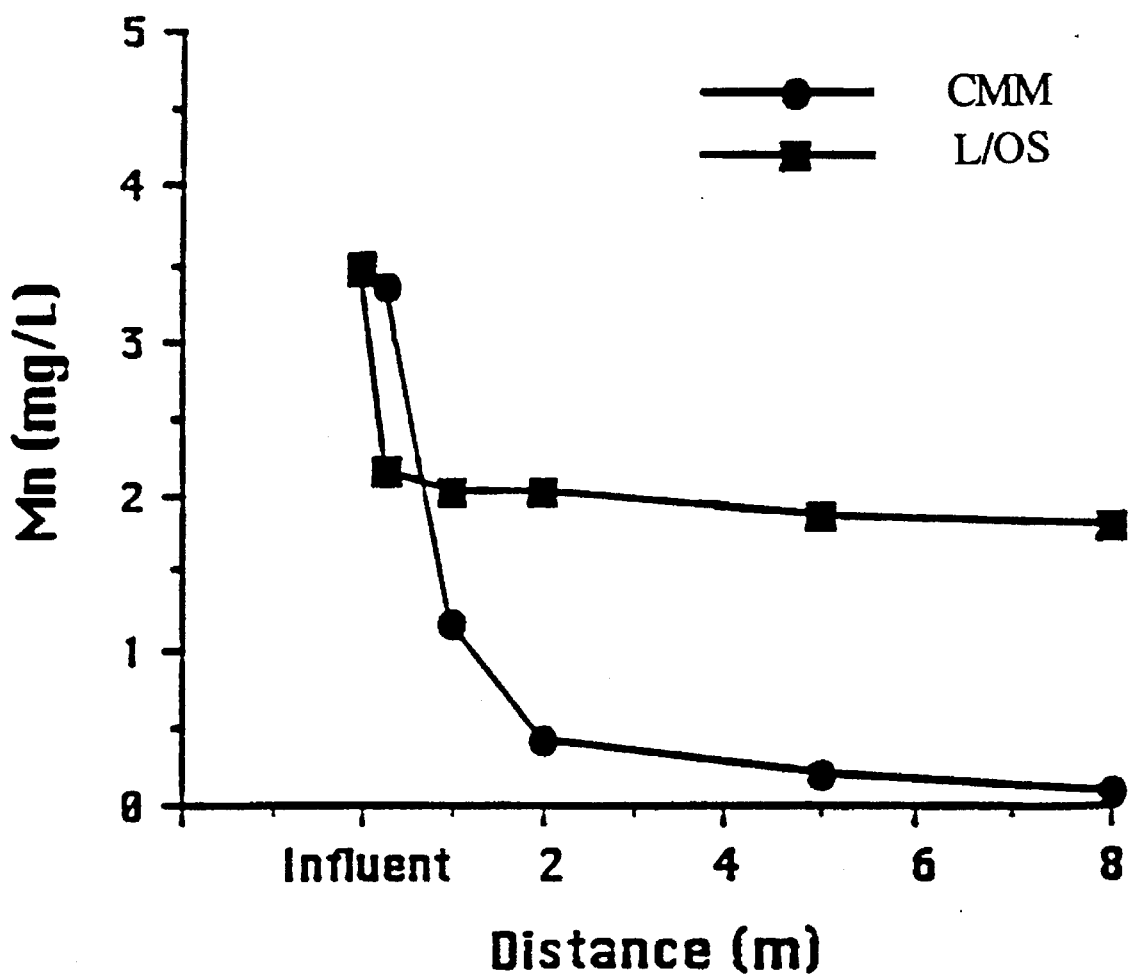
FIG. 12 shows a graph of continuous flow treatment of acid-mine drainage by constructed microbial mat with green algae support structure. Constructed microbial mat is significantly more effective in removing manganese (Mn) than the limestone substrate with a cover of Oscillatoria pond (L/Os). The constructed microbial mat pond is able to meet U.S. Environmental Agency standards of <2 mg/L within one meter of the influent pipe.

Constructed microbial mats were produced as described in Example 1, with microbial species which were adapted for high concentrations of metals as described in Example 2. In a field pond application of these constructed microbial mats in the sequester of metal-contaminated mining water, a floating constructed microbial mat (1–2 cm thick), composed of *Oscillatoria,* immobilized on filamentous green algae, grew rapidly in the pond after addition of constructed microbial mat inocula. A secondary constructed microbial mat also covered the limestone at the bottom. Thus the metal-contaminated water flowed between the two constructed microbial mats. Approximately six weeks were required to establish a full pond constructed microbial mat cover, but effective metal removal began in the early stages of constructed microbial mat growth. FIG. 12 shows the metal removal profiles in the ponds at flow rates of 2–5 L/min.

FIG. 12 shows a graph of continuous flow treatment of acid-mine drainage by constructed microbial mat with green algae support structure. The constructed microbial mat is significantly more effective in removing manganese (Mn) than the limestone substrate with a cover of *Oscillatoria* pond (L/Os). The constructed microbial mat pond is able to meet US Environmental Agency standards of <2 mg/L within one meter of the influent pipe.

Metals (Mn and Fe) were effectively removed after the inflow water had flowed a distance of approximately 1–2 m through the pond. All sampling points beyond that distance showed metal concentrations <1.2 mg/L. Patches of red colonies indicated the presence of purple autotrophic bacteria in and around the constructed microbial mat. There is no evidence of metal deposit on the top surface of the constructed microbial mat. High redox conditions in the water column, mediated by the photosynthetic processes of these two microbial groups, likely resulted in the rapid deposit of the Mn. It has remained functional for 5 months in depositing approximately 2.6 g of $Mn/M^2$/day.

Redox and dissolved oxygen levels were high during the light period and pH levels ranged from 6.4–7.7. Even after 10 h of darkness, oxygen levels remained at 6 mg/L in some regions of the constructed microbial mat pond. During the photosynthetic period bubbles of oxygen become entrapped in the slimy matrix that typically binds the constructed microbial mat. Apparently this sequestered oxygen remains available throughout the night This is to be expected since cyanobacteria are unusual in that the have limited ability to utilize organic substrates for energy production in the dark, thus the oxygen consumption remained low.

Although the conditions of high oxygen and redox may be central to the deposit of Mn oxides, other factors may be functional as well. Flocculents were identified in the water column under the constructed microbial mat. Laboratory research showed that specific bioflocculants were released by the constructed microbial mat in response to the presence of $Mn^{+2}$. These materials carried surface charges ranging from −58.8 to −65.7 mV. The charges changed to +1.8 in the presence of divalent metal, indicating metal-binding to the bioflocculant.

Although metals which are adsorbed, precipitated or complexed can be released back into solution in an equilibrium response, no such fluctuations have been detected thus far during a four-month experimental period. Conditions of neutral pH with high dissolved oxygen and redox levels (mediated by the biochemistry of the constructed microbial mat ecosystem) favor the chemical precipitation of Mn oxides and Fe hydroxides. These, in turn, act as reservoirs for additional metal deposit.

The potential bioavailability of metals is favored by increases in acidity, reducing power and salinity. Constructed microbial mats, containing *Oscillatoria* and purple autotrophic bacteria, would tend to lower bioavailability by raising the pH and redox of the system. Although anaerobic zones have been identified within the laboratory-cultured constructed microbial mats and are likely present in the field constructed microbial mat, the redox conditions of the water column under the constructed microbial mat is the experimental pond remained high even after extended dark periods.

Table 5 presents examples of the metal removal capacity of the constructed microbial mats. Although cell sorption by cyanobacteria and bacteria has long been known as a process of removing metals from aqueous media, the constructed microbial mat system operates with a unique set of mechanisms. Mediation of the chemical environment of the water column under the constructed microbial mat is likely involved in the process. High redox conditions (present also in the dark) and high oxygen during the day likely deposits Mn as $MnO_2$. Microanalysis of constructed microbial mats exposed to zinc (Zn) and manganese (Mn) show little congruency of the metal deposits with cell morphology, indicating that cell sorption may not be the primary mechanism of metal deposit, rather it is the aforementioned mediation of the local chemical environment.

TABLE 5

Metal and metalloid removal

| Treatment System | Initial concentration, mg/L | Removal rate, mg metal/m² mat/h |
|---|---|---|
| Free floating constructed microbial mats[1] | Pb: 117 Se: 37 As: 100 | 129 6 RND[2] |
| Mat immobilized on floaters[3] | Mix of Zn: 22 Mn: 18 | 313 462 |
| Excised constructed microbial mats[4] | Mix of Cu: 284 Zn: 3,021 Cd: 19 | 378 3,778 356 |
| Mat covering flow-through pond of acid mine drainage | Mn: 3.3–6.5 | 2.59[5] |
| Floating constructed microbial mat in batch | $U^{238}$: 0.12 | 3.19 |
| Flow-through baffled tanks with constructed microbial mat on glass wool in mixed metal solution | Cr: 24 Co: 24 | 10,129 10,052 |

Pb = lead, Se = selenium, As = arsenic, Zn - zinc, Mn = manganese, Cu = copper, Cd = cadmium, Cr = chromium, $U^{238}$ = uranium isotope.
[1]Free floating constructed microbial mat. Self-buoyant constructed microbial mats were cultured on the surface of laboratory ponds containing lead (Pb) or selenium (Se). Initial solution of selenate was reduced in part to elemental selenium which deposited in the surface constructed microbial mat. Pb was deposited in the constructed microbial mat as lead sulfide. The pH conditions for the free floating constructed microbial mats was pH 6–8.
[2]RND. Rate not determined. 1,746 mg As/M² was removed by day 19. Interim samples of the water column were not taken.
[3]Mat immobilized on floaters. Mat was attached to glass wool balls which were floated in Zn/Mn-contaminated water at pH 7–9.
[4]Excised constructed mircobial mats. Small sections of constructed microbial mat were excised and applied to a mixed solution of Cu, Zn, Cd and iron (Fe) sample from Iron Mountain Mine drainage in California. The pH was adjusted to pH 3—4 before adding constructed microbial mat sections. Fe was not measured.
[5]g metal/m² mat/d

EXAMPLE 5

Bioremediation of Chlordane

Constructed microbial mats were constructed specifically for chlordane degradation by using cyanobacterium, *Oscillatoria* sp., and the purple autotrophic bacteria, resistant to elevated concentrations (>2,000 mg/L) of chlordane, using the methods described in Example 2. Chlordane-resistant strains were used to inoculate for the development of multispecies constructed microbial mats. To construct a constructed microbial mat, organic nutrient substrate, such as ensiled grass clippings (7 g/L wet weight), were added to enriched medium (Allen & Arnon 1955) together with the chlordane-resistant microbes described above. Within 7 to 10 days multispecies, chlordane-resistant constructed microbial mats were formed. These constructed microbial mats, containing autotrophs and heterotrophs, were tightly annealed by the slime in a gel matrix and floated on the surface of the water column. Sections of the constructed microbial mats were added to covered beakers containing a 50 mL water column.

After constructed microbial mats began to show growth in the beakers, 200 mg/L chlordane (without solvent) was added to the water columns. Although chlordane is not soluble in water, the active sequestering of constructed microbial mat filaments drew the droplets of chlordane into the microbial matrix, thereby avoiding the problem of achieving chlordane solubility for cell contact.

Mat-chlordane beakers were prepared to provide material for a daily sampling over a 5-day experimental period. On each sampling day, all materials from the beakers (constructed microbial mat and water column) were harvested and extracted. Solid portions (constructed microbial mats) were extracted with Soxhlet extraction (EPA 1986b) using six reflux cycles, and water columns were extracted in chloroform using a separatory funnel. Combined extracts from constructed microbial mats and water columns were concentrated on a rotary evaporator to a final volume of 1 mL and filtered to remove sediments. Concentrates were analyzed for chlordane concentrations with high performance liquid chromatography (HPLC; Beckman Instruments with System Gold programmable detector equipped with a 10-cm Whatman RCA II column). The mobile phase was a methanol:water 60:40 gradient with a total retention time of 20 min.

Figure 13A:
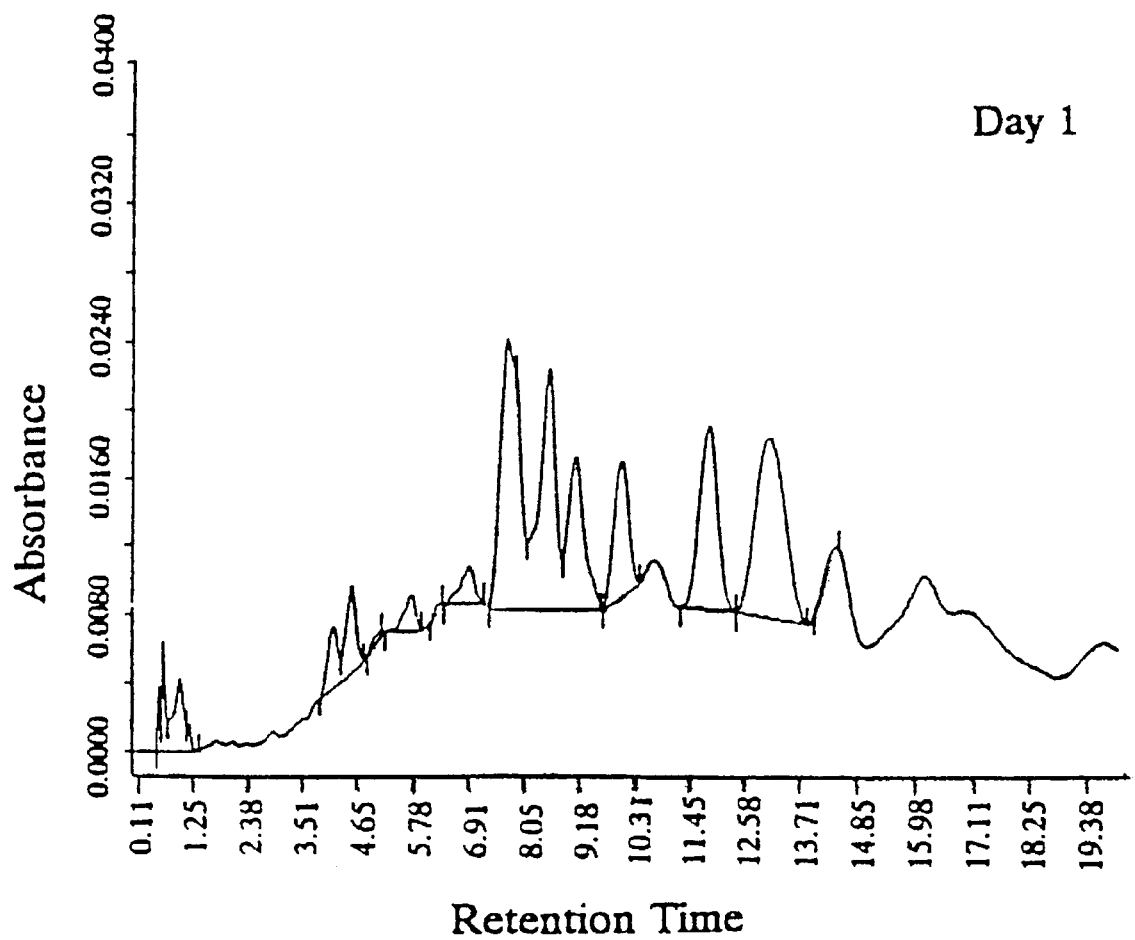
FIGS. 13a–c are HPLC chromatogram series from a 5-day treatment of chlordane contaminated water by chlordane-resistant constructed microbial mat. Chlordane contaminated water (200 mg/L) was treated with constructed microbial mats. The entire treatment systems (mats and water columns) were harvested, extracted, and analyzed on days 1, 3, and 5.
Figure 13B:
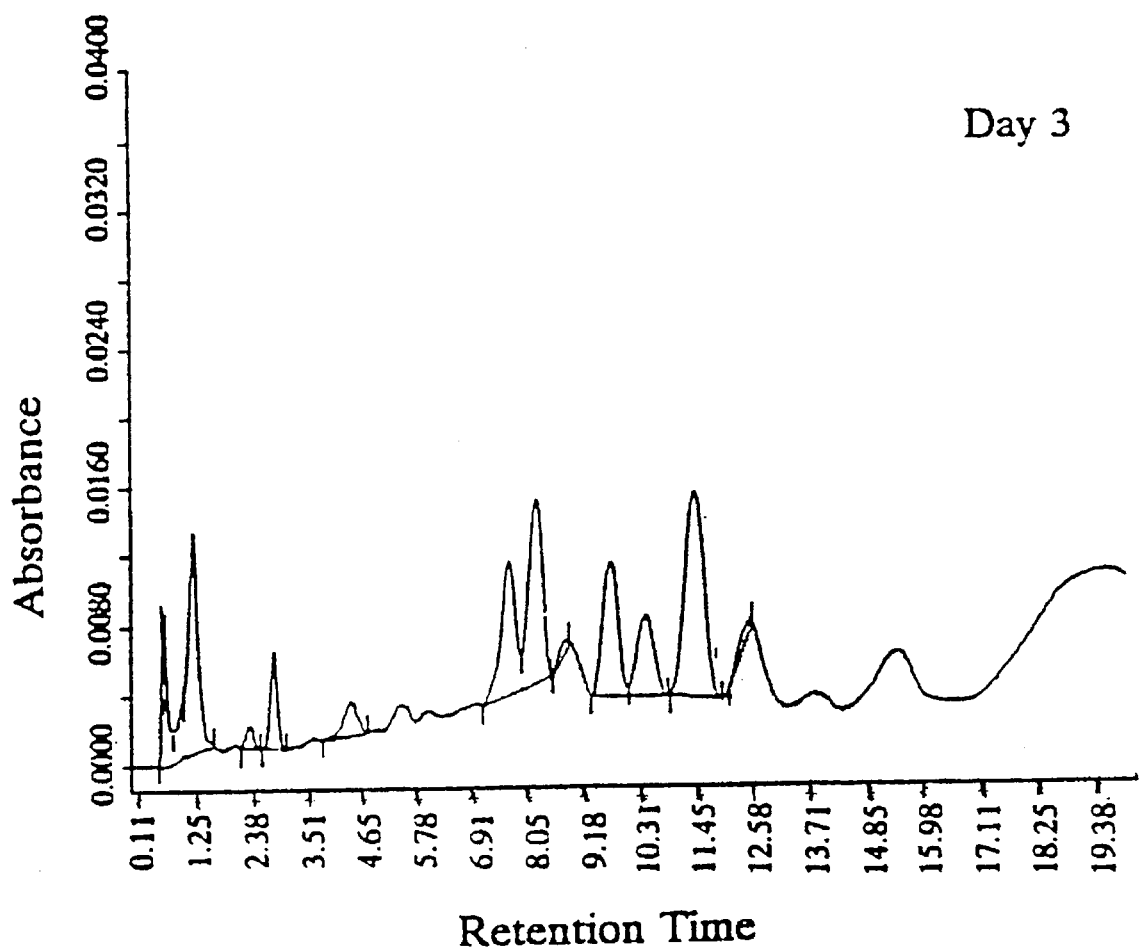
Figure 13C:
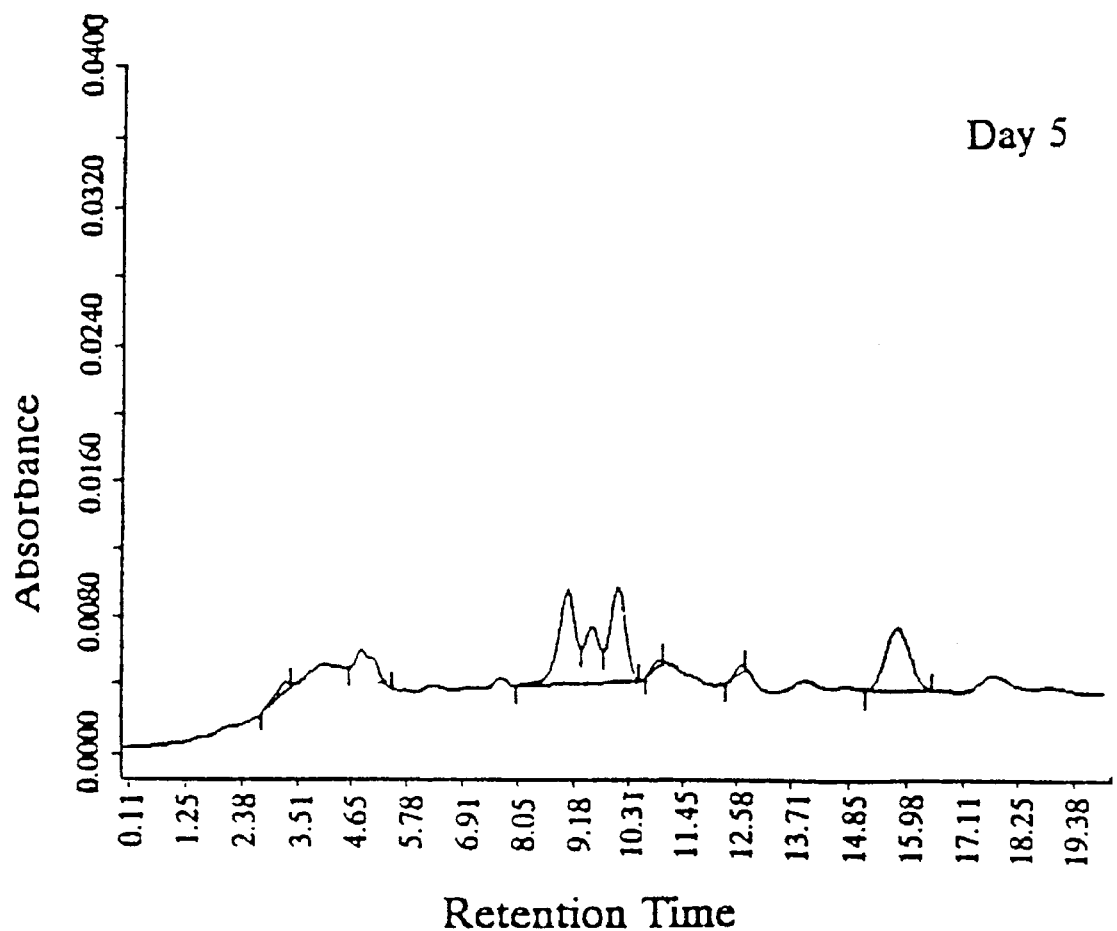

In separate experiments, various microbial components of the constructed microbial mats were assessed for chlordane-degrading capacity. Controls contained heat-sterilized growth medium with ensiled grass.
Results:

FIGS. 13a–c shows the reduced peaks of the chlordane chromatograms which indicated rapid reduction in chlordane concentration. This degradation was apparent in the first day of constructed microbial mat exposure and continued at a constant rate through day 6. FIGS. 13a–c are HPLC chromatogram series from a 5-day chlordane-resistant constructed microbial mat treatment of chlordane. Chlordane contaminated water (200 mg/L) was treated with constructed microbial mats. The entire treatment systems (mats and water columns) were harvested, extracted, and analyzed on days 1, 3, and 5. FIG. 13a shows the chlordane chromatogram of Day 1. FIG. 13b shows the chlordane chromatogram of Day 3. FIG. 13c shows the chlordane chromatogram of Day 5.

Figure 14:
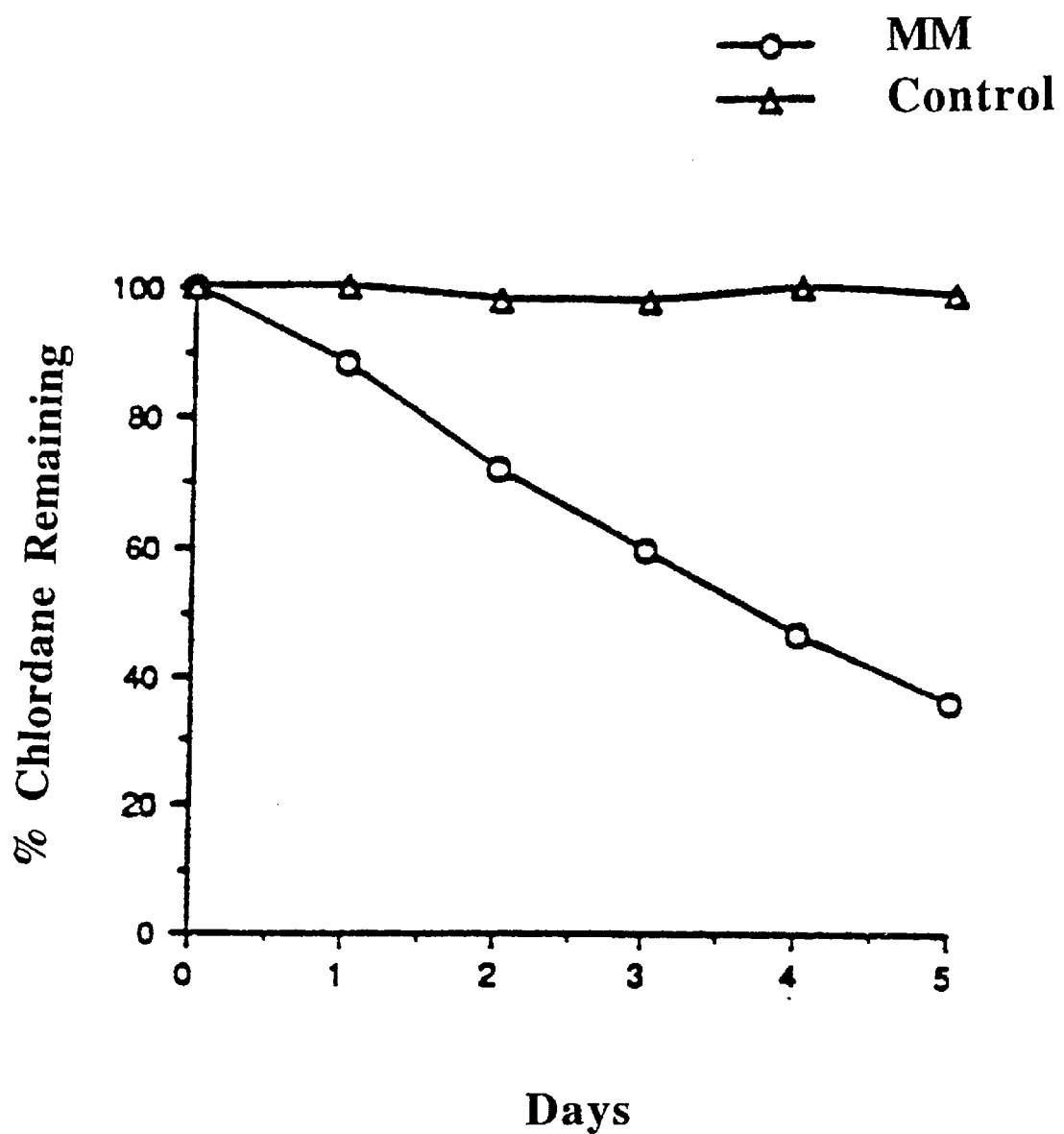
FIG. 14 shows the chlordane removal by a chlordane-resistant constructed microbial mat 5-day treatment of chlordane. Chlordane contaminated water (200 mg/L) was treated with constructed microbial mats. MM=constructed microbial mat.

The degradation rate of chlordane (200 mg/L) is given in FIG. 14. FIG. 14 shows the chlordane removal by a chlordane-resistant constructed microbial mat 5-day treatment of chlordane. Chlordane contaminated water (200 mg/L) was treated with constructed microbial mats. MM=constructed microbial mat.

After 6 days the microbial population diminished in the water column and sedimented at the bottom of the beaker. At the same time, complete constructed microbial mats remained intact and showed active growth for extended periods (>30 days). Although nutrient supplements were required to maintain the bacteria outside of the constructed microbial mat system, no supplements were necessary for the maintenance of the constructed microbial mat. The self-maintenance of the constructed microbial mat, resulting from the capacity to fix both nitrogen and carbon, may be a distinct advantage for low-cost bioremediation.

Kennedy et al (1990) demonstrated a relatively slow degradation rate of chlordane by the white-rot wood fungus *Phanerochaete chrysosporium*. In these experiments the organisms were cultured under nutritionally limited conditions obligating the production of chlordane-degrading lignase.

The constructed microbial mat system showed rapid degradation of chlordane.

EXAMPLE 6

Bioremediation of Organic Molecules in Estuarine Sediments and Pulp Wood Mill Effluent The constructed microbial mat, as described in Example 1, was developed as a free-floating biomass in quiescent laboratory ponds or immobilized to a variety of inert substrates. Constructed microbial mats were made resistant to toxic concentrations of the contaminant before the experiment is performed.

A summary of the experiments are represented in Table 6 below.

TABLE 6

Summary of mineralization experiments conducted

| Experiment | Contaminant Concentration | Specific Activity (mCi/mM) | Light-Dark Cycle |
|---|---|---|---|
| Chlordane in $H_2O$ | 10 μg/75 mL $H_2O$ | 5.91 | 12L:12D |
| Chlordane in sediment | 10 μg/5 mL sediment slurry | 5.91 | 12L:12D |
| PCB in $H_2O$ | 10 μg/75 mL $H_2O$ | 4.37 | 12L:12D |
| TCE in $H_2O$ | 0.002 μg/mL $H_2O$ | 14.2 | 24L/24D |
| TCE + Zn in $H_2O$ | 0.002 μg/mL $H_2O$ 20 mg/L Zn | 14.2 | 24L 24D |

A series of experiments examined chlordane uptake and degradation by removal rates from the water column, generation of metabolites and mineralization to $CO_2$ in 21 days. Although chlordane is not readily soluble in water, a globule of chlordane was sequestered by a floating constructed microbial mat by means of contractile biofilms produced by the constructed microbial mat. Initial addition of 10 μg of $^{14}C$-chlordane (specific activity was 5.91 mci/mM) was made to 75 mL of water containing 1.1 g of constructed microbial mat. The experiment was conducted under 12L:12D (12 hours light: 12 hours dark) conditions.

Two-hundred fifty milliliters of estuarine sediment (approximately equivalent to 300 g) from the tidal flats at the Skidaway Institute of Oceanography were added to seawater to create a 400-mL volume. Five milliliters of this slurry were added per glass flask. An aliquot of blended microbial mat slurry and 10 μg of $^{14}C$ chlordane, dissolved in 10 μL of ethanol, was added to each flask. Controls were autoclaved constructed microbial mats and sediment slurries. Flasks were held on a 12L:12D or 24D cycle. At the end of each incubation period, the constructed microbial mat-sediment mixture was shaken and the floating constructed microbial mat was removed and analyzed for $^{14}C$.

Extraction: Chlordane and its metabolites were extracted with chloroform:methanol by the procedure of Bligh & Dyer (1959). After centrifugation the lower organic phase was taken to near dryness with a rotary evaporator and taken up in a small volume of chloroform. An aliquot of the organic phase was counted. The radioactivity of particles in the aqueous phase was determined by passing the aqueous phase through a glass fiber filter and the filter placed in scintillation fluid and counted.

Thin-Layer Chromatography and Autoradiography: The chloroform extracts were applied to silicic acid thin-layer plates. The solvent system used was petroleum ether: ethyl ether (70:30 v/v). Autoradiography using X-ray film (Xomat AR film, Eastman Kodak Co.) of the thin-layer plates was carried out to locate the position of chlordane and metabolites. Radiolabeled spots were scraped from the thin-layer plates and added to scintillation fluid. Radioactivity was determined with a scintillation counter (Tri-Carb 300C, Packard).

Collection of $^{14}CO_2$: After incubation for various times, 2.0 mL of 2M $H_2SO_4$ were added to the sediment slurry and the respired $^{14}CO_2$ was collected in a center well containing a piece of Whatman No. 1 filter paper soaked with 0.4 mL of 2M NaOH. After absorption of the $^{14}CO_2$: by the NaOH for 3 hours, the soaked papers were transferred to a second set of flasks equipped with $CO_2$ traps containing phenethylamine (Eastman Kodak). Two mL of 2M $H_2SO_4$ were added to each flask, and after 3 hours the $^{14}CO_2$ in the phenethylamine-soaked paper was transferred to scintillation vials and counted in the liquid scintillation counter. The two steps for collection of $^{14}CO_2$ were necessary because small amounts of $^{14}C$-labeled organic compounds volatilized and were collected in the NaOH traps.

2,2'.4,4'.5,5'-Hexachlorobiphenyl, PCB

All experiments were conducted in water. 2,2'.4,4'.5,5'-hexachlorobiphenyl (PCB) presents a similar solubility problem in water as that of chlordane. The initial specific activity was 4.37 mCi/mM. The experiment lasted 21 days. Separate experiments, using non-radiolabeled PCB, were conducted to determine presence of chlorinated metabolites by GC/MS analyses.

Trichloroethylene, TCE

Trichloroethylene (TCE) experiments included the substrate alone, and in combination with 20 mg/L Zn. Experiments were initiated with a TCE specific activity of 14.2 mCi/mM. Degradation values are based on mineralization of $^{14}C$-TCE to $CO_2$. Five mineralization trials were performed in a triplicate light or dark series. Appropriate controls were included. $^{14}CO_2$ was collected in KOH. Sealed test tubes were held at 20°–22° C. Lighted tubes were maintained under continuous incandescent and fluorescent lighting. Degradation, as mineralization to $CO_2$ of the originally spiked μg/L of substrate, was calculated at the end of the 15-day experimental period based on the μg of TCE substrate/mat dry weight.

Absorbable Chlorinated Organic (AOX) Compounds From Pulp and Paper Mill Effluent Three 2-L experimental tanks with constructed microbial mats resistant to the contaminants was grown over limestone rocks and control tanks consisting of limestone rocks were used. Constructed microbial mats were constructed as described in Example 1 and made resistant as described in Example 2 to the compounds. The effluents were sampled from a bleached hardwood and softwood kraft mill. Absorbable chlorinated organic (AOX) and color (absorbance at 510 nm, unbuffered) of wastewaters were measured.

RESULTS

Chlordane

Water-based Experiments. A budget analysis of $^{14}C$-chlordane showed that it was 91% mineralized after 21 days and no parent compound remained. See the Table 7 below.

TABLE 7

Mineralization of $^{14}C$-chlordane, $^{14}C$-PCB, $^{14}C$-TCE and $^{14}C$-TCE + Zn in water.

| Contaminant/ Exposure[1] | Light/Dark | Polar Metabolites | $CO_2$ |
|---|---|---|---|
| Chlordane/21[2] | 12L/12D | 2 | 13 |
| PCB/ 21 | 12L/12D | NA | 17 |
| TCE/ 15 | 24D | NA | 21 |
| TCE + Zn/15 | 24D | NA | 23 |

[1]Time in days
[2]78% of large macromolecules were in the aqueous phase.

Of the 91%, 13% of the label was detected as $^{14}CO_2$ and 78% was detected as large macromolecules, predominately cellular protein. It is assumed that most of the $^{14}CO_2$ produced during degradation was sequestered during photosynthesis.

Estuarine Sediment Experiments. Recovered radioactivity was between 85 and 102% of the total added. Results, presented in Tables 8 and 9, show an increasing pattern of mineralization of chlordane over time.

TABLE 8

Distribution of $^{14}$C-radioactivity in different fractions after additon of $^{14}$C-chlordane to sediment and constructed microbial mats
Ten μg of $^{14}$C-chlordane were added to each flask.
Experimental materials were exposed to a 12L:12D cycle or 24L. The amount is the percent of recovered radioactivity from total radioactivity added.

|  | Parent Compound | | | Polar Metabolites[1] | | | Macromolecules* | | | $CO_2$ (fraction) | | |
| --- | --- | --- | --- | --- | --- | --- | --- | --- | --- | --- | --- | --- |
| Analysis Day | 7 | 14 | 21 | 7 | 14 | 21 | 7 | 14 | 21 | 7 | 14 | 21 |
| Sediment L/D | 97 | 90 | 81 | 0 | 1 | 2 | 1 | 5 | 7 | 2 | 3 | 3 |
| Sediment D | 95 | 89 |  | 1 | 2 |  | 2 | 2 |  | 2 | 3 |  |
| Sediment + Mat L/D | 91 | 85 | 68 | 3 | 5 | 5 | 7 | 8 | 11 | 4 | 12 | 13 |
| Sediment + Mat D | 91 | 93 |  | 1 | 3 |  | 2 | 1 |  | 2 | 1 |  |
| Autoclaved Sediment + Mat L/D | 86 | 74 | 49 | 4 | 8 | 11 | 6 | 14 | 27 | 9 | 15 | 12 |
| Autoclaved Sediment + Mat L/D | 97 | 94 |  | 0 | 0 |  | 0 | 0 |  | 1 | 2 |  |

[1]Amount %
*Large Macromolecules in aqueous phase, Amount %

TABLE 9

Distribution of radioactivity between constructed microbial mat and sediment after $^{14}$C-chlordane added to sediment

| Time (Days) | Sediment*[1] | Constructed Microbial Mat*[1] |
| --- | --- | --- |
| 7 | 85 ± 12 | 12 ± 7 |
| 14 | 68 ± 17 | 30 ± 15 |

[1]Relative amount of recovered radioactivity (%)
*For each time period n = 3.
PCB 17% was mineralized to $^{14}CO_2$ (Table 7). No analysis of labeled cellular macromolecules was conducted.

Separate experiments, using non-radiolabeled PCB, were conducted to determine presence of chlorinated metabolites by GC/MS analyses. Results show production of trichloro and tetrachloro-PCB, suggesting progressive dechlorination by the constructed microbial mat.
TCE TCE was mineralized to $CO_2$ alone and in the presence of 20 mg/L Zinc (Table 7). During 15 days, under dark conditions, 119 μg TCE/kg microbial mat was mineralized whereas 147 μg/kg was mineralized in the presence of 20 mg/L Zn. Mineralization rates in the lighted series were likely inaccurate because the photosynthesizing constructed microbial mat was utilizing $^{14}CO_2$ produced.
AOX Reduction in AOX and color are shown in FIG. 15.

Figure 15A:
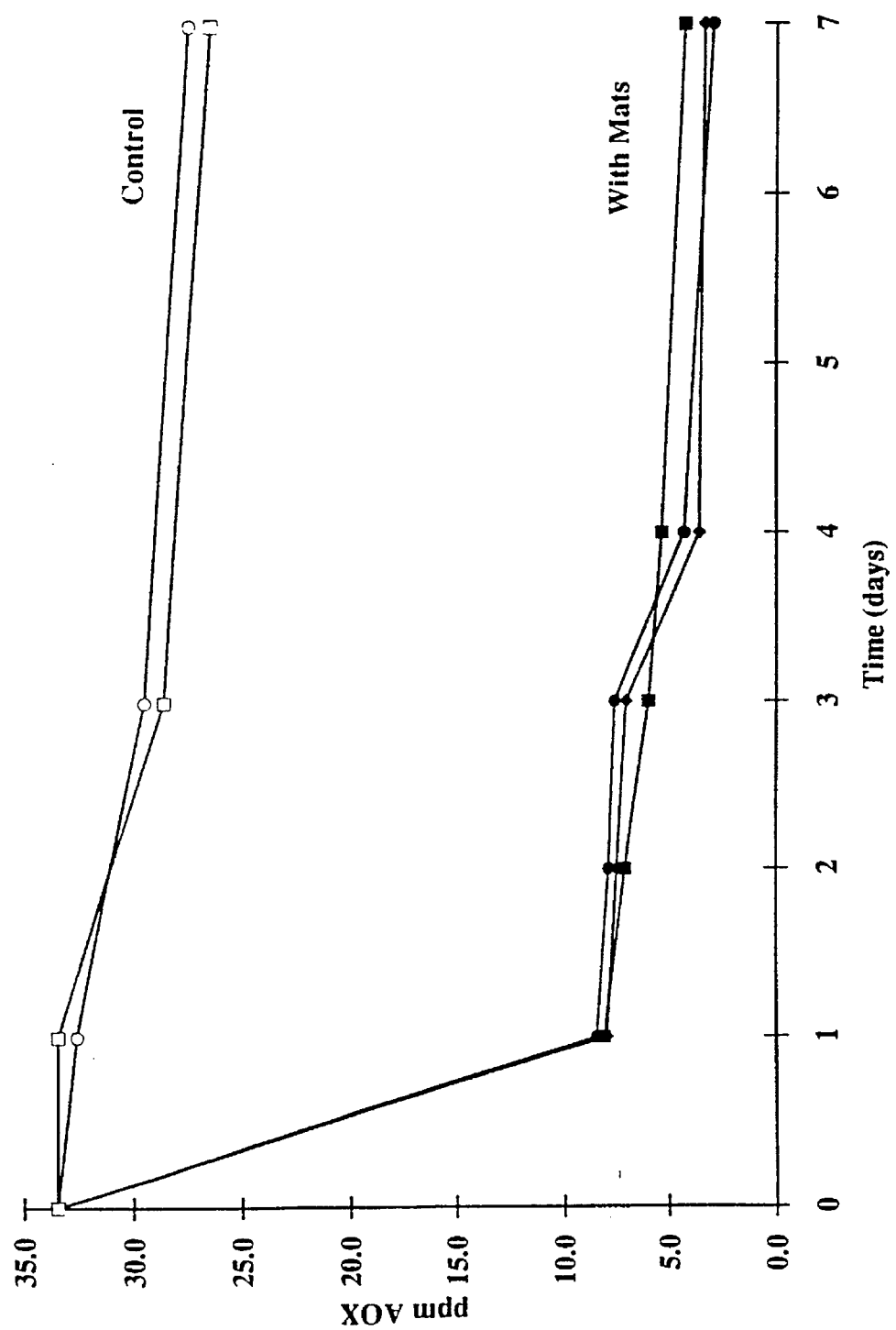
FIG. 15 has graphs showing the effect of constructed microbial mat treatment on absorbable chlorinated organic (AOX) compounds and color reduction in pulp and paper mill wastewater treated with constructed microbial mats. 15a is a graph showing the effect of constructed microbial mat treatment on AOX, measured in parts per million over time. 15b is a graph showing the effect of constructed microbial mat treatment on color reduction, measured in absorbance units, over time.

FIG. 15 is a graph showing the effect of constructed microbial mat treatment on absorbable chlorinated organic (AOX) compounds and color reduction in pulp and paper mill wastewater treated with microbial mats. FIG. 15a is a graph showing the effect of constructed microbial mat treatment on AOX, measured in parts per million over time.

Figure 15B:
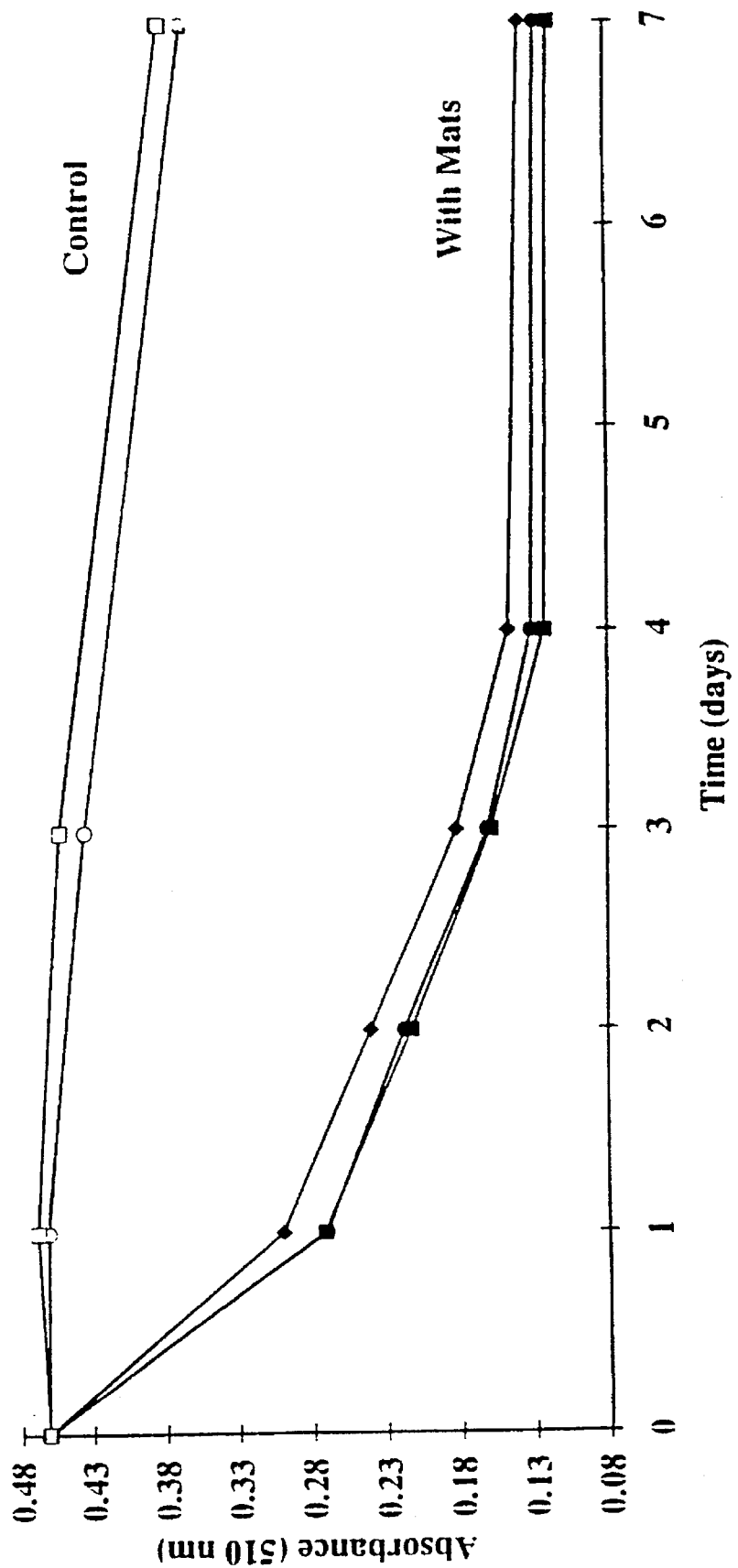

FIG. 15b is a graph showing the effect of constructed microbial mat treatment on color reduction, measured in absorbance units, over time.

Seventy-eight percent of the AOX removal occurred by the end of the first day. After 7 days, approximately 15% more AOX was removed, resulting in a total AOX removal >90% for the effluents. Color removal occurred more slowly; however, after 7 days there was a 72% reduction in absorbance.

Our results showed that chlordane, deposited in sediment, was progressively mineralized by the constructed microbial mat consortium over time and rates surpassed those observed in the natural environment.

Preliminary experiments treating chlordane-contaminated clay soil (200 mg/kg) showed a 20% removal in 25 days. Purple autotrophic bacteria, which are members of the constructed microbial mat consortium and effective degraders, were observed to penetrate the soil to a depth of 4 cm. These results indicate good potential for in situ treatment of sediment and soil.
TCE The rate of TCE mineralization was relatively rapid and was not inhibited by presence of zinc. Constructed microbial mats released negatively-charged bioflocculants which bound the heavy metals before they caused toxic effects or deactivated cellular enzymes. In addition to the TCE/Zn mixture, constructed microbial mats also degraded chrysene and TNT in combination with heavy metals. The metals were sequestered during the degradation process. This capacity of constructed microbial mats to remediate mixed organic/inorganic contaminants is unique for microbial remediation systems.
Pulp and Paper Mill Effluents; Mixtures of Chlorinated Organics These data indicate removal of chlorinated organics from heterogeneous mixtures contained in these effluents. Since effluent color is associated with chlorinated aromatic compounds, decreases in absorption correlates with AOX reduction. On-site reduction of contaminants in pulp and paper mill effluents is an important issue in terms of environmental compliance.

EXAMPLE 7

Concentration of Metals from Contaminated Waters for Metal Recovery

Constructed microbial mats, as described in Example 1, and are resistant to concentrations of metals as were described in Example 2, were cultured on coconut mesh and applied to a Colorado mine drainage site in two ways. (1) Constructed microbial mats which were cultured on coconut mesh in a controlled environment, dehydrated and shipped to Colorado. (2) Dry coconut mesh was applied to the pond surface and constructed microbial mat inocula+silage was added. All of the constructed microbial mats were shaded by a variety of materials; black screen or plastic sheets or pads.

A one foot above the pond bottom (pond depth of approximately four feet), dissolved oxygen levels were 0.8–1.5 mg/L. Near the sunken constructed microbial mat+coconut mesh unit, bottom dissolved oxygen was ≧6 mg/L, indicating that photosynthetic activity by the constructed microbial mat maintains high oxygen levels.

Upon analysis of floating microbial biomass, after a period of 2 months, the following metals were concentrated in the microbial biomass. Given the low concentrations of metals in the water and the high concentrations in the constructed microbial mat and coconut mesh after two months, there is significant metal concentration occurring in the constructed microbial mat. See Table 10.

TABLE 10

Metals Removed by Constructed Microbial Mats

| Metal | Normal Range[1] | Metal in Mat Biomass[2] |
|---|---|---|
| Ag | <0.0005–0.0017 | 19 |
| Cd | 0.021–0.112 | 117 |
| Cr | <0.0006 | 99 |
| Cu | <0.001–0.26 | 1,277 |
| Pb | 0.005–0.038 | 15,550 |
| Ni | <0.015–0.038 | 32 |

| Metal | Normal Range[1] | Percent Dry Weight |
|---|---|---|
| Fe | 0.011–2.912 | 5.09 |
| Mn | 3.316–34.01 | 2.10 |
| Zn | 5.9–43.4 | 3.42 |

EXAMPLE 8

Bioremediation of Mine Drainage

Pond Construction.

Figure 16:
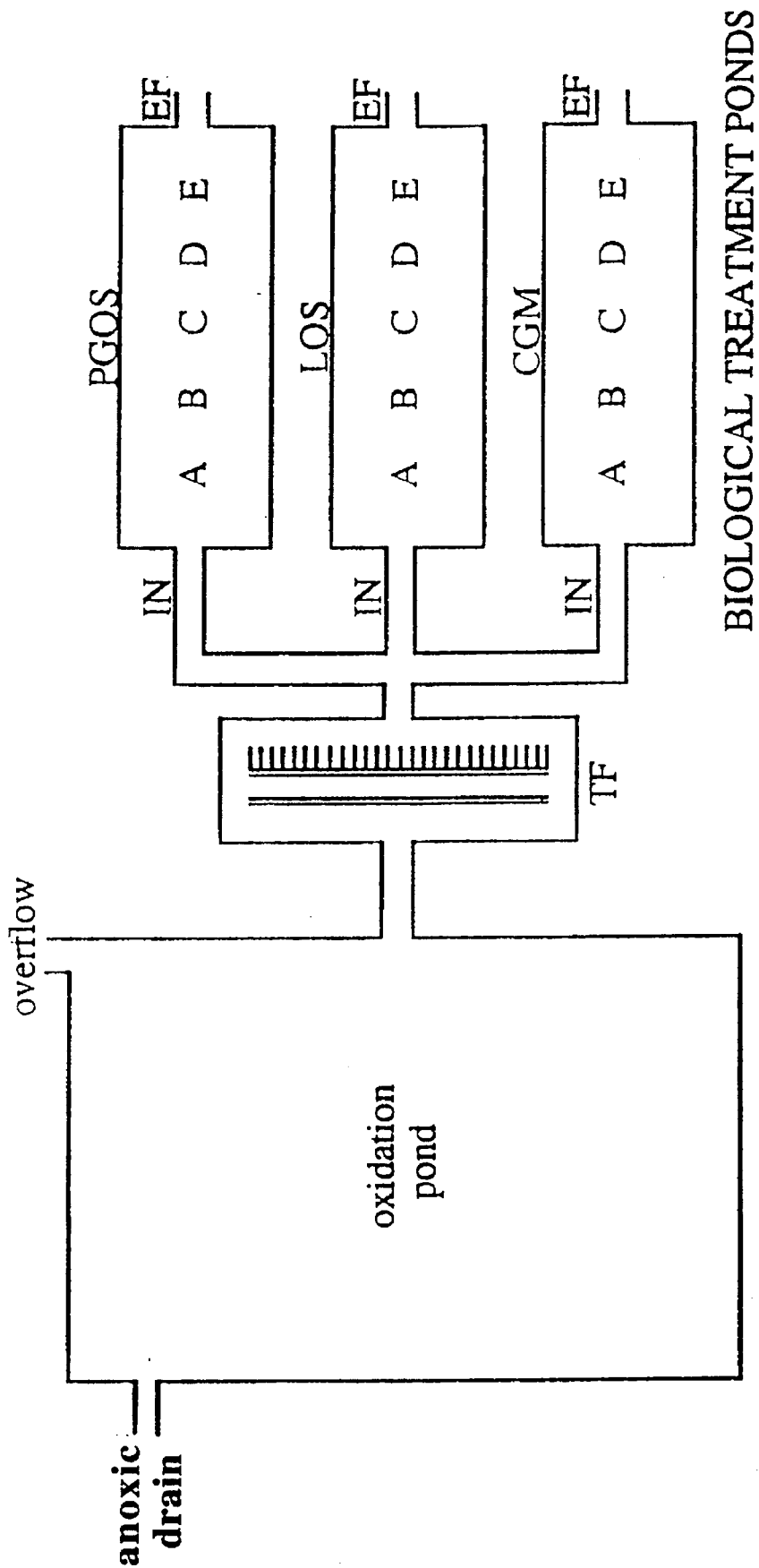
FIG. 16 is a schematic of a design of a treatment of acid coal mine drainage contaminated with metals such as Fe and Mn. An oxidation pond is shown, along with TF, trickling filter; IN influent water; A–E, additional sample points for manganese and iron; CGM, constructed microbial mat with green algae as a support structure; LOS, limestone-*Oscillatoria* pond; PGOS, pea gravel-*Oscillatoria* pond. The design is not drawn to scale.

FIG. 16 illustrates a design for the treatment of acid coal mine drainage contaminated with Fe and Mn. FIG. 16 is a schematic of a design of a treatment of acid coal mine drainage contaminated with metals such as Fe and Mn. An oxidation pond is shown, along with TF, trickling filter; IN influent water; A–E, additional sample points for manganese and iron; CGM, constructed microbial mat with green algae as a support structure; LOS, limestone-*Oscillatoria* pond; PGOS, pea gravel-*Oscillatoria* pond. The design is not drawn to scale. Oxidation pond=approximately 1 ha, trickling filter=20 $m^2$; biological treatment ponds (1)=32 $m^2$, (2)=44 $m^2$, (3)=44 $m^2$. Sampling points are OX oxidation pond near effluent; TF, center of trickling filter (water is dripped through two delivery pipes to lower iron concentration); IN, influent water from trickling filter; EF, effluent water from biological treatment ponds; A–E sample points have the following distances from inflow (m): 0.3,1, 2, 5, and 8.

Three ponds, prepared for biological treatment were lined with PVC film. Limestone rocks (2 to 3 cm) were added in two of the ponds and pea gravel (1 to 2 cm) in the third. Rocks were layered in such as way as to construct alternating high and low regions ranging from 2 to 30 cm in depth, spaced 1 m apart.

Development of Inocula for Ponds.

Microbial strains (including *Oscillatoria* spp., green filamentous algae, and purple autotrophic bacteria) were selected from the treatment area and developed into constructed microbial mats in the laboratory. These mature laboratory constructed microbial mats were used as field inocula for the ponds. Mixtures of constructed microbial mats and silage were prepared and broadcast over the pond at rate of 1 to 1.5 L/pond in three applications during a 4-week period. After the constructed microbial mat covered approximately 30% of the experimental pond surface, the drainage water was delivered to the three ponds. Flowrates were increased approximately every 6 weeks from 1 to 2.5 to 5 L/min. Because of the difficulty of maintaining total absence of biomass in field ponds, controlled experiments for metal uptake by clean rocks were performed in the laboratory.

Analysis of Ecosystem Parameters in Field Ponds.

Pond sampling points (2 cm depth) were measured for dissolved oxygen (DO) (Otterbine Sentry dissolved oxygen meter), pH (Orion series 200 with GX series electrode), Eh (Orion 200 series meter with platinum redox combination electrode), conductivity (Fisher Scientific digital conductivity meter), and concentrations of Fe and Mn. Water or constructed microbial mat samples for all metal analysis experiments were hydrolyzed by microwave digestion (CEM Corp. Model MDi2000) and analyzed for metal concentrations by atomic absorption (Varian, Spectra AA-20 BQ, double beam). Additional water samples (1 L), taken from under the constructed microbial mat, were concentrated to 35 mL and analyzed for the presence of flocculating material with the alcian blue assay for algal anionic polysaccharides (Bar-Or & Shilo 1988). The surface charge of the bioflocculants (Zeta potentials) were measured with a Laser Zee meter (Pen Kem model 501).

A floating mat (1 to 2 cm thick), composed of filamentous green algae and cyanobacteria, predominantly *Oscillatoria* spp., grew rapidly in the pond after addition of silage-microbial mat inocula. A secondary mat of cyanobacteria also covered the limestone at the bottom. Thus the metal contaminated water flowed between the double-layered mats. Approximately 6 weeks were required to establish a full pond mat cover, but effective metal removal began in the early stages of mat growth.

Figure 17A:
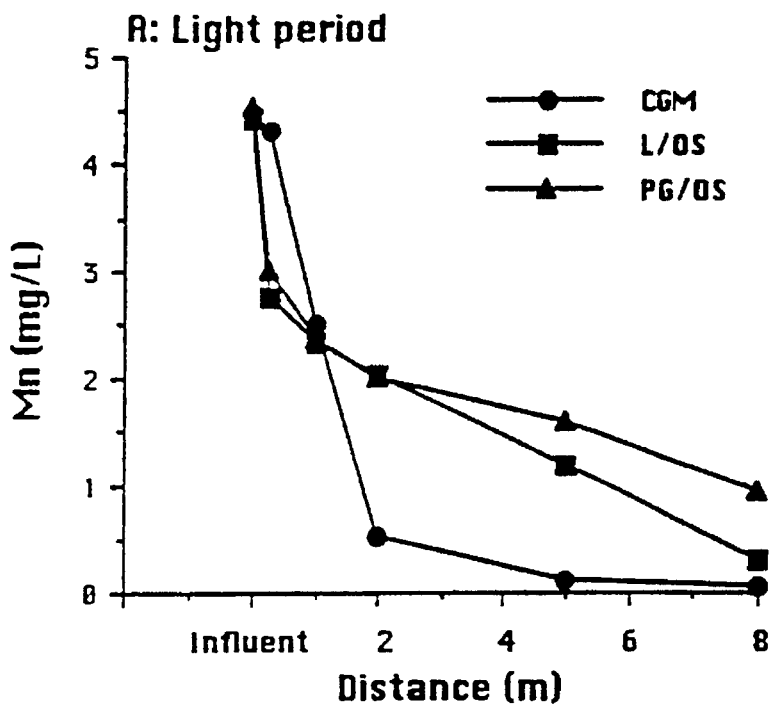
FIG. 17 shows manganese removal from acid mine drainage. Sampling points were measured from the influent point. CGM is the limestone substrate pond with a constructed microbial mat with a green algal support structure, L/OS is the limestone substrate pond and PC/OS is the pea gravel substrate pond. Both became colonized with cyanobacteria. 17a is a graph of samples taken in a light period (11 a.m.). 17b is a graph of samples taken at a dark period (6 a.m.). Control experiments, limestone only, performed in the laboratory, showed approximately 25% Mn removal at a 3-m flow distance.
Figure 17B:
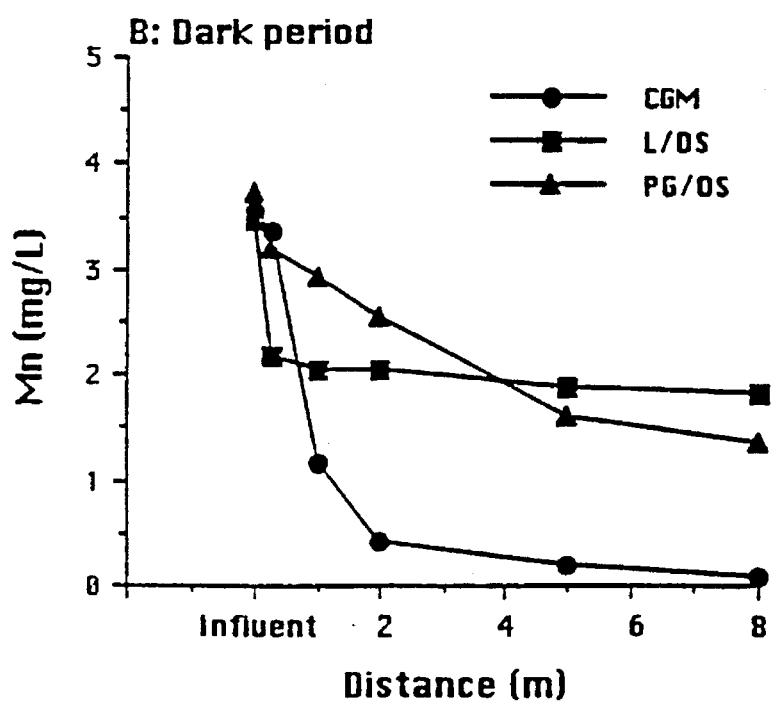

The two ponds designed as controls rapidly became inoculated with an *Oscillatoria* strain resembling that of the inoculated cyanobacteria. This strain formed a thin layer (<0.5 mm) on the rocks. No floating mat developed in these two ponds, and the biomass remained relatively low compared to that in the experimental pond. FIG. 17 shows the metal removal profiles and water conditions in the ponds at a flowrate of 2 to 5 L/min. during light and dark periods. Metals were effectively removed after the inflow water had flowed a distance of approximately 1 to 2 m through the pond. All sampling points beyond that distance (points C to the outflow) showed metal concentrations <1.2 mg/L.

FIG. 17 shows manganese removal from acid mine drainage. Sampling points were measured from the influent point. CGM is the limestone substrate pond with a constructed microbial mat with a green algal support structure, L/OS is the limestone substrate pond and PG/OS is the pea gravel substrate pond. Both became colonized with cyanobacteria. 17a is a graph of samples taken in a light period (11 a.m.). 17b is a graph of samples taken at a dark period (6 a.m.). Control experiments, limestone only, performed in the laboratory, showed approximately 25% Mn removal at a 3-m flow distance.

The two ponds with only *Oscillatoria* spp. films on the rocks also showed metal removal. However, metals were removed more slowly in these ponds, most noticeably at night (FIG. 2-B). Laboratory controls with limestone only showed a 25% Mn removal. These laboratory experiments were added because it was impossible to keep microbial films from contaminating the field pond limestone.

The floating mat in the experimental pond remained healthy and showed no signs of metal deposit on its surface except for iron hydroxide precipitates near the influent. Black deposits of Mn were generally deposited between the two mat layers and did not impact the biological activity of the mat. Redox and DO levels were high during the light period, and pH levels ranged from 6.4 to 7.7. Even after 10 h of darkness, oxygen levels remained at 6 mg/L in some regions of the mat pond. During the photosynthetic period, bubbles of oxygen were entrapped in the slimy matrix that binds the mat. Apparently this sequestered oxygen remains available throughout the night. This is to be expected, because cyanobacteria are unusual in that they have limited ability to utilize organic substrates for energy production in the dark (Kratz & Myers 1955); thus the oxygen consumption remains low in this pond.

Although the conditions of high oxygen and high Eh may be central to the deposit of Mn oxides, other factors may be functional as well. Flocculents were identified in the water column under the mat. Laboratory research showed that specific bioflocculants were released by the mat in response to the presence of Mn+2 (Rodriguez-Eaton et al. 1994). These materials carried surface charges ranging from −58.8 to −65.7 mV. The charges changed to +1.8 in the presence of divalent metal, indicating metal binding to the bioflocculant.

No soil was layered in the pond, so the predictable microbial ecology characterizing the sediment region may not g resent in this system. The primary mechanisms of deposit likely were determined primarily by the chemical/biological processes mediated by the mat. Metals are known to complex with a wide range of organic materials, including microbes and their organic releases. Dunbabin and Bowmer (1992) identify four dominant binding processes that incorporate metals into organic materials: (1) cation exchange, (2) adsorption, (3) precipitation/coprecipitation, and (4) complexation or chelation.

Although metals that are adsorbed, precipitated, or complexed can be released back into solution in an equilibrium response, no such fluctuations were detected during a 4-month experimental period. Additionally, conditions of neutral pH with high DO and redox levels (mediated by the biology of the mat ecosystem) favor the chemical precipitation of Mn oxides and Fe hydroxides. These, in turn, act as reservoirs for additional metal deposits. Also, the pH, redox, and oxygen levels mediated by the mat provide the environmental conditions for bacterial oxidation of Mn by heterotrophic populations colonizing with the mat.

The potential bioavailability of metals is favored by increases in acidity, reducing power, and salinity (Dunbabin & Bowmer 1992). Constructed microbial mats, containing *Oscillatoria* spp. and purple autotrophic bacteria, would tend to lower bioavailability by raising the pH and redox of the system.

Although anaerobic zones have been identified within the laboratory cultured mats and are likely present in the field mat, the redox conditions of the water column under the mat in the experimental pond remained high even after extended dark periods.

EXAMPLE 9

Bioremediation of Pesticides

Constructed microbial mats were used in parallel experiments for efficiency of pesticide degradation and were constructed as described in Example 1 except that soil was added. Constructed microbial mats were formed by constructing an artificial ecosystem in glass containers consisting of a soil base, filtered tap water, a floating layer of organic nutrient substrate (ensiled grass clippings), cyanobacteria (*Oscillatoria* sp.)and purple autotrophic bacteria. Ensiled grass clippings added organic acids, principally lactic and acetic acids, as well as a microbial consortium of fermentative anaerobes to the system. The soil provided motile bacteria, which migrated to the developing floating constructed microbial mat. The final product was a thick, gelatinous green constructed microbial mat which was transferred to the soil surface. The mat was made resistant to toxic concentrations of chlordane as described in Example 2.

The three pesticides examined were: carbofuran (2,3-dihydro-2,2-dimethylbenzofuran-7-yl methycarbamate; paraquat (1,1'-dimethyl-4,4'-bipyridinium dichloride); and chlordane (12,4,5,6,7,8,8-octachloro-3a,4,7,7a-tetrahydro-4,7-methanoindene).

Soil samples were obtained from a banana farm in the Mesopotamia valley region of the Caribbean island St. Vincent with a 2-cm diameter soil recovery probe (Forestry Suppliers, Inc., Jackson, Miss.) to a depth of 10 cm. The soil borer was lined with a plastic tube which was extracted and capped at both ends. Samples were shipped on ice to the Clark Atlanta University Bioremediation Laboratory (Atlanta, Ga.) under U.S. Department of Agriculture quarantine regulations 7 CFR 330.300. Prior to final disposal, all soil samples were autoclaved at 150° C. and 15 psi for one hour.

Chlordane, carbofuran or paraquat (a single pesticide application) was applied in a liquid phase at a rate of 100 mg/kg to 60 g (dry weight) soil samples in 250-ml beakers. Soil was maintained moist with deionized water. The soil was shaded with aluminum foil around the sides and bottom of the beakers. The beakers were covered with clear plastic wrap and incubated in an environmental chamber (Biotronette Mark E) programmed to 12:12 h light:dark and 25° C. for 21 days. All tests were done in triplicate. Controls, containing sterilized banana farm soil, were subjected to the same pesticide application. At the end of the 21-day period, each beaker was analyzed for pesticide residue.

Additional soil sample tests using a mixture of the three pesticides (50 mg/kg each) was similarly incubated and analyzed.

Pesticide-tolerant soil bacteria were isolated by adding sterile tap water (1:1 ,v/v) to non-sterile St. Vincent banana farm soil which was also previously treated with the pesticide mixture. The mixture was stirred with a glass rod and allowed to stand for two hours to facilitate sedimentation. The liquid was then decanted into a glass funnel lined with Whatman no. 2 filter paper. Serial dilutions of the resulting liquid was plated onto agar plates and incubated at room temperature. The agar contained the following constituents in grams per liter: Difco Bacto-agar, 12; $K_2HPO_4$, 4.8; $KH_2PO_4$, 1.2; $NH_4NO_3$, 1.0; $MgSO_4 \cdot 7H_2O$, 0.2; $Ca(NO_3)_2 \cdot 4H_2O$, 0.4; $Fe_2(SO_4)_3$, 0.001.

Colonies that developed on these plates were transferred to enrichment medium (Luria Broth) for growth enhancement. Three resulting bacterial strains were identified by Analytical Services, Inc. (Essex Junction, Vt.).

Experiments to verify the enhancement of native soil bacteria by constructed microbial mat for pesticide degradation Two different configurations of microbial consortia were tested for their ability to degrade the three-pesticide mixture (50 mg/kg each) in sterile soil samples: (1) 0.4 grams (dry weight) of constructed microbial mat and (2) 0.2 g constructed microbial mat +5 ml of a mix of three pesticide-tolerant native soil bacteria (1,012 cell/ml as determined by spectrophotometry). These experiments were subjected to the same treatment as those previously mentioned.

Pesticide extraction and analysis

Procedures adapted from U.S. Environmental Protection Agency (EPA) method 8080A were used for extraction of pesticide residues. Samples were extracted in an acetone:methylene chloride (1:1, v/v) mixture via a 550 Sonic Dismembrator. The extract was concentrated to approximately 1 ml on a Labconco rotary evaporator. The remainder of the extracting solvent was exchanged with hexane. The resulting extract was passed through a florisyl filter presep before analysis via gas chromatography for chlordane and carbofuran or high performance liquid chromatography for paraquat.

Experimental design for mineralization of carbofuran

Mineralization of carbofuran to $^{14}CO_2$ was tested using either constructed microbial mat (carbofuran mixed in soil or liquid media) or, individually, the three previously isolated species of bacteria in liquid media. A total of 5 mineralization trials were performed in a triplicate light/dark series. All control test tubes were heat sterilized before the addition of the radiolabeled compound. Carbofuran concentrations were based [$^{14}C$]carbofuran (specific activity=39.2 mCi/mmol, donated by on radioactive decay rate (later converted to µg/ml). Each test tube contained 48,000 dpm (equivalent to 0.012 µg/ml of FMC Corp., Princeton, N.J.).

Constructed microbial mat plugs were cut from a stationary-phase constructed microbial mat by using a broken edge of a 10-ml borosilicate glass pipette. These were wet weighed before inoculating into each test tube. One-half ml each of a log phase culture of three native soil bacteria were added. These were not standardized with regard to cells/ml. Ten ml of Allen-Arnon Modified Media or 10 g of sterile soil were added to a test tube. [$^{14}C$]carbofuran was added to the media or mixed into the soil.

All test tubes were sealed with cork stoppers wrapped with Teflon tape to make an airtight seal and to eliminate a potential reaction between the test substrate and the stopper material. Potassium hydroxide (KOH) was used as a trapping agent for collecting $^{14}CO_2$. A KOH trap consisted of a 7-ml scintillation vial containing 1 ml of 0.3M KOH.

Sealed test tubes were held at 20° to 22° C. Lighted tubes were maintained under continuous incandescent and fluorescent lighting (5 cm above the media level). Dark flasks were covered with two layers of aluminum foil.

At 24 hours and 8 days, the KOH trap from each tube was removed and replaced with a new KOH trap. On day 15, the final sample trap was counted. All sample vials were filled with 5 ml scintillation fluid (Ultima Gold, Packard Chemical Co., Meriden, Conn.) and counted for 10 minutes on a Packard Bell liquid scintillation counter for total dpm/ml $^{14}C$. Samples of the radioactive tube culture media (1 ml) were drawn and placed into a 7-ml scintillation vial at day 15.

Mineralization Calculations

In trials where a constructed microbial mat in an aqueous medium was used, the constructed microbial mat was dried, weighed and counted for radioactivity. Degradation, as mineralization to $CO_2$ of the originally spiked µg/L of carbofuran substrate, was calculated at the end of the 15-day experimental period based on the µg of carbofuran/mat dry weight.

Identification of Pesticide-resistant Native Soil Bacteria

Analysis of fatty acid profiles identified two species of *Pseudomonas* and one of *Flavobacterium* (most likely *P. stutzeri*, *P. aeruginosa* and *F. indologenes*) isolated from St. Vincent banana farm soils.

Pesticide Degradation by Native Soil Microorganisms

Figure 18:
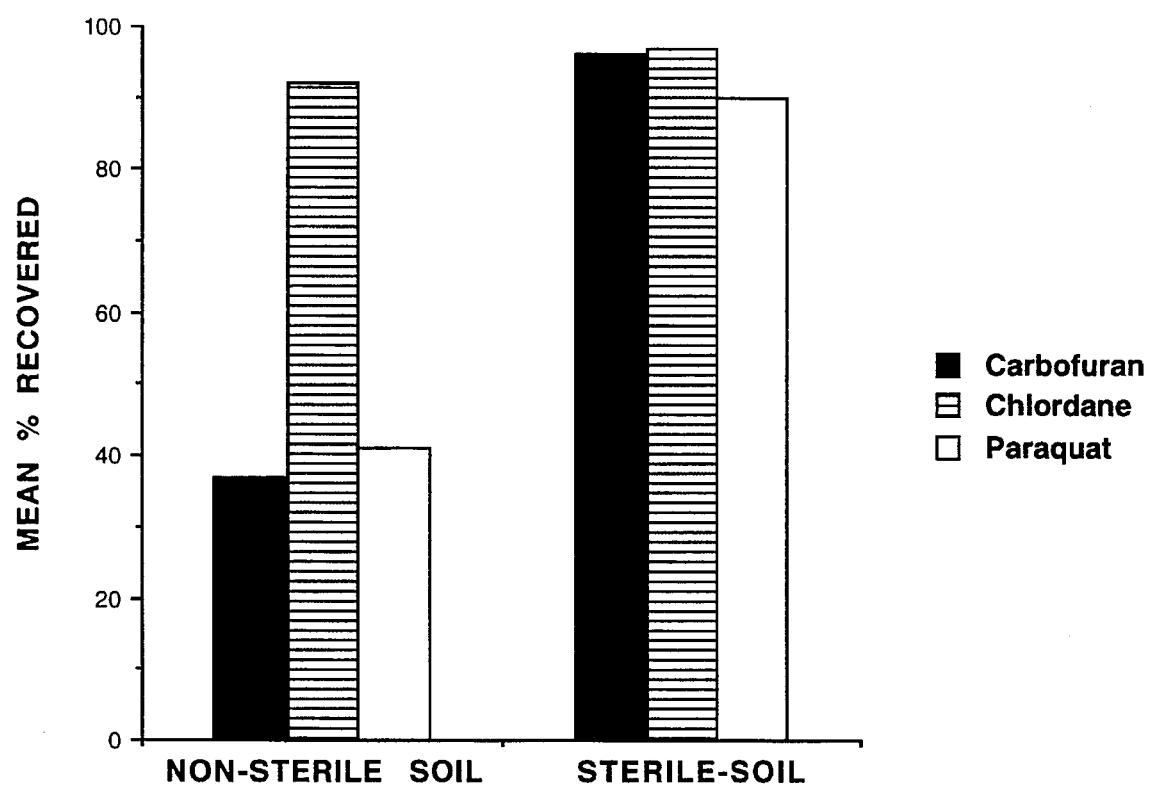
FIG. 18 shows a graph of the degradation of an individual pesticide, either carbofuran, chlordane or paraquat, by constructed microbial mats. The mats were grown in the presence of soil containing indigenous soil bacteria (non-sterile soil) or autoclaved soil (sterile-soil) from a banana farm on St. Vincent Island. The graph shows the mean percent recovery of carbofuran, chlordane or paraquat (initial concentration of 100 mg/kg each) after 21 days of exposure to native soil bacteria (non-sterile soil) versus sterile control soil.

In experiments with the individual pesticide, there was a significant decrease ($p<0.05$) in mean recovery of carbofuran (35.0%), chlordane (91.0%) and paraquat (40.0%) soil concentrations after 21 days of exposure to non-sterile St. Vincent banana farm soil. FIG. 18 shows a graph of the degradation of an individual pesticide, either carbofuran, chlordane or paraquat, by constructed microbial mats. The mats were grown in the presence of soil containing indigenous soil bacteria (non-sterile soil) or autoclaved soil (sterile-soil) from a banana farm on St. Vincent Island. The graph shows the mean percent recovery of carbofuran, chlordane or paraquat (initial concentration of 100 mg/kg each) after 21 days of exposure to native soil bacteria (non-sterile soil) versus sterile control soil. Control (sterile soil) pesticide recovery was nearly 90% or greater (carbofuran, 95.7%; chlordane, 95.3%; paraquat, 89.7%).

Figure 19:
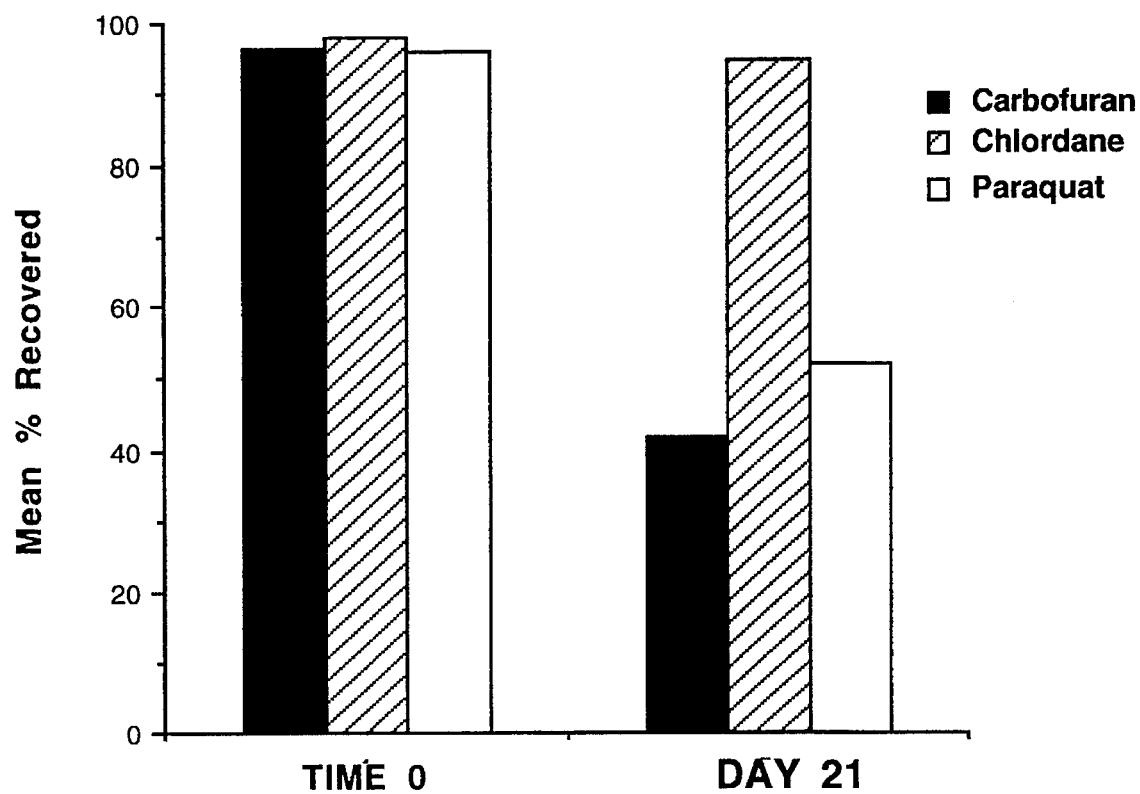
FIG. 19 shows a graph of the degradation of a mixture of the pesticides carbofuran, chlordane and paraquat by constructed microbial mats. The mats were grown in the presence of soil containing indigenous soil bacteria (non-sterile soil) or autoclaved soil (sterile-soil) from a banana farm on St. Vincent Island. The graph shows the mean percent recovery of a mixture of carbofuran, chlordane or paraquat (initial concentration of 50 mg/kg each) after 21 days of exposure to native soil bacteria (non-sterile soil).

In experiments with the three-pesticide mixture, pesticide recovery at the initiation of the experiment (control) was similar to recovery after a 21-day exposure to a single pesticide in sterile soil FIG. 19 shows a graph of the degradation of a mixture of the pesticides carbofuran, chlordane and paraquat by constructed microbial mats. The mats were grown in the presence of soil containing indigenous soil bacteria (non-sterile soil) or autoclaved soil (sterile-soil) from a banana farm on St. Vincent Island. The graph shows the mean percent recovery of a mixture of carbofuran, chlordane or paraquat (initial concentration of 50 mg/kg each) after 21 days of exposure to native soil bacteria (non-sterile soil).

After 21 days of exposure, the pesticide mixture degradation profile was similar to degradation of each individual pesticide, although there was significantly less ($p<0.05$) paraquat degraded. Forty-two percent of carbofuran, 94.0% of chlordane and 52.0% of paraquat was recovered.

Pesticide Degradation by Constructed Microbial Mat and Isolated Native Bacteria

The isolated native bacteria (mix of putative *P. stutzeri*, *P. aeruginosa* and *F. indologenes*) enhanced pesticide degradation of carbofuran when used in combination with constructed microbial mat. The non-sterilized St. Vincent banana farm soil was as effective (42.0% recovery) in degrading carbofuran as was that combination of constructed microbial mat and isolated native bacteria, ($p>0.8$; 42.3% recovery). Constructed microbial mat alone was significantly less effective in degrading carbofuran (52.6% recovery; $p<0.05$). See Table 11.

TABLE 11

| | Degradation of Pesticides | | |
| --- | --- | --- | --- |
| | TREATMENT | | |
| | Non-Sterile Soil | Microbial Mat | Microbial Mat + Isolated soil bacteria |
| Carbofuran | 42.0 | 52.6 | 42.3 |
| Chlordane | 94.0 | 86.6 | 77.0 |
| Paraquat | 52.0 | 60.6 | 56.3 |

The nonsterilized soil was the least effective treatment for degrading chlordane (94% recovery). Constructed microbial mat alone performed better at degrading chlordane than the native bacteria (86.6% recovery) and when the constructed microbial mat was constructed with the three isolated bacteria culture the most effective bioremediation was found, (77.0% recovery).

The non-sterilized soil best degraded paraquat (52.0% recovery) but was not significantly different (p<0.05) from degradation by microbial mat constructed with the three-bacteria culture (56.3% recovery). Constructed microbial mat alone was least effective in degrading paraquat (60.6% recovery).

Mineralization of Carbofuran

Constructed microbial mat and the three soil bacteria individually mineralized [$^{14}$C]carbofuran to $^{14}CO_2$. Conclusions per experimental trial are drawn from and summarized in Table 12.

TABLE 12

| | Mineralization of Carbofuran | | | |
|---|---|---|---|---|
| TREATMENT | Cumulative $^{14}CO_2$ at 15 days (as dpm/ml) | Final media dpm/ml | Final mat dpm | Mineralization (µg/kg) |
| Carbofuran/ mat/AA | | | | |
| Experimental light | 112.7 | 6614.4 | 2274.5 | 3.8 |
| Control light | 563.4 | 9621.5 | | |
| Experimental dark | 1862.2 | 8271.9 | 496.8 | 93.1 |
| Control dark | 150.9 | 11374.9 | | |
| Carbofuran/ mat/soil | | | | |
| Experimental light | 238.6 | | 386.7 | 2.4 |
| Control light | 71.2 | | | |
| Experimental dark | 442.6 | | 322.9 | 4.9 |
| Control dark | 108.1 | | | |

The remaining radioactivity in the media after the experimental period verified that degradation occurred with all biological treatment combinations compared to controls. The amount of radioactivity in the constructed microbial mat after 15 days in aqueous media was nearly 5 times greater under light than under dark. Determination of mineralization under light was hindered by extremely low counts of $^{14}CO_2$ collected in the KOH traps. These extremely low KOH trap counts (often lower than the righted control trap counts) indicated that the rapidly growing constructed microbial mat may be incorporating all available $^{14}CO_2$ produced by mineralization before it reached the trap. Thus, carbon dioxide may have been limiting to the photosynthesizing cyanobacteria. As a result of this re-incorporation, calculations of light series mineralization were mostly irrelevant and probably underestimates. Comparisons of mineralization rates in dark series tubes relative to light series tubes are therefore not appropriate. In the soil treatment, there was slightly greater radioactivity in the constructed microbial mat under light than under dark. Mineralization rate (µg [$^{14}$C]carbofuran/kg dry microbial mat) could only be calculated for constructed microbial mat treatment. Under dark conditions, constructed microbial mat in soil mineralization over 15 days was 93.11 µg/kg versus 4.90 µg/kg for constructed microbial mat in aqueous media.

In these experiments, degradation profiles, whether in the presence of native soil bacteria, by the addition of enriched bacterial cultures or by constructed microbial mat, exhibited a similar pattern. Carbofuran was most readily degraded followed by paraquat. Chlordane was the most recalcitrant compound. The degree of degradation can be related to the compound's structure. Chlordane, with eight chlorine atoms on the aromatic ring, is very stable. Carbofuran, with its methyl carbamate, is readily hydrolyzed, and may provide carbon and nitrogen sources for microbial growth.

The constructed microbial mat, which was resistant to chlordane, degraded the three pesticides better than native soil bacteria. More recent research on [$^{14}$C]chlordane degradation by constructed microbial mat has confirmed that chlordane was mineralized, and in closed vessels, the $^{14}$C was found in the protein fraction of growing constructed microbial mat. This confirmed that $^{14}CO_2$ was utilized by photosynthesizing components of the constructed microbial mat.

EXAMPLE 10

Bioremediation of Petroleum Distillates Including Naphthalene, Phenanthrene, Chrysene and Hexadecane A constructed freshwater consortium of bacteria and cyanobacteria (blue-green algae), or constructed microbial mat, as described in Example 1, degraded four petroleum hydrocarbon compounds. Cyanobacteria, although photosynthetic, use exogenous organic substrates under both lighted and dark conditions (heterotrophy) as a portion of the total carbon requirement for growth. Additionally, cyanobacteria exist in the most inhospitable and caustic environment. Below the cyanobacteria photozone, facultative bacteria colonize. These cyanobacteria/bacteriabiofilms form multilayered laminated constructed microbial mats in the sediment region of shallow water.

This Example is directed to the ability of a constructed microbial mat to mineralize petroleum hydrocarbon compounds: naphthalene, a two-ring polycyclic aromatic hydrocarbon (PAH); phenanthrene, a three-ring PAH; chrysene, a four ring PAH; and hexadecane, a paraffin. Experimental treatments determined the amount of $^{14}CO_2$ produced using $^{14}$C-hydrocarbons as the sole carbon source for the constructed microbial mats.

Constructed microbial mats were developed in laboratory trays by constructing an artificial ecosystem consisting of a soil base, a charcoal-filtered tap-water column, a floating layer of organic nutrient substrate, (ensiled grass clippings), and cyanobacteria inocula, principally *Oscillatoria* spp., and purple autotrophic bacteria. Ensiled grass clippings provide organic acids, principally lactic and acetic acids, as well as a microbial consortium of fermentative anaerobes to the system. Within days a spontaneous succession of bacteria species, migrating from the soil base, colonized the floating silage. The grass clippings additionally served to stabilize the floating constructed microbial mat. The final product was a thick, gelatinous, constructed microbial mat.

The experimental design included a lighted and a dark series for each petroleum hydrocarbon treatment. The purpose of this was to detect mineralization rate differences between all the microbial mat's autotrophs and heterotrophs (lighted series) and only the constructed microbial mat's heterotrophs (dark series). Uniform constructed microbial mat "plugs" (1.00 to 1.69 g, s.d.=0.15) were individually placed in 250 mL acid-washed glass flasks containing 100 mL of Allen/Arnon Modified Medium (Allen & Arnon 1955). These were sealed with a Teflon-coated stopper to eliminate potential reaction between the test hydrocarbon and the stopper material (Bauer & Capone 1985). The $^{14}$C-labeled naphthalene, phenanthrene, chrysene (Amersham/Searle Corp., Arlington Heights, Ill.), and hexadecane (Sigma Chemical Co., St. Louis, Mo.) were spiked at greater than 4,800 disintegrations per minute (dpm)/mL/flask (naphthalene, 9,324; phenanthrene, 5,195; chrysene, 9,639; hexadecane, 9,030). Each petroleum hydrocarbon experimental treatment was conducted in triplicate for both lighted and dark series. Only one hydrocarbon was added to each flask. Mercuric chloride was added (1 mL of 0.125M $HgC_2$) to the control flasks to kill all microorganisms. A 7-mL scintillation vial containing 1 mL of 0.3M KOH was hung inside each flask above the surface of the medium. Sealed flasks were placed in a 33° C. incubator. Lighted flasks were held under continuous fluorescent lighting. At 11, 24, 40, 60, and 90 days, the KOH trap from each flask was removed and scintillation-counted. New KOH traps were installed. Mineralization rates were calculated for days 11, 24, 40, 60, and 90 as a percentage of the initial amount of hydrocarbon spiked into each flask (measured as dpm/flask).

RESULTS

In experimental lighted flasks, the constructed microbial mat plug was rapidly covered with a new green growth of cyanobacteria, in the form of biofilms coating the inside of the flask. By day 11, new growth represented approximately double the original surface area. From days 11 to 24, constructed microbial mats in the experimental dark flasks showed a white filamentous growth. After this time, these plugs became brown and much of the physical integrity of the constructed microbial mat was lost. At the end of the experiment (day 90), these constructed microbial mats were thoroughly decomposed and only detritus remained. Control constructed microbial mats were brownish colored and slightly deteriorated.

The general trends in $^{14}CO_2$ as dpm/mL in KOH were as follows for all four hydrocarbons. In lighted experimental flasks, after day 11, $^{14}CO_2$ amount in KOH traps dropped to near zero. Dark experimental flasks produced KOH trap counts much higher than their counterpart lighted flasks. Naphthalene, phenanthrene, and hexadecane treatments all showed a steady decrease in the amount of $^{14}CO_2$ assimilated in the KOH trap during 90 days. The greatest chrysene value occurred at day 60.

After termination of the experiment, an unweighed and washed ample of constructed microbial mat from each hydrocarbon from the lighted series had the following total dpms: naphthalene, 1,242; phenanthrene, 8,510; chrysene, 40,800; and hexadecane, 1,496. These values indicated that the labeled compounds were attached to or incorporated into the constructed microbial mat cellular contents.

Table 13 shows the cumulative percent mineralization trends. Percent mineralization was calculated based on initial dpm spiking. The near-zero increase in slope of experimental lighted flasks curves after day 11 is due to the extremely low KOH trap dpm counts. Mineralization in the dark experimental flasks increased through day 90, reaching values of 19.0% for naphthalene, 24.1% for phenanthrene, 20.5% for chrysene, and 9.3% for hexadecane. All control flasks (lighted and dark) had mineralization rates less than 2% after 90 days, except for dark hexadecane (2.6%).

TABLE 13

| | Cumulative Percent Mineralization Trends | | | | |
|---|---|---|---|---|---|
| | Day 11 | Day 24 | Day 40 | Day 60 | Day 90 |
| N-Dark | 6.06 | 9.92 | 13.26 | 16.27 | 19.00 |
| Control | 0.02 | 0.06 | 0.08 | 0.12 | 0.16 |
| N-Light | 10.0 | 10.0 | 10.0 | 10.11 | 10.13 |
| Control | 0.136 | 0.21 | 0.28 | 0.35 | 0.41 |

TABLE 13-continued

| | Cumulative Percent Mineralization Trends | | | | |
|---|---|---|---|---|---|
| | Day 11 | Day 24 | Day 40 | Day 60 | Day 90 |
| P-Dark | 6.09 | 11.39 | 16.23 | 20.5 | 24.06 |
| Control | 0.10 | 0.23 | 0.32 | 0.43 | 0.54 |
| P-Light | 0.85 | 0.87 | 0.88 | 0.88 | 0.90 |
| Control | 0.64 | 1.06 | 1.34 | 1.61 | 1.88 |
| C-Dark | 1.15 | 4.41 | 8.21 | 15.27 | 20.46 |
| Control | 0.02 | 0.07 | 0.09 | 0.13 | 0.17 |
| C-Light | 0.14 | 0.14 | 0.14 | 0.15 | 0.15 |
| Control | 0.21 | 0.32 | 0.38 | 0.45 | 0.55 |
| H-Dark | 3.26 | 5.67 | 7.38 | 8.55 | 9.32 |
| Control | 0.10 | 0.72 | 1.39 | 1.97 | 2.57 |
| H-Light | 2.89 | 2.91 | 2.92 | 2.93 | 2.95 |
| Control | 0.01 | 0.02 | 0.02 | 0.11 | 0.33 |

Our results clearly suggest that constructed microbial mats have the capability to bioremediate petroleum contaminated sites.

EXAMPLE 11

Bioremediation of Explosives and Propellants including TNT and DNT

Bacterial consortia (BC) were isolated from TNT-contaminated soil collected from Bangor Naval Submarine Base, Washington. These consortia were made resistant to the target substrate by incubating with increasing concentrations of TNT, added as an acetone solution (TNT does not dissolve readily in aqueous media). Similarly, TNT-tolerant *Oscillatoria* spp. and purple autotrophic bacteria were developed by incubation with TNT, TNT-OS. New constructed microbial mats (TNT-mats) were constructed from the BC and TNT-OS by co-culturing all tolerant microbes together with the organic nutrient substrate, ensiled grass clippings. The ensiled grass added fermentative bacteria to the consortium.

Two types of microbial materials were tested for TNT degradation: the BC group and the constructed mats, described above. Additionally, co-metabolism studies were performed with the BC, using a 0.1% benzoic acid solution along with the TNT.

Bacteria and constructed microbial mats were supplemented with minerals. Except for co-metabolism experiments (and having TNT added as an acetone solution for bacteria), no carbohydrate additions were made. Because the constructed microbial mats are photosynthetic, they produced an internal supply of energy molecules and did not depend on the TNT nutrient value during light periods. All constructed microbial mat cultures were maintained in a 14:10 light:dark cycle.

Degradation of TNT was examined by an NaOH plate assay (Osmon or Klausmeier 1972) and by high-performance liquid chromatography (HPLC). The HPLC analyses were performed on a Perkin-Elmer C-18 reverse-phase column with methanol/water (1:1) as the mobile phase and a flowrate of 1 mL/min. Metabolites were derivatized with trifluoroacetic acid anhydride. Compounds were detected with an LC85B Perkin Elmer Ultraviolet Detector at 254 nm.

HPLC analyses of TNT (175 mg/L) treated with BC showed a 75 to 97% degradation in 12 days. When grown in 100 mg/L TNT, supplemented with benzoic acid, an 80% degradation was achieved in 11 days Therefore, co-metabolism did not improve the degradative efficiency of the BC.

TNT-mats exposed to 100 mg/L TNT showed >99% degradation in 6 days. FIG. 19 shows a graph of the degradation of TNT by a constructed microbial mat which was resistant to toxic concentrations of TNT. Up to 30 minutes elapsed between pouring the TNT medium into dishes and taking the first measurement in any experiment. During this time period, adsorption to the constructed microbial mat could have occurred and perhaps all of the TNT was not in solution at that point, thus the initial concentration would be lower than the expected 100 mg/L. In this experiment, more than 90% of the TNT was degraded by day 3. In separate experiments with lowered concentrations of TNT (50 mg/L), the TNT-mats showed >99% degradation in less than 1 day.

Four expected metabolites increased with time, but their concentrations remained low. Combined concentrations of all detected metabolites never exceeded 10 mg/L, suggesting that further metabolism of these materials was occurring. The metabolites detected during the degradation process were 2-amino-4,6 dinitrotoluene (2-amino-DNT); 4-amino-2,6-dinitrotoluene (4-amino-DNT); 2,4-dinitrotoluene (2,4-DNT); and 2,6-dinitrotoluene (2,6-DNT). Due to the HPLC detection limits, the occurrence of trinitrobenzene (TNB) and m-dinitrobenzene (m-DNB) is uncertain. If present, the concentrations were <1 mg/L The NaOH plate assay gave qualitative indications of the degradation of 100 mg/L TNT by the BC group and the TNT-mats. Preliminary mineralizations experiments with C-labeled TNT showed no mineralization of TNT in a 23-day period.

TNT-mats showed much higher rates of degradation than did the BC group alone. Although both BC and TNT-mats were consortial groups of microbes, the TNT-mats probably contained a greater number of microbial species. In addition, the laminated structure of the constructed microbial mat creates discrete regions of unique chemistry characterized by oxic and anoxic regions in dose proximity. These zones harbor anaerobic and aerobic bacteria, producing a multi-functional unit that likely degrades recalcitrant organics, such as TNT, more effectively.

Although the detected metabolites indicate a low-level persistence of aromatic compounds, those metabolites were never detected in high concentrations. The total mass of the metabolites was far less than the initial TNT. Additionally, HPLC analysis did not indicate any other metabolites This suggests that the TNT was degraded into products not detectable by HPLC methods used in this research.

EXAMPLE 12

Bioremediation of Leachate Containing Ammonia

One gram (wet weight) of a constructed microbial mat, as described in Example 1, was inoculated into each fabric circle, of approximately 2.5 inches in diameter, and let grow overnight in Allen-Arnon Mineral Media (2:1). Half of the circles were enriched with a purple autotrophic bacteria solution. The circles were removed in the morning, excess liquid was removed and each circle was placed in 50 mls of ammonia solution with a final concentration of 140 ppm (diluted from 400 ppm stocks of ammonium acetate and ammonium chloride). The beakers were placed under lights controlled by a timer with 12/12 hours light/dark cycle.

Each beaker was sampled at different times from time 0 to 96 hours by removing 2 mls of solution. The samples were diluted 1:20, 1:10 or undiluted (5 mls were removed instead of 2 ml) depending on the concentration and were tested with the kit. A fabric control was also tested which consisted of fabric with no constructed microbial mat or purple autotrophic bacteria added. The original solution was also tested at each time point.

Figure 20:
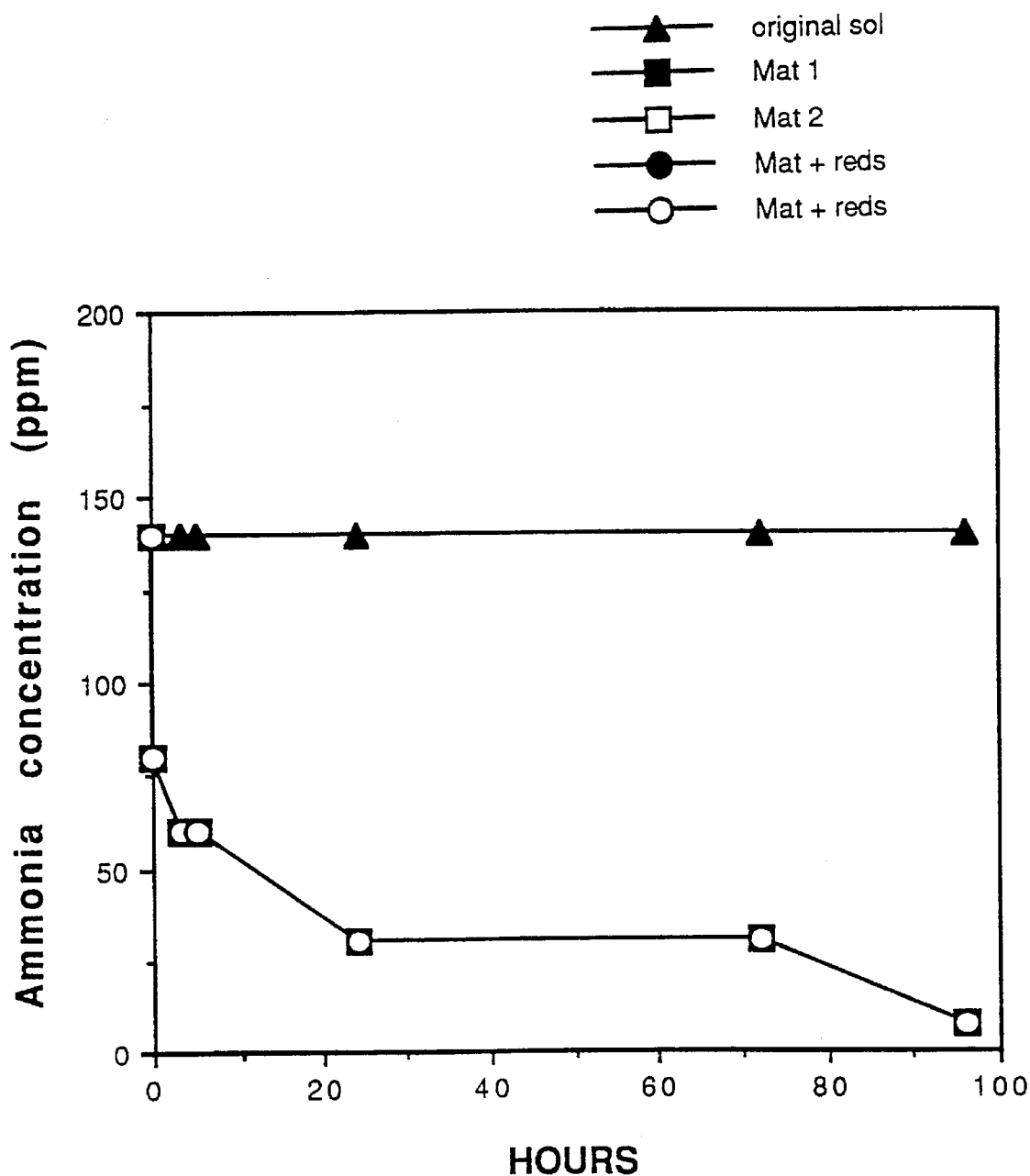
FIG. 20 is a graph of the ammonia removal by constructed microbial mats. Because the data gathered for the samples is exactly the same, the lower line represents four mat conditions. Mats 1 and 2 are constructed microbial mats as described herein, and Mats+reds are constructed microbial mats with red bacteria added.

The original solution (control 1) was tested for the duration of the experiment and always measured 140 ppm of ammonia. The fabric circles without constructed microbial mat or bacteria additions (control 2) consistently measured 100 ppm. Since there was no significant difference in ammonia removal by constructed microbial mat alone or with the addition of bacteria; the four treatments were grouped for illustration. Ammonia levels dropped from 80 ppm at zero hours to 7 ppm at 96 hr. See FIG. 20. FIG. 20 is a graph of the ammonia removal by constructed microbial mats. Because the data gathered for the samples is exactly the same, the lower fine represents four mat conditions. Mats 1 and 2 are constructed microbial mats as described herein, and Mats+reds are constructed microbial mats with red bacteria added.

EXAMPLE 13

Bioremediation of Radioactive Contaminants

Uranium$^{238}$ and chromium in a mixed solution were removed from soil-wash or spent process water obtained from the Hanford Reservation, Wash. Constructed microbial mats, as described in Example 1, were cultured on glass wool and inserted into polycarbonate columns. Water contaminated with Uranium$^{238}$ and Cr was pumped through columns at three rates: 4 ml/h for 18 days; 10 ml/h for 13 days and; 40 ml/h for 7 days.

For the 4-ml/h rate, day 18 removal was 98.8%; for the 10-ml/h rate, day 13 removal was 44.6%; for the 40-ml/h rate, day 2 removal was 59.0%.

EXAMPLE 14

Strontium Removal from Water by Constructed Microbial Mat

Constructed microbial mats, as described in Example 1, were used in the following experiment.

Test unit configurations: All units were acrylic plastic tanks measuring 30×9 cm and with 5 baffles (a piece of acrylic inserted at an angle to create a serpentine water flow through the tank). Glass wool, to a depth of 4 cm, was layered on the tank bottom and constructed microbial mats were cultured on the glass wool. Each unit was covered with plastic film to retain moisture.

Static batch experiment: Initial water volumes, containing strontium, were 300 mL. Initial Sr concentrations were 12.6 mg/L. Three experimental and three control units were used. Static Batch Graphs below. At 4 h, the experimental triplicate mean Sr level was 1.972 mg/L, representing an 84.3% decrease. At 96 h, the mean Sr level was 1.45 mg/L, representing an 88.5% decrease. Control mean levels showed a 18.7% decrease (to 10.243 mg/L) and a 26.4% decrease (to 9.273 mg/L), respectively.

Flow-through experiment: Initial water volumes, containing strontium, were 300 mL. Initial Sr concentrations were 11 mg/L. Three experimental and three control units were used. The entire 300 mL was added to a tank unit, drained, collected and run through the tank again. Each flow-through episode lasted 15 min. This was repeated 12 times/tank. See Flow-through graph for results. There was an approximate linear decrease in Sr concentration per flow. After 12 "runs" the triplicate mean Sr level in the experimental units was 0.277 mg/L, representing a 97.5% decrease, whereas in the control units the Sr level was 9.467 mg/L, representing a 13.9% decrease.

EXAMPLE 15

Production of Bioflocculants by Constructed Microbial Mats

*Oscillatoria* spp, isolated from the constructed :microbial mats as described in Example 1, were cultured in Allen/Arnon media. Water column was assessed for release of bioflocculants by precipitation tests with alcian blue dye. Bioflocculants, present in the water or medium column, bound with the dye causing it to exit the column. Spectrophotometric analyses of residual dye defined the rate of deposition and, thereby, indicated the quantity of bioflocculant present. The presence of bioflocculants correlated with metal deposition from the water column. Glycosyl composition of the bioflocculants was studied to account for the charge characteristics of these molecules. This composition was determined by performing a gas-liquid chromatography analysis of methylated alditols and trimethysilyl derivatives. Negatively-charged bioflocculants were identified. Their presence likely accounts for the metal binding data observed in some experiments.

EXAMPLE 16

Production of Fertilizer and Growth Stimulators by Constructed Microbial Mats Experiments were conducted with corn plants. Soil surfaces in experimental pots were cultured with a constructed microbial mat, developed as described in Example 1, for fertilization and growth stimulation. Soils in control pots were treated with a commercial fertilizer. The corn plants with constructed microbial mats grew larger than the control corn plants.

The greater corn plant height achieved by the experimental group may have been due to the production of indole acetic acid (a plant growth stimulator) by the cyanobacterial component of the constructed microbial mat. Because previously conducted fish feeds research demonstrated significant increase in biomass and protein levels in a constructed microbial mat compared to grass silage starter material, the fixed nitrogen capacity, and therefore the nitrogen fertilizer levels, of soils inoculated with constructed microbial mat would be available for plant growth.

EXAMPLE 17

Production of Animal Feeds by Constructed Microbial Mats

The constructed microbial mat, as described in Example 1, including purple autotrophic bacteria, enhances fish growth. The purple autotrophic bacteria will remove $H_2S$ from the aquatic ecosystem, in addition to the entire constructed microbial mat furnishing a food source for the fish. Removal of $H_2S$ is significant because $H_2S$ negatively affects water quality. The constructed microbial mat can be used as a food source for other animal groups, such as cows, pigs, sheep and chickens. The high protein content of the constructed microbial mat would indicate its potential as a general animal feed supplement.

EXAMPLE 18

Production of Antibacterial Materials by Constructed Microbial Mats

Organic nutrient substrate, ensiled grass (7 g wet weight/L), was added to 1 liter of Allen/Arnon medium together with excised sections of constructed microbial mat inocula. Mat inocula is a small portion of a constructed microbial mat or constructed microbial mat slurry. A constructed microbial mat slurry is made by processing a mature constructed microbial mat in a blender. The initial constructed microbial mat was developed as described in Example 1.

Initially a bacterial bloom occurred in the water column. As the constructed microbial mat developed, as indicated by the size of the cyanobacteria expanding over the surface of the water, the bacterial populations decreased. Bacterial populations are measured by absorbance spectrophotometry (initially correlated with agar plate counts). Mat area was plotted with bacterial populations. Decreases in bacterial population correlated with expanding constructed microbial mat area.

EXAMPLE 19

Production of High Energy Molecules by Constructed Microbial Mats

In this Example, high energy molecules are defined as large hydrocarbons. Pieces of constructed microbial mat, developed as described in Example 1, were extracted with methylene chloride and analyzed with GC/MS according to EPA procedures SW-846, Method #8080. There were no additions of carbon feed, such as carbohydrates, sugars or starches, to the constructed microbial mat. No additional source was added to provide as a feedstock for the synthesis of the high energy molecules. In other words, the energy molecules were apparently constructed, it was theorized, from photosynthetic processes and products. The list of large hydrocarbons found is seen in Table 14.

Table 14 represents a list of some of the hydrocarbons identified in the constructed microbial mats. The ones marked with a * contain 10 or more carbons and, therefore, have high fuel content.

TABLE 14

| Hydrocarbons Produced by Constructed Microbial Mats | |
| --- | --- |
| NAME OF COMPOUND | % PROBABILITY of Identity of Compound |
| Ethane, 1,1,2,2,-tetrachloro | 90 |
| Ethane, 1,1,2,2,-tetrachloro | 87 |
| Ethane, 1,1,2,2-tetrachloro | 76 |
| Phenol, 2,4-bis (1,1-dimethylethyl) | 83 |
| Phenol, 2,4-bis (1,1-dimethylethyl) | 74 |
| *Heptadecane | 96 |
| *Heptadecane | 93 |
| Tetratetracontane | 90 |
| 2-Undecene, 5-methyl- | 70 |
| Dibutyl phthalate | 91 |
| *Heneicosane | 87 |
| *Hexatriacontane | 83 |
| *Dotriacontane | 83 |
| Benzyl butyl phthalate | 87 |
| Benzyl butyl phthalate | 86 |
| *Tetratriacontane | 87 |
| *Tritetracontane | 80 |
| Bis (2-ethylhexyl) phthalate | 83 |

TABLE 14-continued

Hydrocarbons Produced by Constructed Microbial Mats

| NAME OF COMPOUND | % PROBABILITY of Identity of Compound |
|---|---|
| Bis (2-ethylhexyl) phthalate | 80 |
| Phthalic acid, diisooctyl ester | 72 |
| Dodecane, 2,6,1 1-trimethyl- | 83 |
| *Tetradecane | 90 |
| *Hexadecane | 86 |
| *Pentadecane | 93 |
| *Tridecane, 6-propyl- | 76 |
| Octadecane, 1-chloro- | 90 |
| *Hexadecane, 7-methyl- | 86 |

EXAMPLE 20

Formation of an Underground Biocurtain for Treating Contaminants

Laboratory-scale experiments in the biocurtain development were preformed in an acrylic or glass reactors simulating the underground conditions. Separating the inflow and outflow chambers were 2 plates containing holes. This creates a central liquid flow-though chamber that can be packed with the biological material. The chamber lies between the inflow-outflow chambers. Constructed microbial mats, as described in Example 1, were grown, blended in a standard laboratory blender and mixed with sand. This preparation was packed into the central flow-through chamber, creating a biocurtain for treatment of contaminants passing through the area. Contaminant solutions containing metals and organics were allowed to percolate through the biocurtain. Analysis of outflow water (atomic absorption for metals, HPLC for organics) showed large decreases in the contaminant concentrations.

EXAMPLE 21

Formation of Constructed Microbial Mat-root Consortia

This procedure is used to bioremediate soil or sediment, particularly deep soil or sediment contamination. Effective microbes thus are placed in the deep site by the roots of the plants and maintained in the site by the microbial attachment to the roots.

Macrophyte roots were dipped in blended constructed microbial mat slurries, made by developing the constructed microbial mat as in Example 1 and then planted. The coated macrophyte roots are placed in beakers with agar infused with soil salts. Root zones were kept in the dark for approximately one month. At the end of this time the purple autotrophic bacteria and sulfur reducers were present on the roots.

EXAMPLE 21

Preparation of a Kit of a Constructed Microbial Mat

Exploded corn cob particles, a commercial product, were soaked in a minimal requirements media, such as Allen Arnon media, or an inorganic minimal salts media, and constructed microbial mat inocula. These were spread on the surfaces of coconut mesh. Growth of the constructed microbial mat occurred on the mesh. The constructed microbial mat-mesh complex was then dried for later application to a contaminated site.

Exploded corn cob particles were treated as in the above paragraph and spread on the coconut mesh which had ensiled vegetation on it. Mat formation occurred on the mesh more rapidly with the ensiled vegetation than constructed microbial mat formation without ensiled vegetation. The constructed microbial mat-mesh complex was then dried for later application to a contaminated site.

A commercial blow-on product, such as the one sold by Weyerhauser called Soil Guard bonded fiber matrix, containing a binder with fibrous wood particles could also be used in place of the mesh described above. After soaking the product in the media and constructed microbial mat inocula until small constructed microbial mats form on the particles, the complex of constructed microbial mat and blow-on product is dried. The dried complex can then be sprayed onto a contaminated site. The ability to spray the constructed microbial mat complex onto a site allows for precise application and immobilization of the target microbial population at a specific remediation site.

We claim:

1. A composition, comprising, a mixture of a slime-producing cyanobacteria, a purple autotrophic bacteria, and an organic nutrient substrate, forming at least one constructed microbial mat.

2. The composition of claim 1, further comprising a support structure annealed to the constructed microbial mat.

3. The composition of claim 1, wherein the organic nutrient substrate is selected from the group consisting of ensiled vegetation, ensiled grass clippings or other flora, or non-ensiled vegetation, grass clippings or other flora and combinations thereof.

4. The composition of claim 1, wherein at least one constructed microbial mat is resistant to toxic concentrations of contaminants.

5. A kit, comprising a container and a mixture of a slime-producing cyanobacteria, a purple autotrophic bacteria, an organic nutrient substrate, and minimal requirement media.

6. A method for forming a constructed microbial mat, comprising combining purple autotrophic bacteria, slime-producing cyanobacteria, and an organic nutrient substrate to initiate formation of at least one constructed microbial mat.

7. The method of claim 6, further comprising a support structure annealed to the constructed microbial mat.

8. The method of claim 6, further comprising the step of making the constructed microbial mat resistant to toxic concentrations of contaminants.

9. The method of claim 8, further comprising a support structure annealed to the constructed microbial mat resistant to toxic concentrations of contaminants.

10. A method of bioremediation, comprising removing contaminants from a contaminated site with at least one constructed microbial mat, wherein the constructed microbial mat comprises a mixture of a slime-producing cyanobacteria, a purple autotrophic bacteria, and an organic nutrient substrate.

11. The method of claim 10, further comprising a support structure annealed to the constructed microbial mat.

12. The method of claim 11, wherein the support structure is selected from the group consisting of a mesh made from shredded coconut hulls or ground corn cobs, plastic mesh, limestone, glass wool, clay, concrete, wood fiber, corn cob particles, activated charcoal, green filamentous algae, baffles, slowly turning paddles in a waterway, or bioreactor structures and combinations thereof.

13. The method of claim 10, further comprising isolating one or more contaminants from the mat.

14. The method of claim 10, further comprising making the constructed microbial mat resistant to toxic concentrations of contaminants.

15. The method of claim 14, wherein either the slime-producing cyanobacteria or the purple autotrophic bacteria is resistant toxic concentrations of contaminants.

16. The method of claim 14, further comprising a support structure annealed to the constructed microbial mat.

17. A method of production of fuel molecules, comprising contacting at least one constructed microbial mat with organic molecules capable of conversion into fuel molecules by constructed microbial mats under conditions such that the constructed microbial mat converts the organic molecules to fuel molecules, wherein the constructed microbial mat comprises a mixture of a slime-producing cyanobacteria, a purple autotrophic bacteria, and an organic nutrient substrate.

18. The method of claim 17, further comprising a support structure annealed to the constructed microbial mat.

19. The method of claim 17, further comprising making the constructed microbial mat resistant to toxic concentrations of contaminants.

\* \* \* \* \*